(12) United States Patent
Glunz et al.

(10) Patent No.: US 7,112,601 B2
(45) Date of Patent: Sep. 26, 2006

(54) CYCLOALKYL HETEROCYCLES FOR TREATING HEPATITIS C VIRUS

(75) Inventors: Peter W. Glunz, Yardley, PA (US); Brent D. Douty, East Fallowfield, PA (US); Scott W. Martin, Middletown, CT (US); Jeffrey Romine, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/922,096

(22) Filed: Aug. 19, 2004

(65) Prior Publication Data

US 2005/0075376 A1   Apr. 7, 2005

Related U.S. Application Data

(60) Provisional application No. 60/502,067, filed on Sep. 11, 2003.

(51) Int. Cl.
  *A61K 31/415*   (2006.01)
  *C07D 231/12*   (2006.01)
  *C07D 231/14*   (2006.01)
  *C07D 231/16*   (2006.01)

(52) U.S. Cl. .................. 514/406; 514/407; 548/374.1; 548/376.1; 548/377.1

(58) Field of Classification Search ................ 514/360, 514/364, 381, 406; 548/253, 376, 377.1
See application file for complete search history.

(56) References Cited

U.S. PATENT DOCUMENTS 6,045,773 A * 4/2000 Isakson et al. ............. 424/1.81

FOREIGN PATENT DOCUMENTS

| EP | 1 256 628 A2 | 11/2002 |
|---|---|---|
| WO | WO 00/06529 | 2/2000 |
| WO | WO0006529 A1 * | 2/2000 |
| WO | WO 00/10573 | 3/2000 |
| WO | WO 00/13708 | 3/2000 |
| WO | WO 00/18231 | 4/2000 |
| WO | WO 01/32153 A2 | 5/2001 |
| WO | WO 01/47883 A1 | 7/2001 |
| WO | WO 02/04425 A2 | 1/2002 |
| WO | WO 02/100851 A2 | 12/2002 |
| WO | WO 03/007945 A1 | 1/2003 |
| WO | WO 03/010141 A2 | 2/2003 |

OTHER PUBLICATIONS

Lauer, G.M., et al., "Hepatitic C Virus Infection," The New England Journal of Medicine, vol. 345, No. 1, Jul. 5, 2001, pp. 41-52.
Poynard, T., et al., "Randomised trial of interferon α2b plus ribavirin for 48 weeks or for 24 weeks versus interferon α2b plus placebo for 48 weeks for treatment of chronic infection with hepatitis C virus," The Lancet, vol. 352, Oct. 31, 1998, pp. 1426-1432.
Zeuzem, S., et al., "Peginterferon Alfa-2a in Patients with Chronic Hepatitis C," The New England Journal of Medicine, vol. 343, No. 23, Dec. 7, 2000, pp. 1666-1672.
Kolykhalov, A., et al., "Hepatitus C Virus-Encoded Enzymatic Activities and Conserved RNA Elements in the 3' Nontranslated Region Are Essential for Virus Replication In Vivo," Journal of Virology, vol. 74, No. 4, Feb. 2000, pp. 2046-2051.
Duncia, J.V., et al., "Three Synthetic Routes to a Sterically Hindered Tetrazole. A New One-Step Mild Converstion of an Amide into a Tetrazole," Journal of Organic Chemistry, 56, 1991, pp. 2395-2400.
Herr, R.J., "5-Substituted-1H-tetrazoles as Carboxylic Acid Isosteres: Medicinal Chemistry and Synthetic Methods," Bioorganic and Medicinal Chemistry, 10, 2002, pp. 3379-3393.
Koguro, K., et al., "Novel Synthesis of 5-Substituted Tetrazoles from Nitriles," Synthesis, Jun. 1998, pp. 910-914.
Sturino, C.F., et al., "A Convenient Method for the Preparation of Acylsulfonamide Libraries," Tetrahedron Letters, 39, 1998, pp. 5891-5894.
Drummond, J.T., et al., "Convenient Procedure for the Preparation of Alkyl and Aryl Substituted N-(Aminoalkylacyl)Sulfonamides," Tetrahedron Letters, vol. 29, No. 14, pp. 1653-1656, 1988.
Cossu, S., et al., "Unusual Reactivity of 4-Carboxyamido-2-oxazoline Systems: New Synthesis of Optically Active N-Sulphonyl Derivatives," Tetrahedron, vol. 50, No. 17, pp. 5083-5090, 1994.
Mantlo, N.B., et al., "Imidaz[4,5-b]Pyridine-Based $AT_1/AT_2$ Angiotesin II Receptor Antagonists," Bioorganic and Medicinal Chemistry Letters, vol. 4, No. 1, pp. 17-22, 1994.
Yohara, Y., et al., "A New Class of Angiotesin II Receptor Antagonists with a Novel Acidic Bioisostere," Bioorganic and Medicinal Chemistry, vol. 5, No. 17, pp. 1903-1908, 1995.
Kim, D., et al., "Evaluation of Heterocyclic Acid Equivalents as Tetrazole Replacements in Imidazopyridine-Based Nonpeptide Angiotensin II Receptor Antagonists," Bioorganic and Medicinal Chemistry, vol. 4, No. 1, pp. 41-44, 1994.
Gezginci, M.H., et al., "Antimycobacerial Activity of Substituted Isosteres of Pyridine- and Pyrazinecarboxylic Acids. 2.," Journal of Medicinal Chemistry, 2001, 44, pp. 1560-1563.

(Continued)

Primary Examiner—Kamal A. Saeed
Assistant Examiner—Nyeemah Grazier
(74) Attorney, Agent, or Firm—James Epperson

(57) ABSTRACT

Compounds of Formula I are disclosed which inhibit hepatitis C NS5B RNA-dependent RNA polymerase and are useful for treating hepatitis C. Compositions and methods of using these compounds are also disclosed

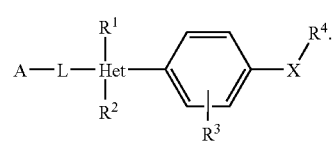

11 Claims, No Drawings

OTHER PUBLICATIONS

Soll, R.M., et al., "3-Hydroxy-3-Cyclobutene-1,2-Dione: Application of a Novel Carboxylic Acid Bioisostere to an In-Vivo Active Non-Tetrazole Angiotensin-II Antagonist," Bioorganic and Medicinal Chemistry, vol. 3, No. 4, pp. 757-760, 1993.

Liebeskind, L.S., et al., "3-Stannylcyclobutenediones as Nucleophilic Cyclobutenedione Equivalents. Synthesis of Substituted Cyclobutenediones and Cyclobutenedione Monoacetals and the Beneficial Effect of Catalytic Copper Iodide on the Stille Reaction," Journal of Organic Chemistry, 1990, 55, pp. 5359-5364.

Kehler, J., et al., "Novel Phosphinic and Phosphonic Acid Analogues of the Anticonvulsant Valproic Acid," Bioorganic and Medicinal Chemistry Letters, 10, 2000, pp. 2547-2548.

Golebiowski, A., et al., "Solid Supported Synthesis of Hydroxamic Acids," Tetrahedron Letters, 39, 1998, pp. 3397-3400.

Taliani, M., et al., "A Continuous Assay of Hepatitis C Virus Protease Based on Resonance Energy Transfer Depsipeptide Substrates," Analytical Biochemistry, 240, 1996, pp. 60-67.

Tan, S-L, et al., "Hepatitis C Therapeutics: Current Status and Emerging Strategies," Nature Reviews/Drug Discovery, vol. 1, Nov. 2002, pp. 867-881.

Still, W.C., et al., "Rapid Chromatographic Technique for Preparative Separations with Moderate Resolution," Journal of Organic Chemistry, vol. 43, No. 14, 1978, pp. 2923-2925.

Gridnev, A.A., et al., "Synthesis of 1-Alkylimidazoles," Synthetic Communications, 24, 11, 1994, pp. 1547-1555.

\* cited by examiner

CYCLOALKYL HETEROCYCLES FOR TREATING HEPATITIS C VIRUS

CROSS-REFERENCE TO RELATED APPLICATIONS

This application claims the benefit of U.S. provisional application No. 60/502,067 filed Sep. 11, 2003.

BACKGROUND OF THE INVENTION

This invention is directed to compounds which inhibit the RNA-dependent RNA polymerase (RdRp) encoded by Hepatitis C virus (HCV). The compounds, or pharmaceutically acceptable salts thereof, are useful for the treatment of HCV viral infections.

HCV is a major human pathogen, infecting an estimated 170 million people worldwide. A substantial fraction of these HCV infected individuals develop serious progressive liver disease, including cirrhosis and hepatocellular carcinoma. (Lauer, G. M.; Walker, B. D. N. Engl. J. Med. (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. In addition, the prospects for development of a prophylactic or therapeutic vaccine appear dim, in spite of intensive research efforts. Thus, there is a clear need to develop effective therapeutics for treatment of HCV infection.

HCV is a positive-stranded RNA virus. Based on comparison of deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. The translated product contains the following proteins: core-E1-E2-p7-NS2-NS3-NS4A-NS4B-NS5A-NS5B. This precursor protein is cotranslationally and posttranslationally processed into at least 10 viral structural (core, E1, E2) and nonstructural (NS2-NS5B) proteins by the action of host cell signal peptidase and by two distinct viral proteinase activities (NS2/3 and NS3).

Although the functions of the NS proteins are not completely defined, it is known that NS3 is a serine protease/RNA helicase, NS4A is a protease cofactor, and NS5B is an RNA dependent RNA polymerase involved in viral replication. It has recently been demonstrated that functional NS5B is required for virus infectivity in chimpanzees (Kolykhalov, A. A. et al. *J. Virol.* (2000), 74, 2046–2051). Because HCV only infects chimpanzees and humans, this result strongly suggests that inhibition of the NS5B RdRp is a viable approach for the development of HCV therapeutic agents.

DESCRIPTION OF RELATED ART

Efforts toward the development of HCV NS5B RdRp inhibitors have resulted in the following disclosures:

Altamura et al. (Istituto Di Ricerche Di Biologia Molecolare) describe diketoacid RdRp inhibitors (WO 00/06529). Altamura et al. suggest that the diketoacids inhibit HCV RdRp by interfering with the binding of phosphoryl groups at the active site of the enzyme.

A series of three disclosures from Viropharma Inc. (Bailey, T. R. et al, WO 00/10573; Bailey, T. R. et al, WO 00/13708; Young, D. C. et al, WO 00/18231) describe HCV RdRp inhibitors. WO 00/10573 covers a series of rhodanine derivatives, WO 00/13708 covers a series of barbituric acid or thiobarbituric acid derivatives, and WO 0018231 covers a series of dihydrobenzothiophene derivatives.

R. Storer (Biochem Pharma, Inc.) has disclosed the use of a series of dioxolane nucleosides for treatment of HCV (WO 01/32153). Hashimoto et al, (Japan Tobacco, Inc.) disclose a series of fused-ring heterocycles as inhibitors of HCV RdRp (WO 01/47883, U.S. 03/0050320), and a similar series of fused-ring heterocycles is also disclosed by Boehringer Ingelheim (WO 02/04425, WO 03/007945, WO 03/010141). ShireBiochem (WO 02/100851) discloses 5-membered carboxylates. Agouron Pharmaceuticals discloses pyran-2-ones (EP 1 256 628).

DESCRIPTION OF THE INVENTION

This invention encompasses compounds which are useful for inhibiting hepatitis C NS5B RNA-dependent RNA polymerase and for treating hepatitis C. Pharmaceutical compositions and methods of treating hepatitis C using these compounds are also encompassed.

One aspect of the invention are compounds of Formula (I)

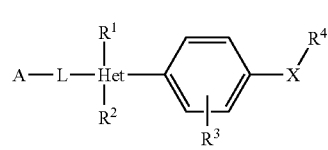

where:

A—L is 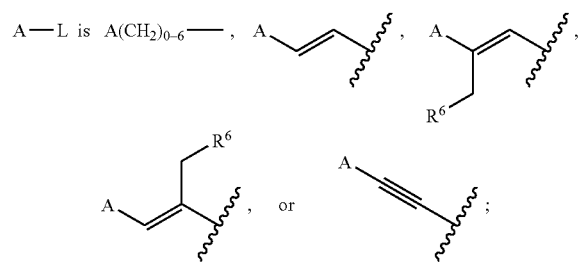

-continued

A is $CO_2R^5$, $CONSO_2R^5$, $SO_2NCOR^5$, 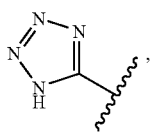

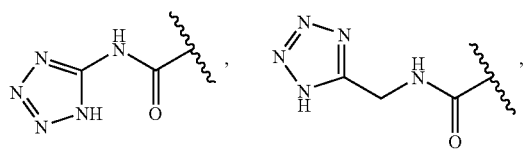

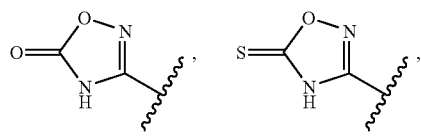

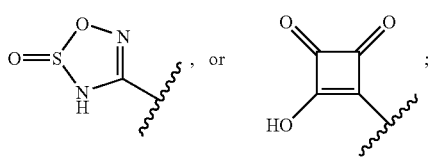

Het is pyrazole, imidazole, oxazole, triazole, thiazole, pyrrole, furan, or thiophene;
X is O, S, $NR^5$, or $CH_2$;
$R^1$ is hydrogen, halogen, $C_{1-6}$alkyl, trifluoromethyl, or phenyl;
$R^2$ is $C_{3-7}$cycloalkyl or $C_{5-12}$ bridged bicycloalkyl;
$R^3$ is hydrogen, halogen, $C_{1-6}$alkyl, or $C_{1-6}$alkoxy;

$R^4$ is 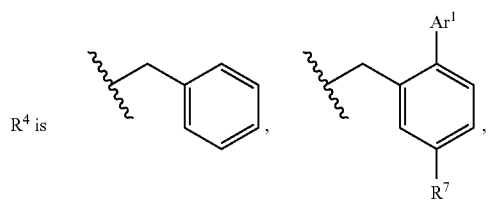

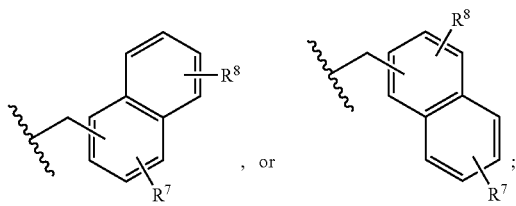

$R^5$ is hydrogen or $C_{1-6}$alkyl;
$R^6$ is hydrogen, methyl, or $OR^5$;
$R^7$ is $C_{1-6}$alkoxy, cyano, trifluoromethyl, —$CO_2R^5$, —$CONR^9R^{10}$, $SO_2R^5$, or $SO_2NR^9R^{10}$;

$R^8$ is hydrogen, halogen, $C_{1-6}$alkyl, $C_{1-6}$alkoxy, cyano, trifluoromethyl, aceto, $CO_2R^5$, or $CONR^9R^{10}$;
$R^9$ and $R^{10}$ are independently hydrogen, $C_{1-6}$alkyl, —$CH_2CH_2OH$; or
$NR^9R^{10}$ taken together form pyrrolidine, piperidine, 4-hydroxypiperidine, piperazine, 4-methylpiperazine, morpholine, or thiomorpholine; and
$Ar^1$ is thiophene or phenyl substituted with 0–3 substituents selected from halogen, $C_{1-6}$alkyl, $C_{1-6}$alkoxy, cyano, trifluoromethyl, aceto, $CO_2R^5$, and $CONR^9R^{10}$;

and pharmaceutically acceptable salts and solvates of these compounds.

Another aspect of the invention are compounds which have the following 1,3,4 geometric configuration on a 5-member heterocyclic ring:

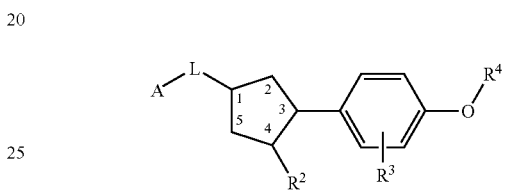

Another aspect of this invention are compounds of Formula Ia.

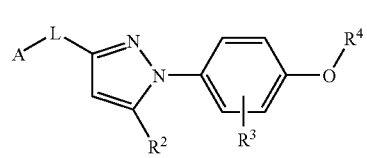

Ia

Another aspect of this invention are compounds of Formula Ib.

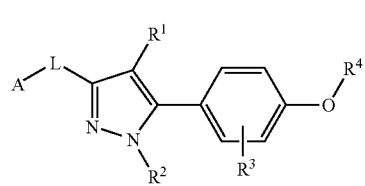

Ib

Another aspect of this invention are compounds of Formula Ic.

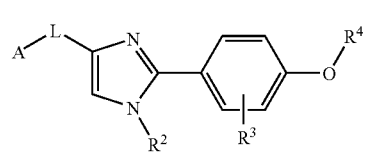

Ic

Another aspect of this invention are compounds of Formula Id.

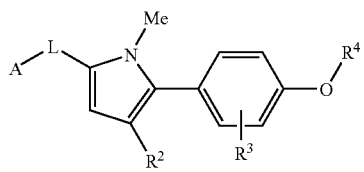

Another aspect of this invention are compounds of Formula Ie.

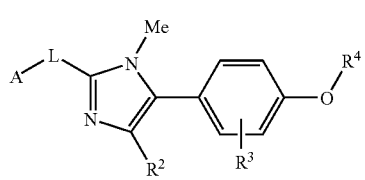

Another aspect of this invention are compounds of Formula If.

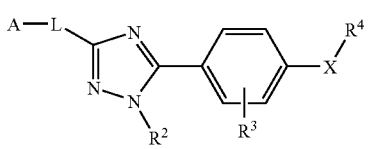

Another aspect of this invention are compounds of Formula Ig.

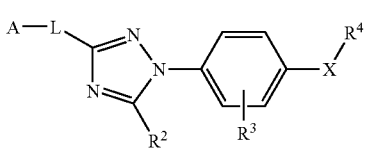

Another aspect of this invention are compounds of Formula Ih.

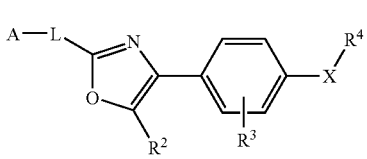

Another aspect of the invention are compounds of Formula I where A is —$CO_2R^5$.

Another aspect of the invention are compounds of Formula I where A–L is

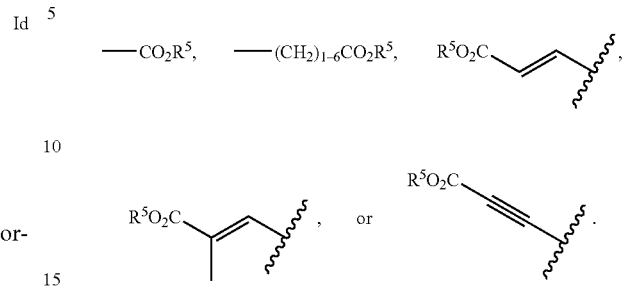

Another aspect of the invention are compounds of Formula I where $R^4$ is

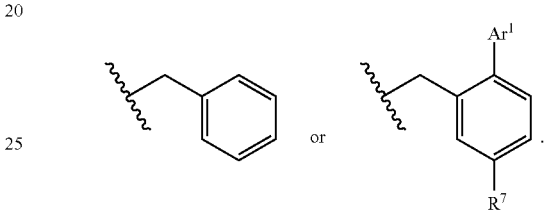

For this aspect, we note that a very broad range of substituents at $Ar^1$, including hydrogen and heteroaryl moieties, have relatively minor effect on the activity of the compounds. In contrast, activity of the compounds are enhanced when $R^7$ is a polar moiety.

Some bridged bicycloalkyl groups include bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.3.1]nonane, bicyclo[3.3.3]undecane, and adamantane.

Some compounds of the invention include the following:
(1) ethyl 1-cyclohexyl-5-(4-benzyloxyphenyl)-1H-pyrazole-3-carboxylate;
(2) methyl (2E)-3-{5-[4-(benzyloxy)phenyl]-1-cyclohexyl-1H-pyrazol-3-yl}-2-propenoate;
(3) (2E)-3-[1-cyclohexyl-5-(4-benzyloxyphenyl)-1H-pyrazol-3-yl]-2-propenoic acid;
(4) methyl (2E)-3-(5-{4-[(4'-chloro-4-methoxy-1,1'-biphenyl-2-yl)methoxy]phenyl}-1-cyclohexyl-1H-pyrazol-3-yl)-2-propenoate;
(5) (2E)-3-(5-{1-[(4'-methoxy-1,1'-biphenyl-2-yl)methoxy]phenyl}-1-cyclohexyl-1H-pyrazol-3-yl)-2-propenoic acid;
(6) ethyl (2E)-3-{5-[4-(benzyloxy)phenyl]-1-cyclohexyl-1H-pyrazol-3-yl}-2-methyl-2-propenoate;
(7) (2E)-3-{5-[4-(benzyloxy)phenyl]-1-cyclohexyl-1H-pyrazol-3-yl}-2-methyl-2-propenoic acid;
(8) ethyl (2E)-3-(5-{4-[(4'-chloro-4-methoxy-1,1'-biphenyl-2-yl)methoxy]phenyl}-1-cyclohexyl-1H-pyrazol-3-yl)-2-methyl-2-propenoate;
(9) (2E)-3-(5-{4-[(4'-chloro-4-methoxy-1,1'-biphenyl-2-yl)methoxy]phenyl}-1-cyclohexyl-1H-pyrazol-3-yl)-2-methyl-2-propenoic acid;

(10) ethyl (2E)-3-(5-{4-[(t-butyl-2-bromo-5-phenylcarboxylate)methoxy]phenyl}-1-cyclohexyl-1H-pyrazol-3-yl)-2-methyl-2-propenoate;

(11) ethyl (2E)-3-(5-{4-[(4'-chloro-4-t-butoxycarbonyl-1,1'-biphenyl-2-yl)methoxy]phenyl}-1-cyclohexyl-1H-pyrazol-3-yl)-2-methyl-2-propenoate;

(12) ethyl (2E)-3-(5-{4-[(4'-Chloro-4-N-methylcarbamoyl-1,1'-biphenyl-2-yl)methoxy]phenyl}-1-cyclohexyl-1H-pyrazol-3-yl)-2-methyl-2-propenoate;

(13) (2E)-3-(5-{4-[(4'-Chloro-4-N-methylcarbamoyl-1,1'-biphenyl-2-yl)methoxy]phenyl}-1-cyclohexyl-1H-pyrazol-3-yl)-2-methyl-2-propenoic acid;

(14) methyl 3-{5-[4-(benzyloxy)phenyl]-1-cyclohexyl-1H-pyrazol-3-yl}propanoate;

(15) 3-{5-[4-(benzyloxy)phenyl]-1-cyclohexyl-1H-pyrazol-3-yl}propanoic acid;

(16) methyl 3-(5-{4-[(4'-chloro-4-methoxy-1,1'-biphenyl-2-yl)methoxy]phenyl}-1-cyclohexyl-1H-pyrazol-3-yl)propanoate;

(17) 3-(5-{4-[(4'-chloro-4-methoxy-1,1'-biphenyl-2-yl)methoxy]phenyl}-1-cyclohexyl-1H-pyrazol-3-yl)propanoic acid;

(18) ethyl 3-{5-[4-(benzyloxy)phenyl]-1-cyclohexyl-1H-pyrazol-3-yl}-2-propynoate;

(19) 3-{5-[4-(benzyloxy)phenyl]-1-cyclohexyl-1H-pyrazol-3-yl}-2-propynoic acid;

(20) ethyl 3-(5-{4-[(4'-chloro-4-methoxy-1,1'-biphenyl-2-yl)methoxy]phenyl}-1-cyclohexyl-1H-pyrazol-3-yl)-2-propynoate;

(21) 3-(5-{4-[(4'-chloro-4-methoxy-1,1'-biphenyl-2-yl)methoxy]phenyl}-1-cyclohexyl-1H-pyrazol-3-yl)-2-propynoic acid;

(22) ethyl 5-[4-(benzyloxy)phenyl]-4-bromo-1-cyclohexyl-1H-pyrazole-3-carboxylate;

(23) methyl (2E)-3-{5-[4-(benzyloxy)phenyl]-4-bromo-1-cyclohexyl-1H-pyrazol-3-yl}-2-propenoate;

(24) (2E)-3-{5-[4-(benzyloxy)phenyl]-4-bromo-1-cyclohexyl-1H-pyrazol-3-yl}-2-propenoic acid;

(25) methyl (2E)-3-{5-[4-(benzyloxy)phenyl]-1-cyclohexyl-4-phenyl-1H-pyrazol-3-yl}-2-propenate;

(26) (2E)-3-{5-[4-(benzyloxy)phenyl]-1-cyclohexyl-4-phenyl-1H-pyrazol-3-yl}-2-propenoic acid;

(27) methyl (2E)-3-(5-{4-[4'-chloro-4-methoxy-1,1-biphenyl)methoxy]phenyl}-1-cyclohexyl-4-phenyl-5-1H-pyrazol-3-yl]-2-propenoate;

(28) (2E)-3-(5-{4-[4'-chloro-4-methoxy-1,1-biphenyl)methoxy]phenyl}-1-cyclohexyl-4-phenyl-5-1H-pyrazol-3-yl]-2-propenoic acid;

(29) ethyl 1-[4-(benzyloky)phenyl]-5-cyclohexyl-1H-pyrazole-3-carboxylate;

(30) methyl (2E)-3-{1'-[4-(benzyloxy)phenyl]-5-cyclohexyl-1H-pyrazol-3-yl}-2-propenoate;

(31) (2E)-3-{1-[4-(benzyloxy)phenyl]-5-cyclohexyl-1H-pyrazol-3-yl}-2-propenoic acid;

(32) methyl (2E)-3-(1-{4-[(4'-chloro-4-methoxy-1,1'-biphenyl-2-yl)methoxy]phenyl}-5-cyclohexyl-1H-pyrazol-3-yl)-2-propenoate;

(33) (2E)-3-(1-{4-[(4'-chloro-4-methoxy-1,1'-biphenyl-2-yl)methoxy]phenyl}-5-cyclohexyl-1H-pyrazol-3-yl)-2-propenoic acid;

(34) ethyl (2E)-3-{1-[4-(benzyloxy)phenyl]-5-cyclohexyl-1H-pyrazol-3-yl}-2-methyl-2-propenoate;

(35) (2E)-3-{1-[4-(benzyloxy)phenyl]-5-cyclohexyl-1H-pyrazol-3-yl}-2-methyl-2-propenoic acid;

(36) ethyl (2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoate;

(37) (2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoic acid;

(38) ethyl (2E)-1-[4-(4'-Chloro-4-methylcarbamoyl-biphenyl-2-ylmethoxy)-phenyl]-5-cyclohexyl-1H-pyrazol-3-yl]-2-methyl-2-propenoate;

(39) (2E)-1-[4-(4'-chloro-4-methylcarbamoyl-biphenyl-2-ylmethoxy)-phenyl]-5-cyclohexyl-1H-pyrazol-3-yl]-2-methyl-2-propenoic acid;

(40) methyl 3-{1-[4-(benzyloxy)phenyl]-5-cyclohexyl-1H-pyrazol-3-yl}propanoate;

(41) 3-{1-[4-(benzyloxy)phenyl]-5-cyclohexyl-1H-pyrazol-3-yl}propenoic acid;

(42) methyl 3-(1-{4-[(4'-chloro-4-methoxy-1,1'-biphenyl-2-yl)methoxy]phenyl}-5-cyclohexyl-1H-pyrazol-3-yl)propanoate;

(43) 3-(1-{4-[(4'-chloro-4-methoxy-1,1'-biphenyl-2-yl)methoxy]phenyl}-5-cyclohexyl-1H-pyrazol-3-yl)propanoic acid;

(44) tert-butyl (2E)-3-{2-[4-(benzyloxy)phenyl]-1-cyclohexyl-1H-imidazol-4-yl}-2-propenoate;

(45) (2E)-3-{2-[4-(benzyloxy)phenyl]-1-cyclohexyl-1H-imidazol-4-yl}-2-propenoic acid;

(46) methyl (2E)-3-{2-[4-(benzyloxy)phenyl]-1-cyclohexyl-1H-imidazol-4-yl)-2-propenoate;

(47) methyl (2E)-3-(2-{4-[(4'-chloro-4-methoxy-1,1'-biphenyl-2-yl)methoxy]phenyl}-1-cyclohexyl-1H-imidazol-4-yl)-2-propenoate;

(48) (2E)-3-(2-{4-[(4'-chloro-4-methoxy-1,1'-biphenyl-2-yl)methoxy]phenyl}-1-cyclohexyl-1H-imidazol-4-yl)-2-propenoic acid;

(49) ethyl (2E)-3-{2-[4-(benzyloxy)phenyl]-1-cyclohexyl-1H-imidazol-4-yl}-2-methyl-2-propenoate;

(50) (2E)-3-(2-[4-(benzyloxy)phenyl]-1-cyclohexyl-1H-imidazol-4-yl}-2-methyl-2-propenoic acid;

(51) ethyl (2E)-3-(2-{4-[(4'-chloro-4-methoxy-1,1'-biphenyl-2-yl)methoxy]phenyl}-1-cyclohexyl-1H-imidazol-4-yl)-2-methyl-2-propenoate;

(52) (2E)-3-(2-{4-[(4'-chloro-4-methoxy-1,1'-biphenyl-2-yl)methoxy]phenyl}-1-cyclohexyl-1H-imidazol-4-yl)-2-methyl-2-propenoic acid;

(53) t-Butoxy (2E)-3-(2-{4-[(4'-chloro-4-N-methylcarbamoyl-1,1'-biphenyl-2-yl)methoxy]phenyl}-1-cyclohexyl-1H-imidazol-4-yl)-2-methyl-2-propenoate; and

(54) (2E)-3-(2-{4-[(4'-chloro-4-N-methylcarbamoyl-1,1'-biphenyl-2-yl)methoxy]phenyl}-1-cyclohexyl-1H-imidazol-4-yl)-2-methyl-2-propenoic acid.

"Aryl" includes both carbocyclic and heterocyclic aromatic ring systems. "Het" means a heteroaryl ring. "Alkyl" and "alkoxy" include straight and branched confugurations. The term "halogen" includes fluorine, chlorine, bromine, and iodine.

The invention includes all pharmaceutically acceptable salt forms of the instant compounds. Pharmaceutically acceptable salts are those in which the counter ions do not contribute significantly to the physiological activity or toxicity of the compounds and as such function as pharmacological equivalents. In many instances, salts have physical properties that make them desirable, such as solubility or crystallinity. The salts can be made according to common organic techniques employing commercially available reagents. Suitable anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Suitable cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds. Solvate forms do not contribute significantly to the physiological activity or toxicity of the compounds and as such function as pharmacological equivalents. Solvates may form in stoichiometric amounts or may form with adventitious solvent or a combination of both. One type of solvate is hydrate and some hydrated forms include monohydrate, hemihydrate, and dihydrate, but other forms can be encountered.

Synthesis

The novel compounds of this invention can be prepared using reactions and techniques described in this section or known in the art. The starting materials are commercially available or can be prepared by methods known in the art. Reactions are performed in solvents appropriate to the reagents and materials employed.

Synthetic routes to carboxylate acids and esters depicted below can be adapted by methods known to one skilled in the art to allow for the preparation of nitriles, halogens, or sulphonate esters, or other functional groups that may be converted to carboxylate isosteres by various methods. These substituents may be interconverted as necessary by a wide variety of methods known to one skilled in the art of organic synthesis.

Scheme 1 describes the synthesis of 1-cycloalkylpyrazoles and begins with the conversion of protected 4-hydroxyphenyl methyl ketones (1.1) to diketoesters 1.2. This intermediate can be condensed with a cycloalkyl-substituted hydrazines to afford pyrazoles 1.3. Thus, substituents $R^1$ and $R^2$ and $R^3$ can be varied by the choice of starting materials, and if $R^3$ is initially H, then it can be replaced by bromine via a bromination reaction, and further modified via Pd° coupling or metal-halogen exchange followed by reaction with an appropriate electrophile.

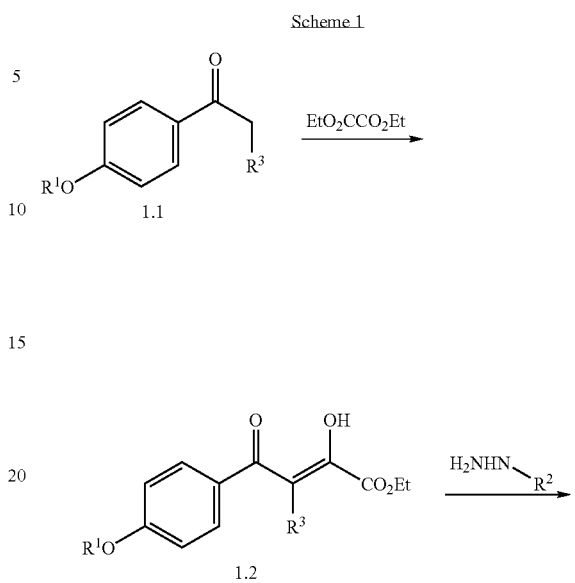

Scheme 2 depicts elaboration to α,β-unsaturated carboxylates beginning from esters 1.3 of Scheme 1. Reduction to alcohols 2.1 followed by oxidation can give aldehydes 2.2 which can then be coupled with an appropriate Wittig or equivalent reagent to provide the α,β-unsaturated esters 2.3. Saponification of 2.3 can provide carboxylic acids 2.4. It is envisioned that aldehydes 2.2 can be coupled with olefination reagents to provide α,β-unsaturated sulfonate esters, nitriles, or other intermediates that can be converted to carboxylate isosteres.

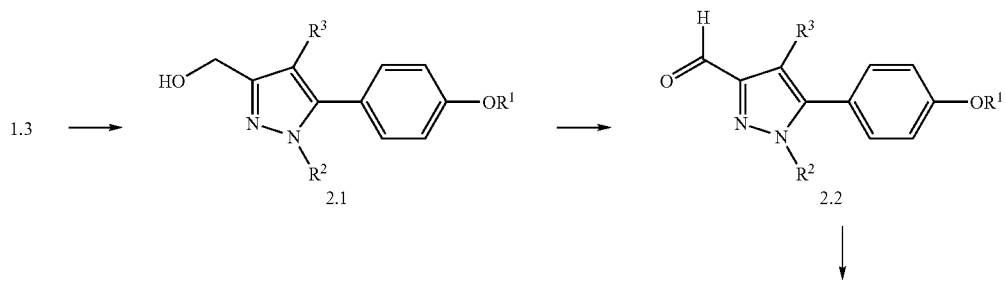

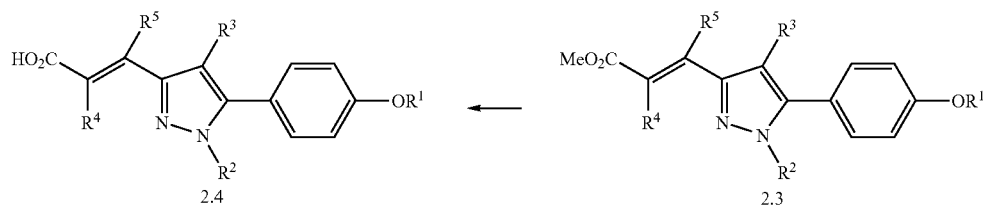

Preparation of biphenyl sidechain analogs as drawn in Scheme 3 requires removal of $R^1$ from 2.3 to liberate phenols 3.1. Alkylation 3.1 can give biphenyl analogs 3.2 which can be hydrolyzed at the methyl ester to provide compounds 3.3. Substituents $R^4$ and $R^5$ can be varied by choice of reagent.

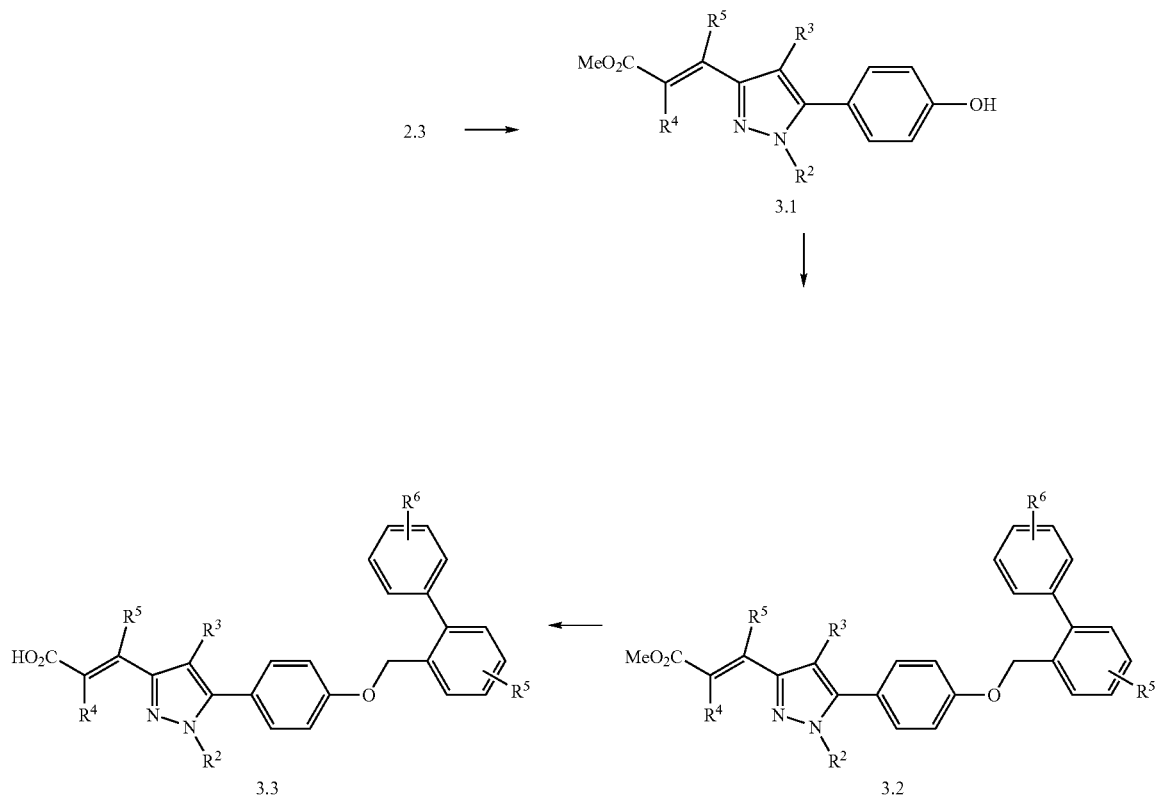

In Scheme 4, reaction of aldehyde analogs 2.2 with a Wittig like reagent can give methyl substituted analogs of structure 4.1, and hydroylsis of 4.1 can give carboxylic acids 4.2. Alternatively, deprotection (removal of $R^1$ from 4.1) can give phenols 4.3, and alkylation of the phenols can provide biphenyl analogs 4.4 which can be further subjected to ester saponification to arrive at carboxylic acids 4.5 possessing HCV inhibitory activity.

Scheme 4
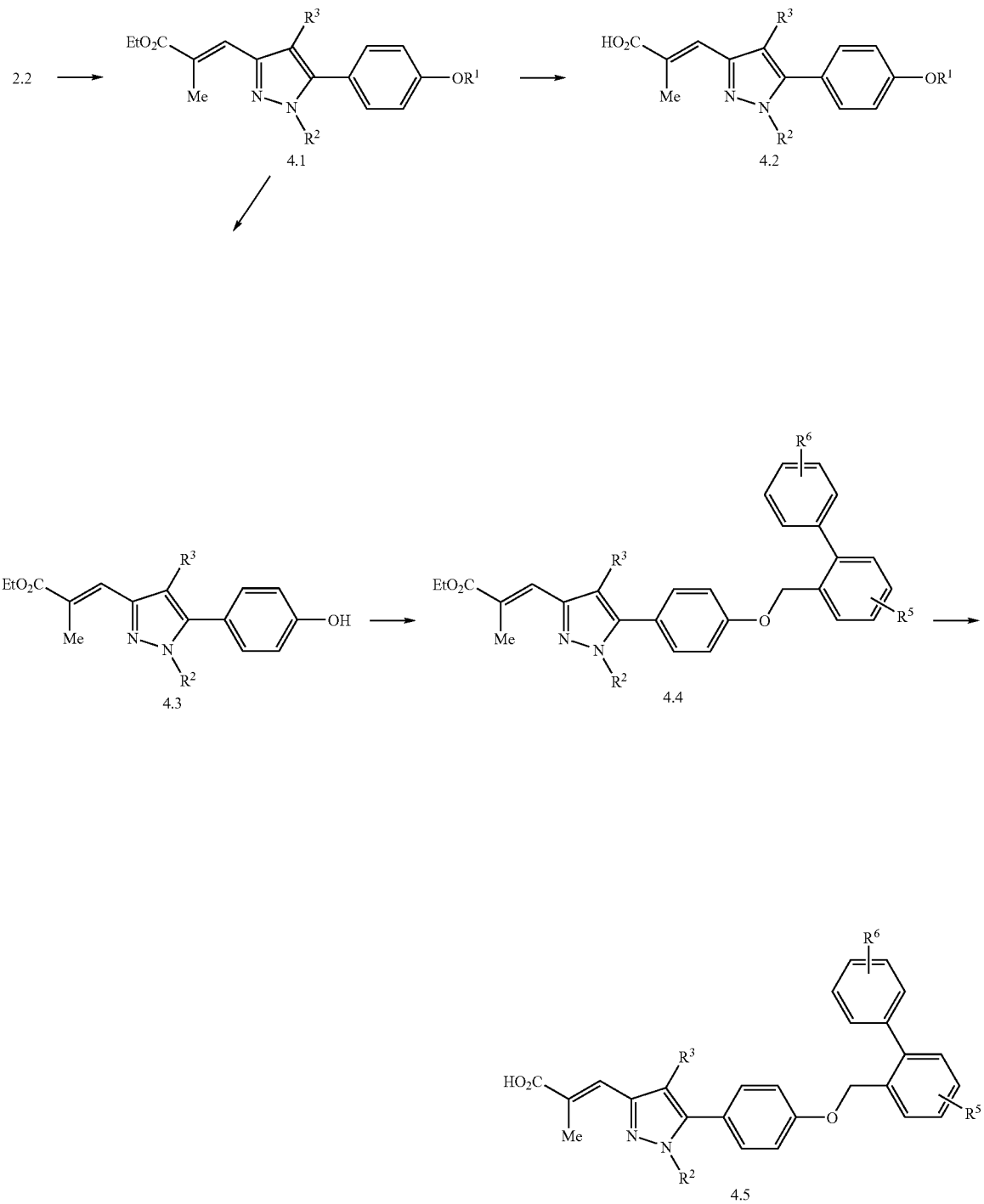
As outlined in Scheme 5, compounds of structure 4.3 can be alkylated to give bromide analogs 5.1. Theses analogs can be derivatized via coupling chemistry to biphenyl structures 5.2. Cleavage of the tert-butyl ester can give carboxylates 5.3 which can be coupled with amines to form amides 5.4. Saponification of the ethyl ester can give carboxylates 5.5.

Scheme 5
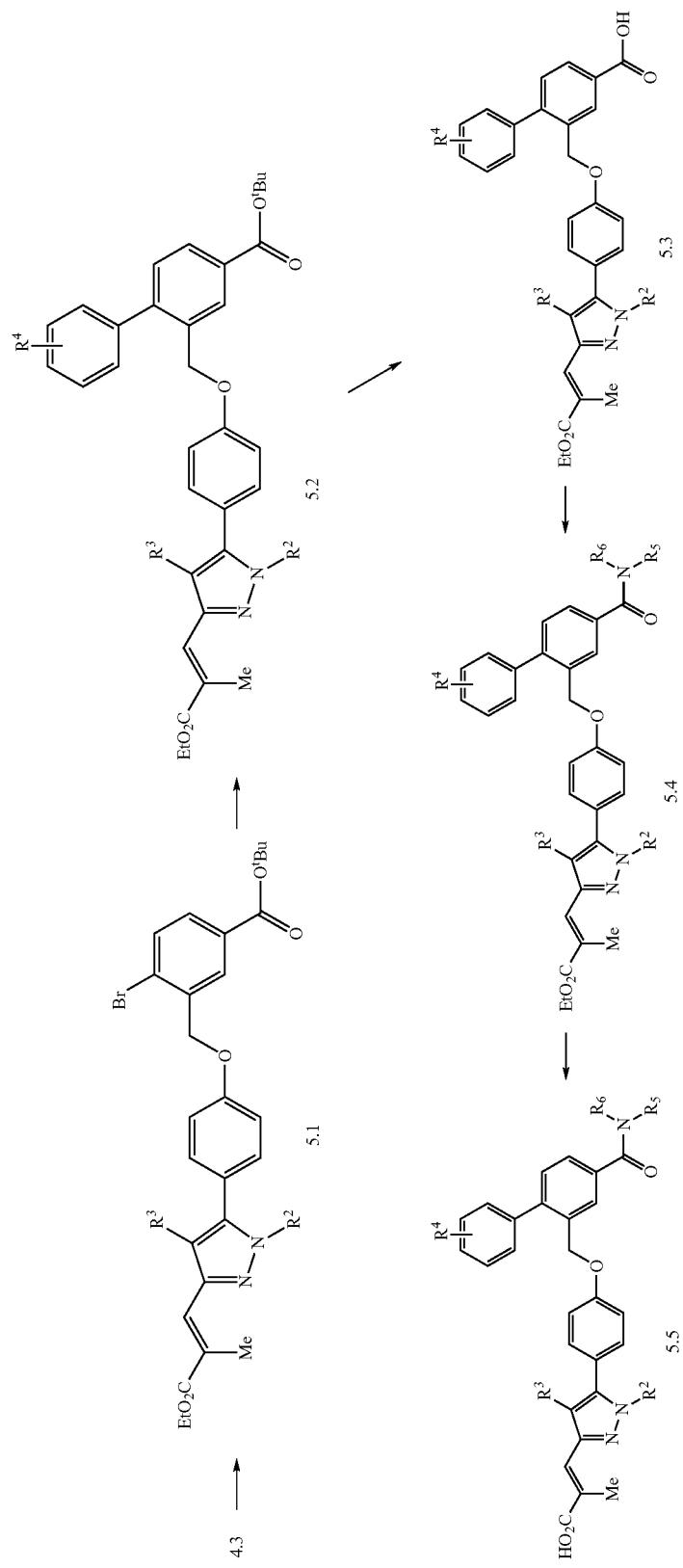

The olefinic double can be reduced to give saturated compounds of scheme 6. Hydrogenation of methyl esters 2.3 can provide propanoates 6.1, and propanoic acids 6.2 after saponification. Following the sequence of Scheme 3, phenols 6.3 can be obtained upon deprotection of 6.1, and alkylation of 6.3 as above can give biphenyl analogs 6.4. A further step of hyrolysis can give carboxylic acid compounds 6.5.

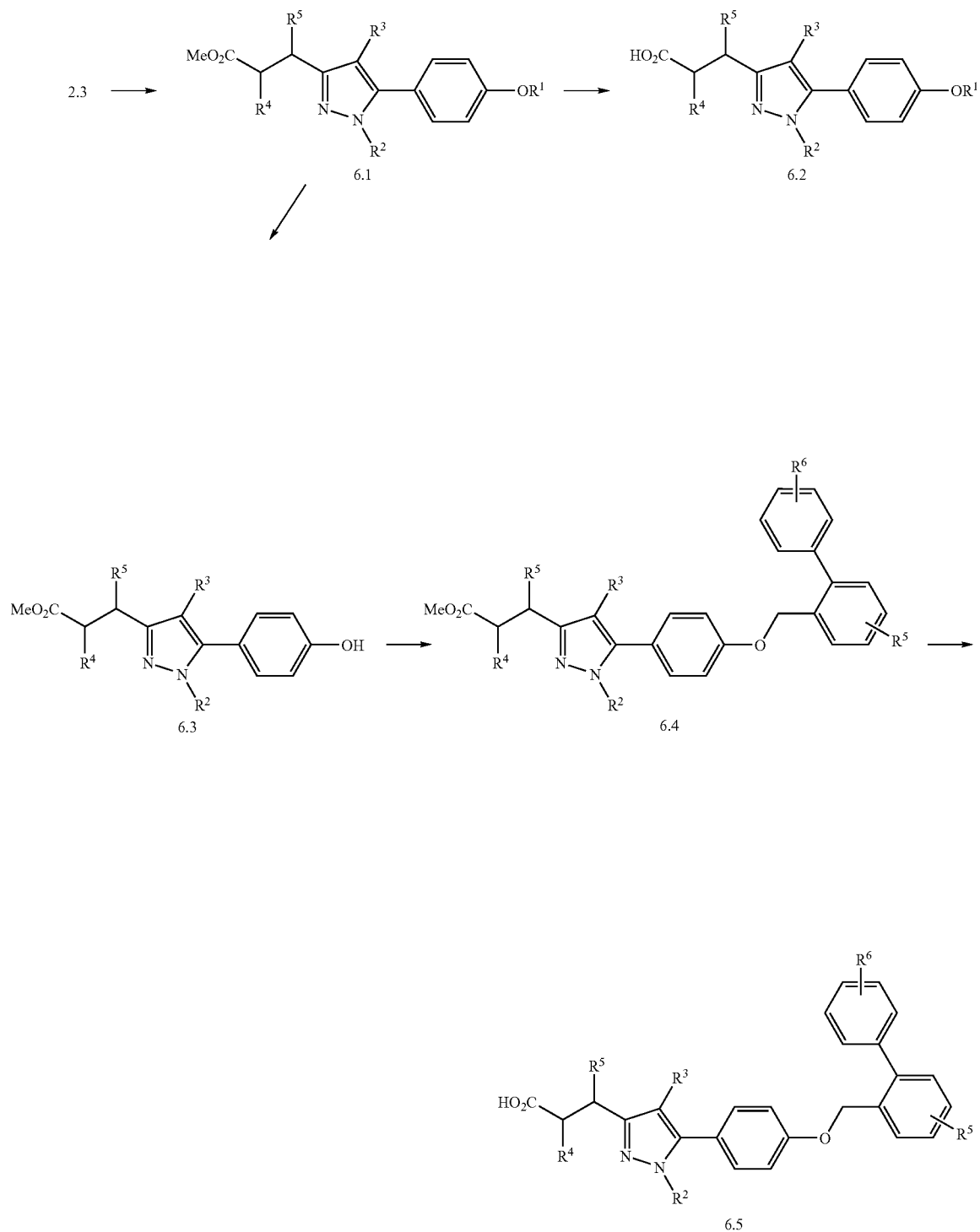

Scheme 7 depicts the synthetic entry into an alkynyl series of biphenyl analogs. The reaction of carbon tetrabromide and triphenylphosphene on aldehyde 2.2 can give vinyl dibromides 7.1, which upon subjection to butyl lithium can afford acetylenes 7.2. Deprotonation and quench with chloroformate can provide ethyl esters 7.3 which can be hydrolyzed to 7.4. Alternatively, deprotection of 7.3 yields phenols 7.5 which can be further subjected to alkylation, and the resulting biphenyl analogs 7.6 can be saponified to carboxylic acid compounds 7.7.

Scheme 8 outlines bromination of pyrazoles 1.3 to give bromides 8.1 which can be used to obtain pyrazoles substituted at the 4-postion. Thus, 8.1 can be reduced to alcohols 8.2, oxidized to aldehydes 8.3, treated with Wittig reagent to afford propenoates 8.4, and saponified to 8.5 according to methods above. Bromides 8.4 can be coupled with phenyl boronic acids to give rise to 4-phenyl analogs 8.6, saponification of which leads to acids 8.7, or removal of $R^1$ can give phenols 8.8. As above, alkylation of the phenol can give biphenyls 8.9, and saponification can provide carboxylates 8.10.

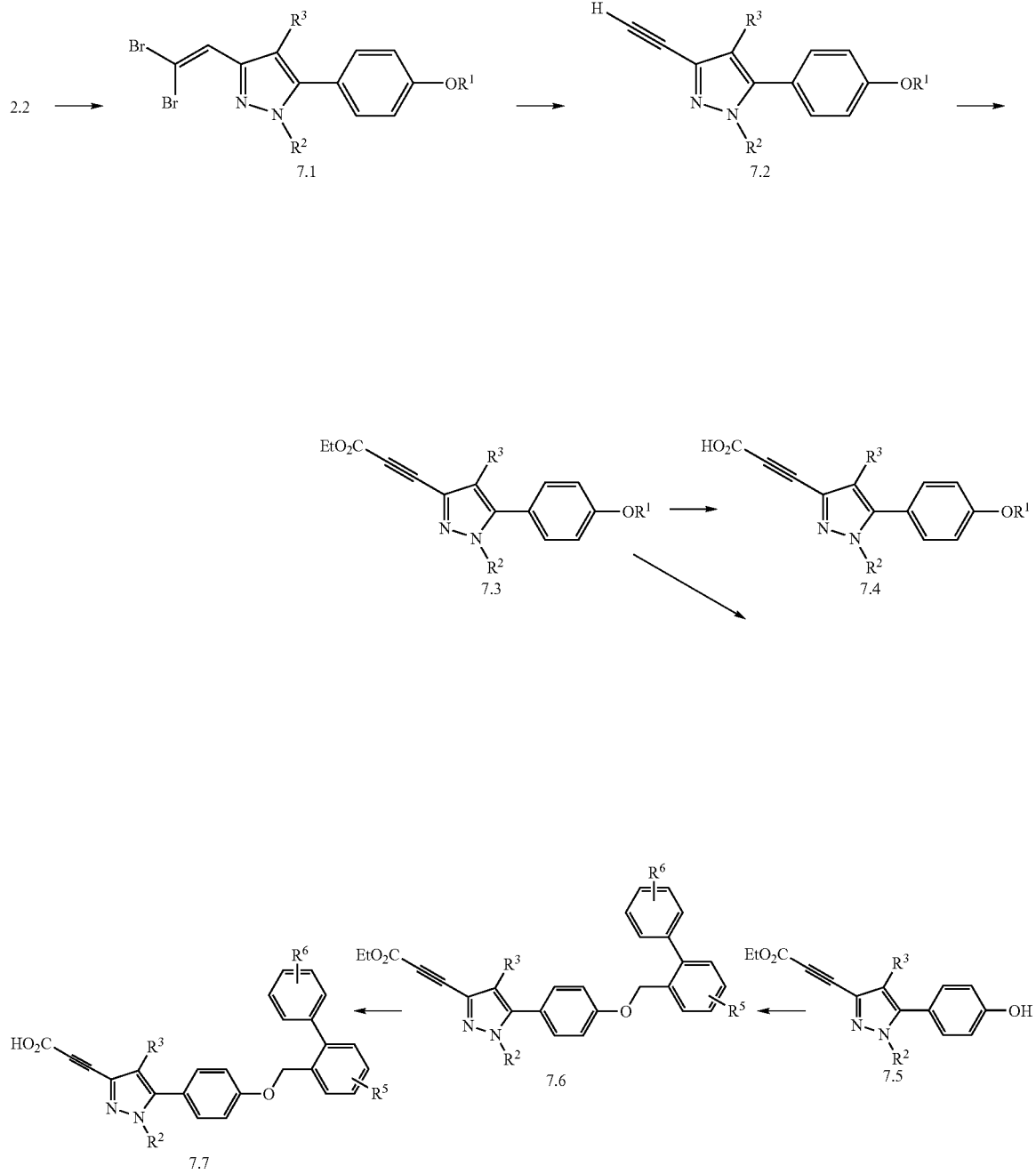

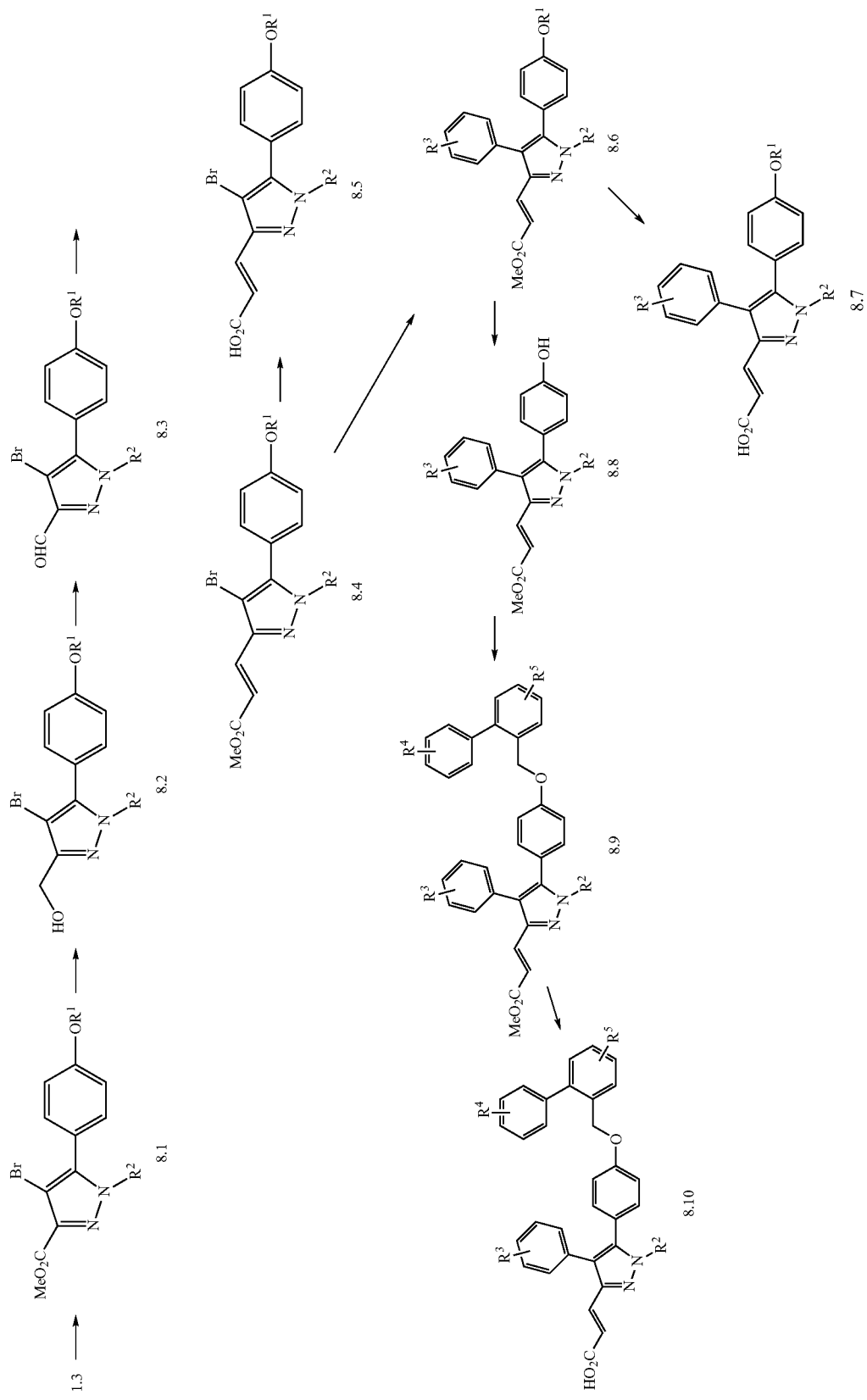

Scheme 9 depicts preparation of another type of compound, 5-cycloalkylpyrazole derivatives. Diketoesters 9.1 can be obtained upon treatment of cycloalkyl methyl ketones with ethyl oxalate, and can be subsequently condensed with substituted phenylhydrazines to give 5-cycloalkylpyrazoles 9.2. Substituents $R^1$, $R^2$, and $R^3$ can be varied by the choice of starting materials. If substituent $R^2$ is H, then bromine can be introduced via bromination with $Br_2$ in acetic acid, followed by further modification of the bromo substituent via Pd° coupling or other derivation known to those skilled in the art. As above, reduction of 9.2 to alcohols 9.3, oxidation of 9.3 to aldehydes 9.4, and Wittig reaction to 9.5 can give compounds suitable for further elaboration to biphenyl derivatives. While saponification of esters 9.5 can give acids 9.6, deprotection of 9.5 (removal of $R^3$) can provide 9.7 which can be alkylated to biphenyls 9.8, and further saponification can yield carboxylates 9.9.

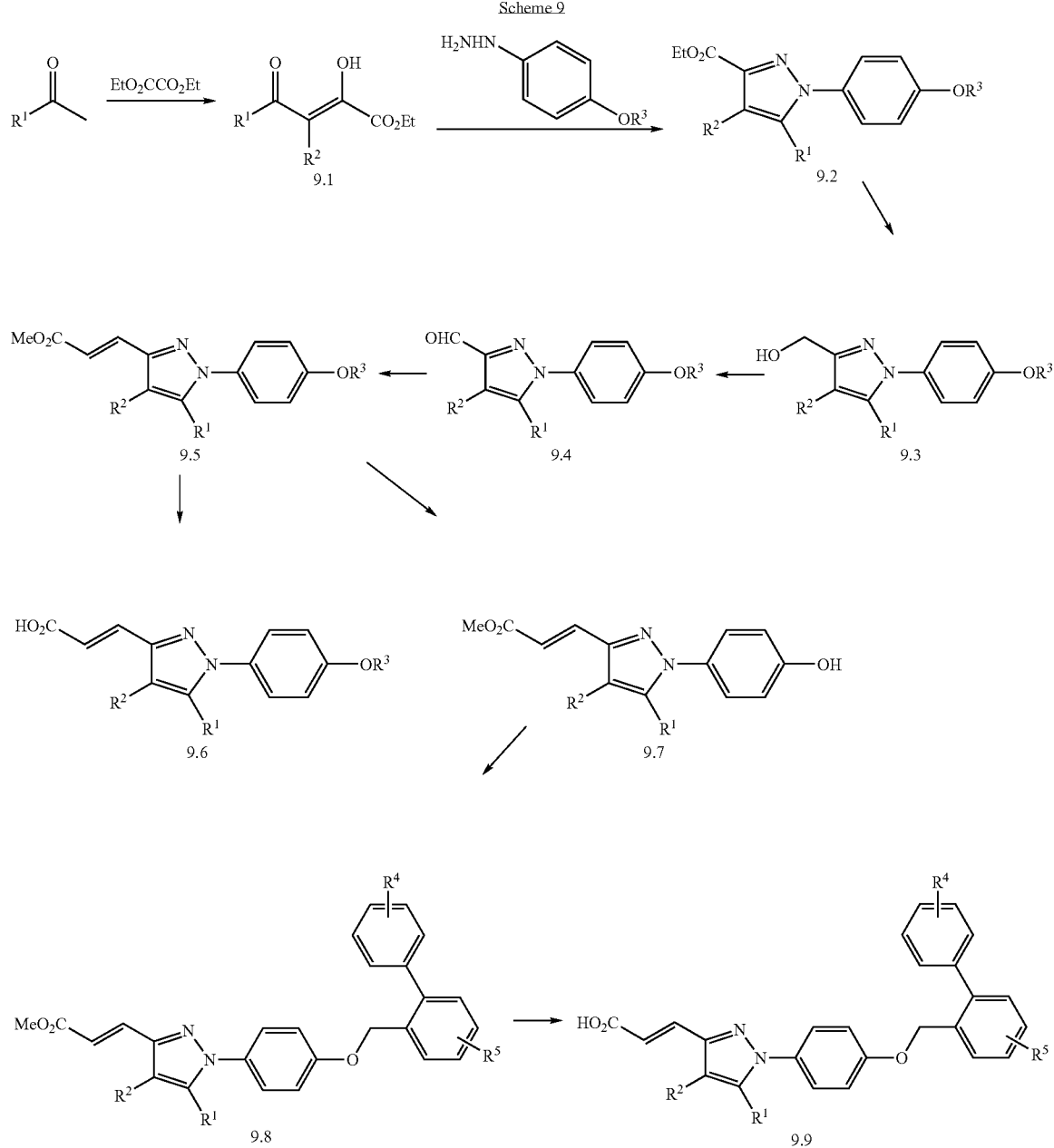

Scheme 9

In a similar sequence to Schemes 4 and 5, aldehydes 9.4 can be carried forward (Scheme 10) to give biphenylamides. Thus, exposure to Wittig conditions can afford 2-methyl-propenaotes 10.1 which can be saponified to acids 10.2. Alternatively, 10.1 can be deprotected (removal of $R^3$) to generate phenols 10.3 which can be alkylated to give biphenyl amides 10.4, and further saponification provides carboxylic acids 10.5.

Scheme 10
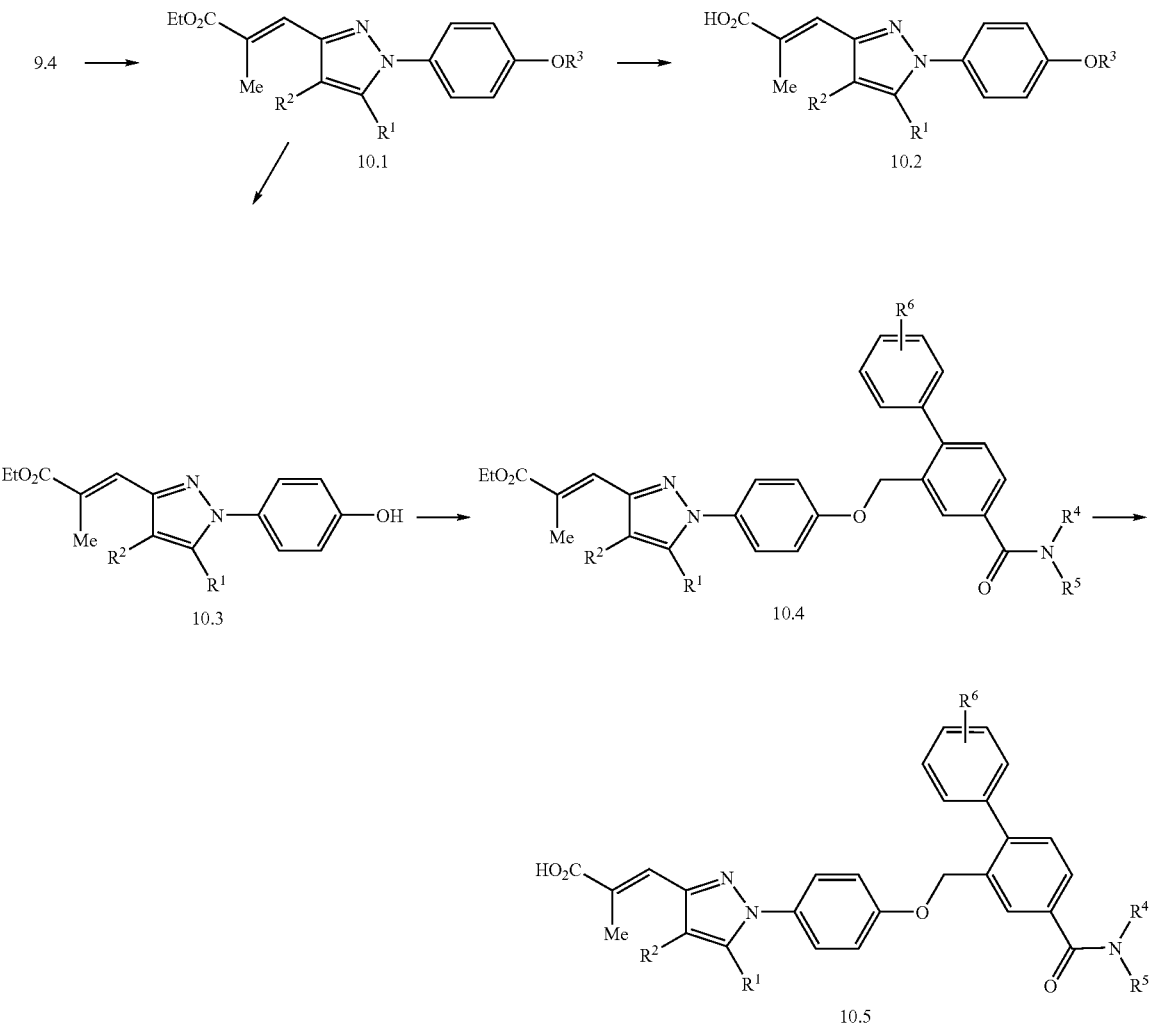
In similar manner to Scheme 6, propenoates 9.5 can be reduced to give saturated compounds 11.1 shown in Scheme 11. Saponification can provide carboxylic acids 11.2, and removal of $R^3$ gives phenols 11.3. Alkylation to biphenyl derivatives 11.4 and hydrolysis of 11.4 provides propanoic acids analogs 11.5.
Scheme 11
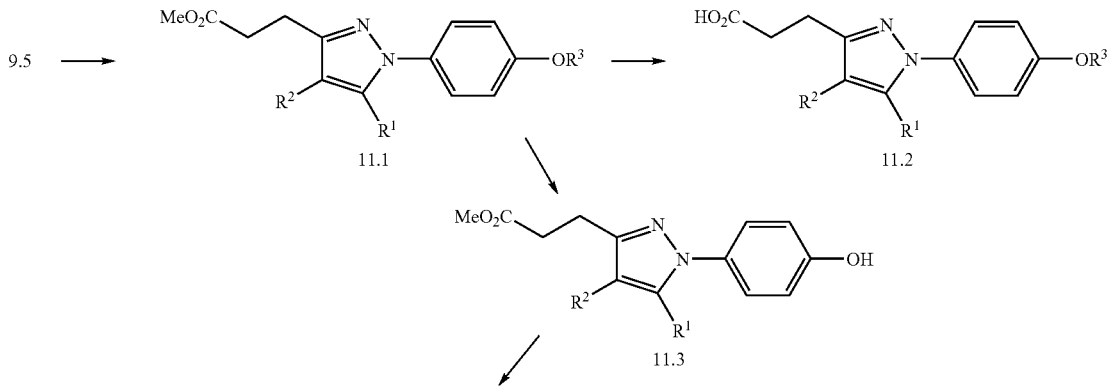

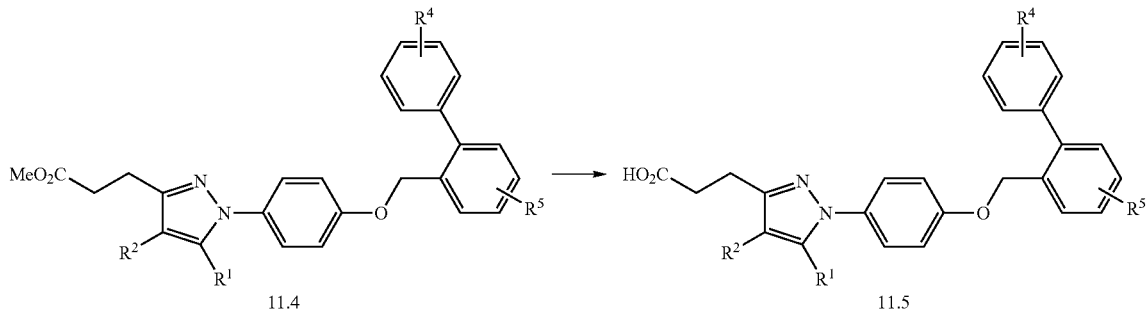

Cycloalkylimidazole derivatives are depicted in scheme 12. Cycloalkylimdazoles 12.1 can be brominated to tribromide 12.2. Coupling at the 2-position can give 12.3 which can be selectively debrominated to 12.4, and coupled at the 4-position to give 12.5 which can be saponified to generate carboxylates 12.6. Alternatively, transmetalation of 12.4 and quench with DMF can give aldehydes 12.7. Wittig olefination of 12.7 can afford α,β-unsaturated esters 12.8 which can be deprotected (removal of R²) to yield phenols 12.9. Alkylation of 12.9 and saponification of the resulting biphenyl analogs can give 12.10 and 12.11, respectively.

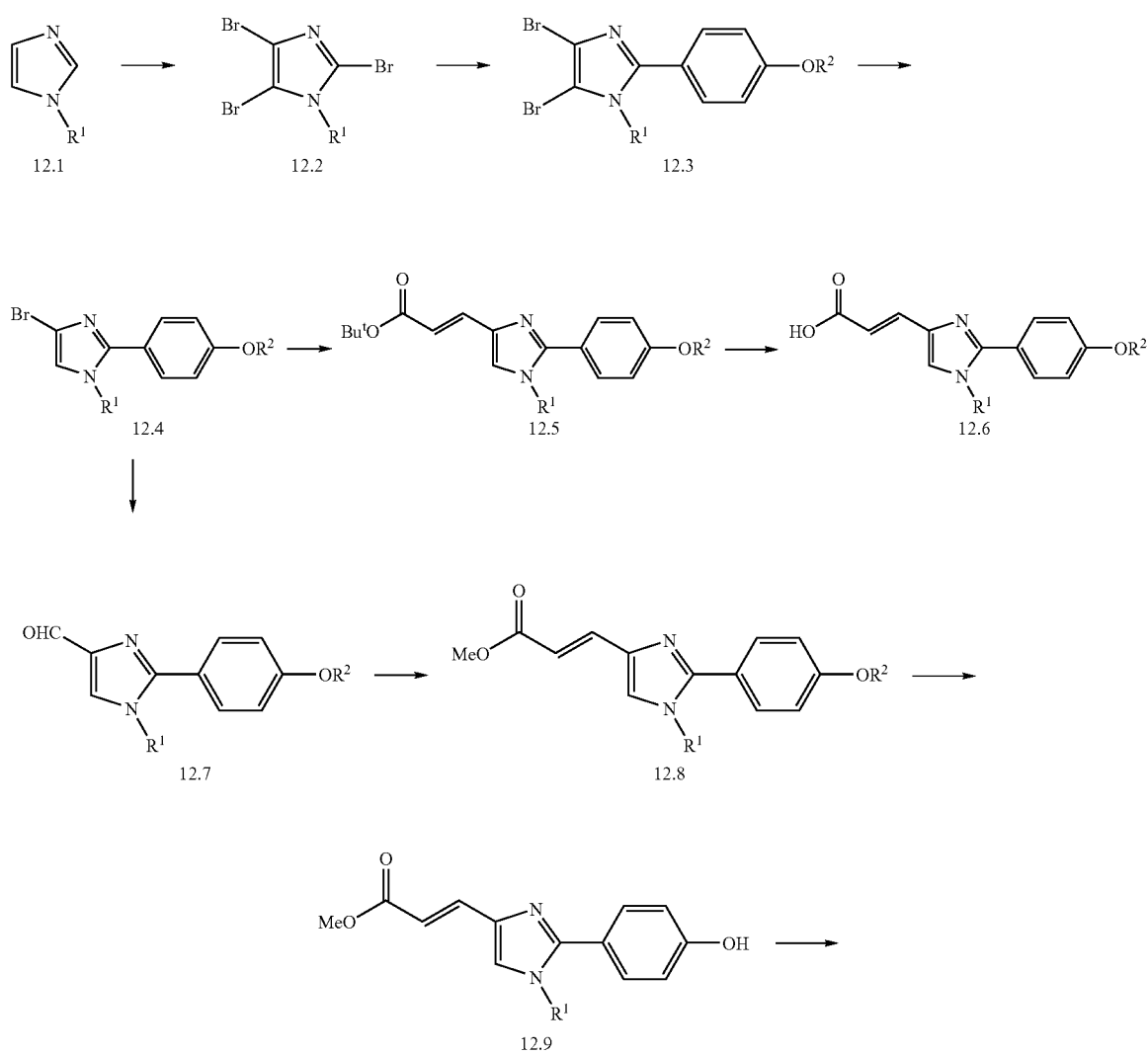

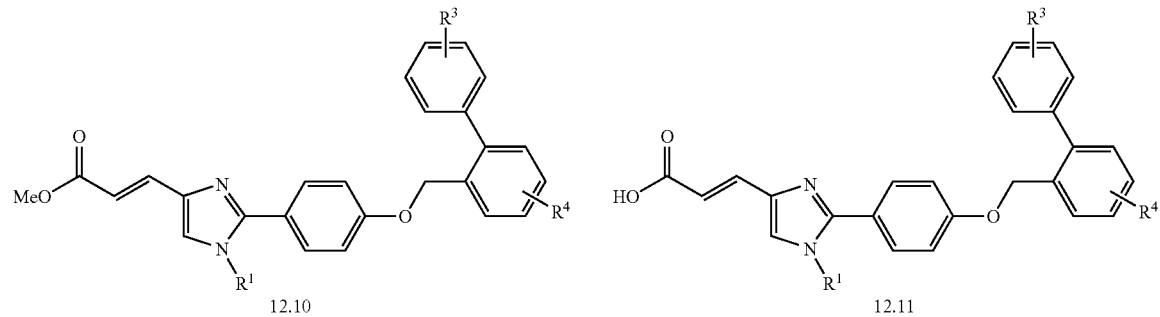
12.10
12.11
As depicted above in schemes 4 and 10, a similar sequence is defined in scheme 13 for 2-methyl substitution on the propenoate sidechain. Thus, aldehydes 12.7 can be treated with Wittig-like reagents to provide derivatives 13.1, which can be saponified to 13.2, or deprotected to phenols 13.3. Alklation of phenols can give biphenyls 13.4, and saponification can give carboxylates 13.5.
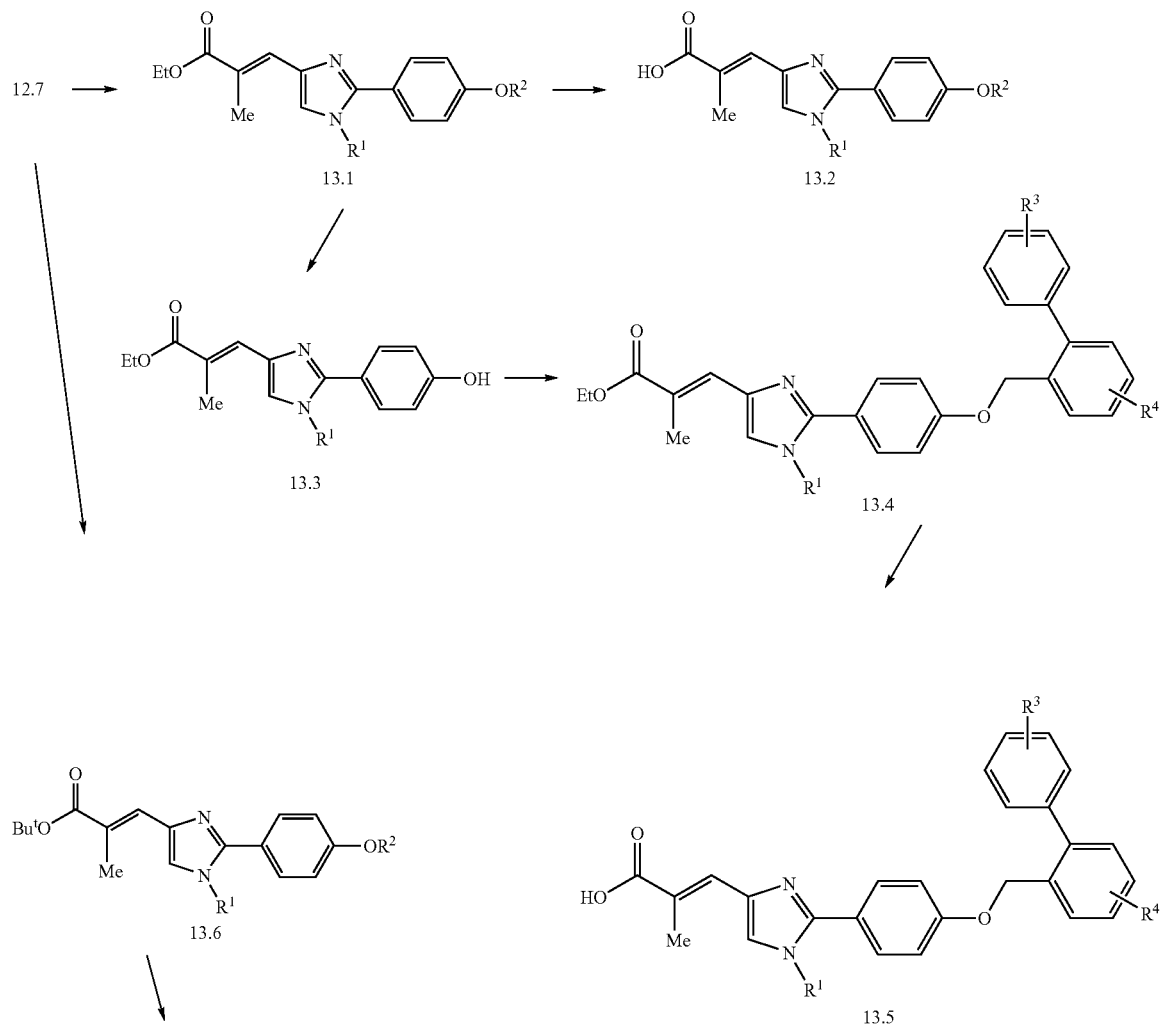
Scheme 13

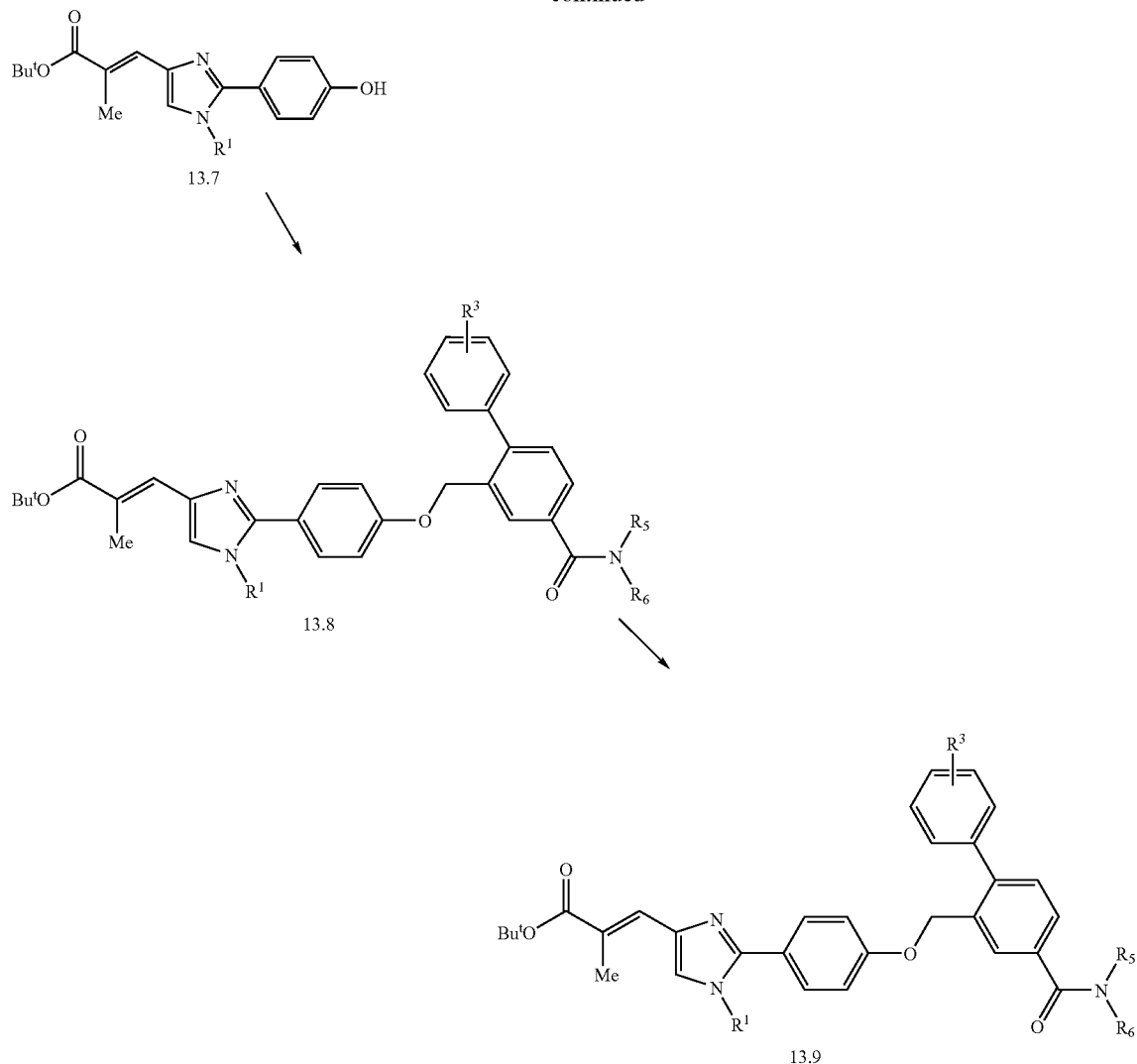

Carboxylate isostere groups can be incorporated into the compounds of this invention. The heterocycles prepared in schemes 1–13 each bear a carboxylic acid liberated through hydrolysis in the final step of the synthesis. The carboxylic acid can be replaced with an equivalent group or isostere introduced in the final step of synthesis, or during synthesis of precursors to the final compound. In schemes 14–19, only the carboxylate isostere and its attached carbon atom are explicitly shown, however, they can be incorporated into the heterocycles of this invention by methods known in the art of synthetic organic chemistry.

Scheme 14 illustrates the synthesis of tetrazole derivatives. For a leading reference, see: Duncia, J. V., et al. *J. Org. Chem.* (1991), 56, 2395–2400; Herr, J. R. *Bioorg. & Med. Chem.* (2002), 10, 3379–3393. Nitrile 14.1 can be reacted with a trialkyltin azide, optionally prepared in situ from a trialykltin chloride and metal azide, in a solvent such as toluene at elevated temperature to afford tetrazole 14.2. The trialkyltin moiety can be removed by treatment with hydrogen chloride to afford the deprotected tetrazole 14.3. As an alternative, nitrile 14.1 can be converted directly to tetrazole 14.3 by treatment with sodium azide and ammonium chloride (or trialkylammonium hydrochloride, in an aromatic solvent: Koguro, K. et al. *Synthesis* (1998), 910–914) in a solvent such as DMF at elevated temperature. Another approach, where R1 is a carboxylic acid, the acid 14.4 can be coupled to 3-aminopropionitrile using DCC in dichloromethane. Treatment of the resulting amide 14.5 with sodium azide under Mitsonobu conditions can afford the tetrazole 14.6, which may be deprotected by a variety of basic reagents to provide the deprotected tetrazole 14.3.

Scheme 14

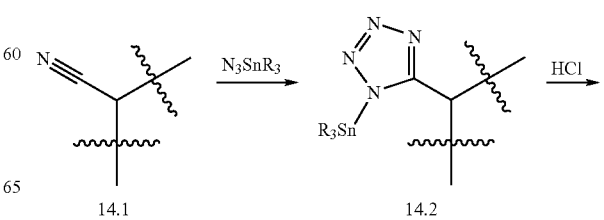

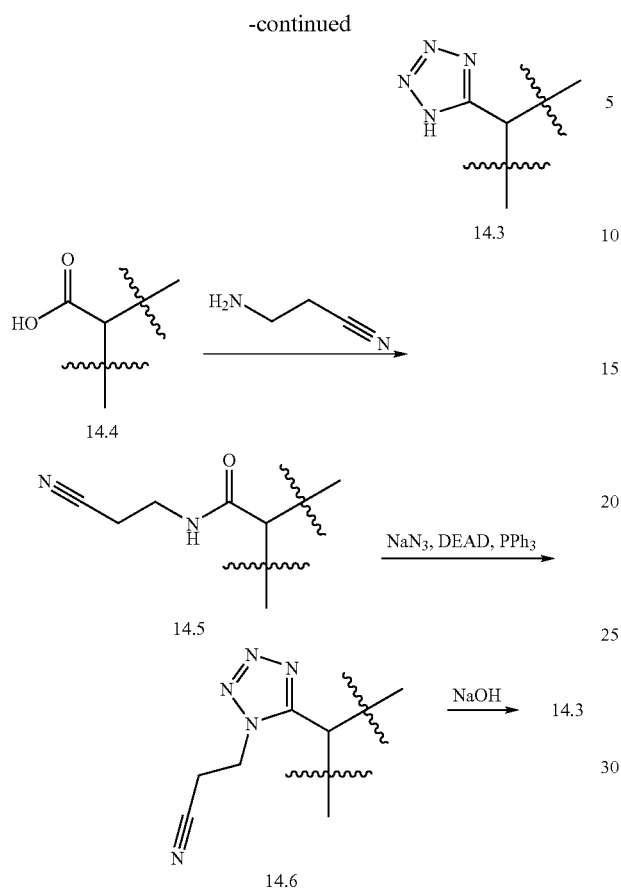

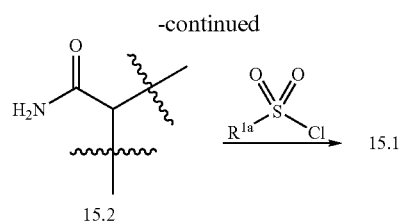

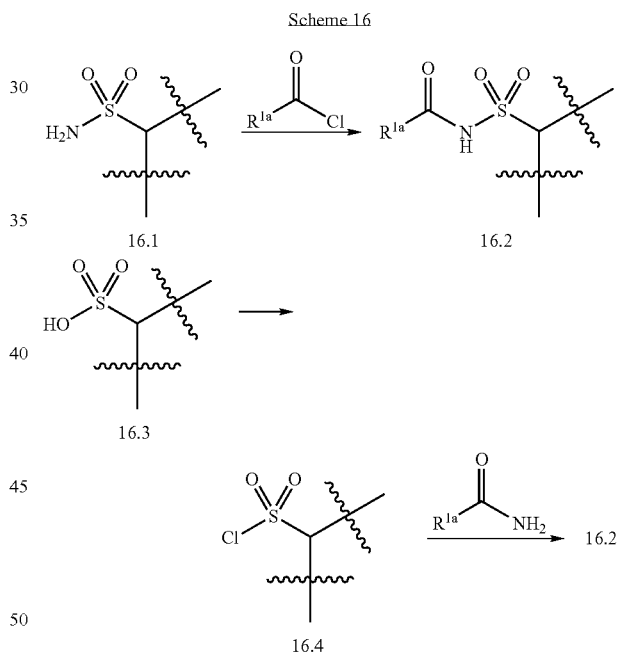

Scheme 15 depicts the synthesis of acylsulfonamide derivatives from carboxylic acids and primary carboxamides. Carboxylic acid 14.4 can be treated with a sulfonamide and a coupling agent, 1-(3-dimethylaminopropyl-3-ethylcarbodiimide (EDC), and DMAP (Sturino, C. F., et al. *Tetrahedron Lett.* (1998), 39, 5891–5894) to generate acylsulfonamide 15.1. Other conditions include formation of a carbonylimidazolide by treatment of 14.4 with carbonyl diimidazole (CDI), followed by a sulfonamide and DBU (Drummond, J. T.; Johnson, G. *Tetrahedron Lett.* (1988), 27, 1653–1656), or formation of an acid chloride by treatment of 14.4 with thionyl chloride, followed by reaction with the sodium salt of a sulfonamide in DMF/dichloromethane. Alternatively, compound 15.1 can be prepared by reaction of primary amide 15.2 with an appropriate sulfonyl chloride in a solvent such as pyridine at elevated temperature (Cossu, S.; Giacomelli, G.; Conti, S.; Falorni, M.; *Tetrahedron* (1994), 50, 5083–5090).

Scheme 15

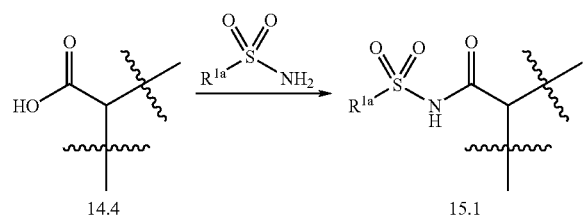

The synthesis of acylsulfonamide compounds from primary sulfonamides or sulfonic acids is shown in scheme 16 where compound 16.1 can be converted to an acylsulfonamide 16.2 upon reaction with an acid chloride and DMAP in pyridine or with an isocyanate (Mantlo, N. B. et al. *Bioorg. Med. Chem. Lett.* (1994), 4, 17–22). Moreover, sulfonic acid 16.3 can be converted to sulfonyl chloride 16.4 by treatment with phosphorous oxychloride, phosphorous pentachloride, or a mixture of the two, or with thionyl chloride, in a solvent such as benzene, toluene, or DMF. Addition of a primary amide to chloride 16.4 is facilitated by DMAP in pyridine at elevated temperature to provide another entry into acylsulfonamides 16.2.

Scheme 16

Hydroxylamine can be added to nitrile 14.1 to form amidoxime 17.1 in solvents such as EtOH, DMF, or DMSO at elevated temperature as outlined in scheme 17. Amidoxime 17.1 can be further cyclized to 5-oxo-1,2,4-oxadiazole 17.2 when treated with methylchloroformate and a base reagent such as pyridine, followed by reflux in toluene (Kohara, Y. et al. *Bioorg. Med. Chem. Lett.* (1995), 5, 1903–1908). Alternatively, 17.1 can form oxathiadiazole 17.3 in the presence of $SOCl_2$ in pyridine (Kim, D. et al. *Bioorg. Med. Chem. Lett.* (1994), 4, 41–44). And, in a similar way amidoxime 17.1 can be converted to oxadiazole 17.4 when reacted with thiocarbonyldiimidazole and DBU in acetonitrile (Gezginci, et al. *J. Med. Chem.* (2001), 44, 1560–1563).

Scheme 17

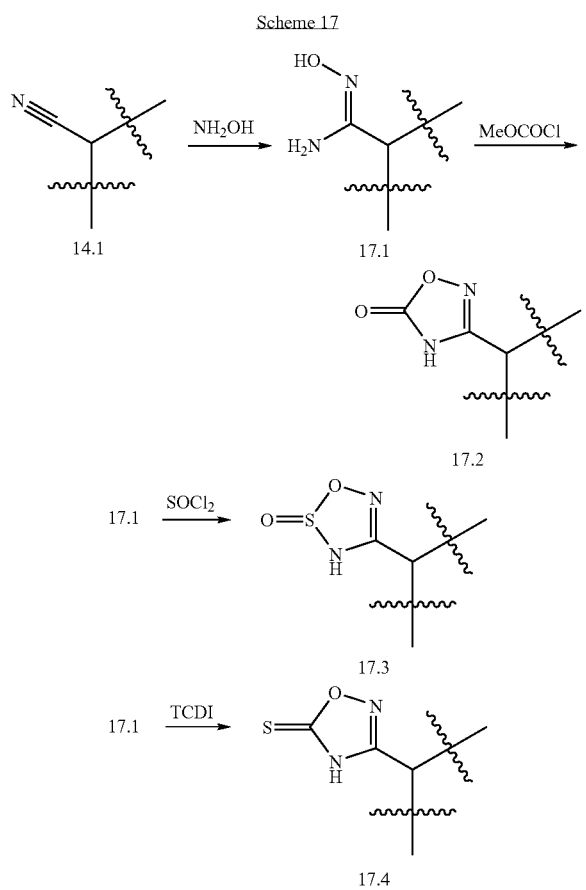

Scheme 18 depicts synthesis of 3-hydroxy-3-cyclobutene-1,2-dione compounds from iodide 18.1 which can be coupled to stannyl cyclobutene 18.2 (Soll, R. M. et al. *Bioorg. Med. Chem. Lett.* (1993), 3, 757–760) using catalytic trans-benzyl(chloro)bis(triphenyl phosphine)palladium (II) and copper(I) iodide in acetonitrile at elevated temperature (Liebskind, L. S.; Fengl, R. W. *J. Org. Chem.* (1990), 55, 5359) to afford compound 18.3, and acidic hydrolysis can provide 3-hydroxy-3-cyclobutene-1,2-dione 18.4.

Scheme 18

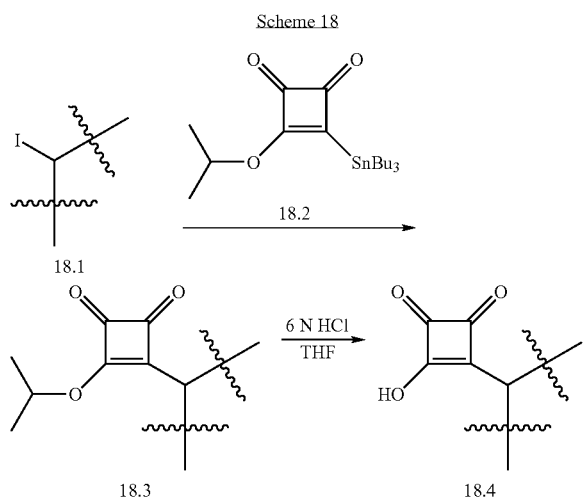

Carboxylic acid 14.4 can be coupled with 5-aminomethyltetrazole 19.1 (available commercially from Dynamit Nobel GmbH, Leverkusen, Germany) using any of a variety of peptide coupling reagents, including EDC and 1-hydroxybenzotriazole in dichloromethane or DMF, to give 1H-tetraazol-5-ylmethyl carboxamide 19.2. Under similar reaction conditions, 14.4 can be coupled with 5-aminotetrazole 19.3 to afford 1H-tetraazol-5-yl carboxamide 19.4.

Scheme 19

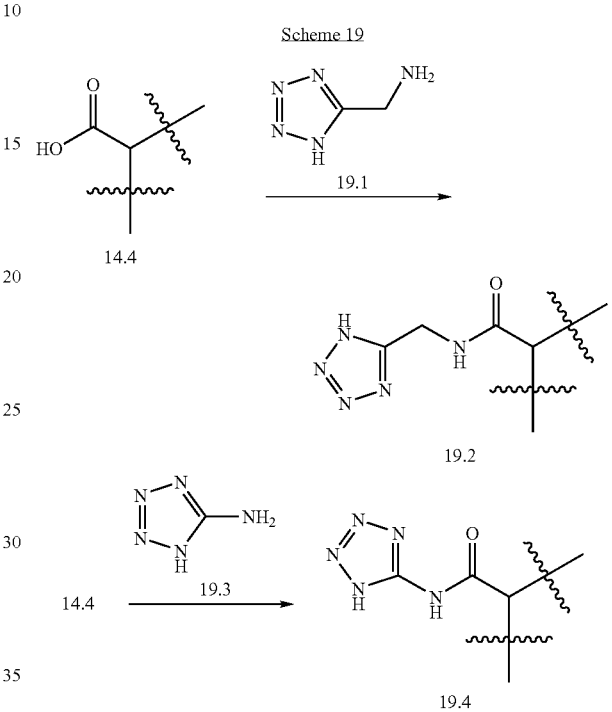

Other carboxylate isosteres claimed in the present invention can be synthesized by methods known to one skilled in the art of organic synthesis. For example, preparation of phosphinic and phosphonic acid analogs (Kehler, J. et al. *Bioorg. Med. Chem. Lett.* (2000), 10, 2547–2548), hydroxamic acids (Golebiowski *Tet. Lett.* (1998), 39, 3397), etc.

Biological Activity

Compounds of Formula I inhibit the activity of Hepatitis C Virus NS5B RdRp as demonstrated using assays measuring NS5B RdRp activity.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 ug/ml and the cells were grown overnight at 20° C.

Cell pellets (3L) were lysed for purification to yield 15–24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5–50 column volumes depending on the column type. After the final chromatography step, the resulting purity of the enzyme is >90% based on SDS-PAGE analysis. The enzyme was aliquoted and stored at −80° C.

HCV NS5B RdRp enzyme assay. HCV RdRp genotype 1b assays were run in assay buffer composed of 20 mM Tris-HCl, pH 7.5, 2.5 mM KCl, 5 mM $MgCl_2$, 1 mM DTT, 1.6 U RNAse inhibitor (Promega N2515), in 96 well plates (Falcon 3918). All compounds were serially diluted in DMSO and diluted further in assay buffer such that the final concentration of DMSO in the assay was 2%. Compounds were serially diluted (3-fold each time) for a 7 point inhibition analysis. HCV RdRp genotype 1b enzyme was used at a final concentration of 28 nM. A polyA template was used at 28 nM, and the oligo-$dT_{12-18}$ primer was used at 840 nM final concentration. Preannealed primer and template were obtained commercially (Amersham 27-787802). $^3$H-UTP was used at 0.125 µCi (1 µM total UTP). Reaction was initiated by the addition of enzyme. Reactions were incubated at 30° C. for 45 min, and stopped by adding 30 ul of 20% ice cold TCA. Plates were chilled for 30 minutes and harvested onto Unifilter-96, GF/B plates (Packard, 6005177) using a Packard FilterMate Cell Harvester. The harvest plates were prewashed 3 times, 200 ul/well, with 100 mM NaPPi. Harvested filters were washed 30 times, 200 ul/well, with distilled water followed by ethanol. Filter plates were dried, and 30 ul/well microscint-20 was added. Plates were read on a Packard Top Count NXT.

The $IC_{50}$ values for compounds were determined using six different [I], combined with 7 nM enzyme, 800 ng of the template-primer polyC/oligo$G_{12}$ (1:5 molar ratio), and 0.7 uM of $^3$H GTP containing 1 uCi. The observed fractional activity (fa=vi/vo) was used in the equation $IC_{50}=[I]/(1/fa-1)$ to determine a single point $IC_{50}$ value. Typically, the single point $IC_{50}$ values derived from [I] that produced fractional activities in the range of 0.1 to 0.8 relative to the uninhibited control were averaged to calculate the $IC_{50}$ value for each compound.

FRET Assay Preparation. To perform the HCV FRET screening assay, 96-well cell culture plates were used. The FRET peptide (Anaspec, Inc.) (Taliani et al., *Anal. Biochem.* 240: 60–67 (1996), expressly incorporated by reference in its entirety) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The assay reagent was made as follows: 5x cell Luciferase cell culture lysis reagent from Promega (#E153A) diluted to 1x with $dH_2O$, NaCl added to 150 mM final, the FRET peptide diluted to 20 uM final from a 2 mM stock. Cells were trypsinized, placed into each well of a 96-well plate and allowed to attach overnight. The next day, the test compounds were added to columns 1 through 10; column 11 was media only, and column 12 contained a titration of interferon as a control (1000units for A12, B 12, 100units for C12, D12, 10units for E12, F12 and 1 unit for G12, H12). The plates were then placed back in the incubator.

FRET Assay and Cytotoxicity Assay. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold.

Compound analysis was determined by quantification of the relative HCV replicon inhibition and the relative cytotoxicity values. To calculate cytoxicity values, the average Alamar Blue fluorescence signals from the control wells in row 11 were set as 100% non-toxic. The individual signals in each of the compound test wells were then divided by the average control signal and multiplied by 100% to determine percent cytotoxicity. To calculate the HCV replicon inhibition values, an average background value FRET signal was obtained from the two wells containing the highest amount of interferon at the end of the assay period. These numbers were similar to those obtained from naïve Huh-7 cells.

The background numbers were then subtracted from the average FRET signal obtained from the control wells in row 11 and this number was used as 100% activity. The individual signals in each of the compound test wells were then divided by the averaged control values after background subtraction and multiplied by 100% to determined percent activity. $EC_{50}$ values for an interferon titration were calculated as the concentration which caused a 50% reduction in HCV RNA, HCV protein amounts or FRET activity. The two numbers generated for the compound plate, percent cytotoxicity and percent activity were used to determine compounds of interest for further analysis.

The HCV NS5B RdRp enzyme inhibition assay results are tabulated in Table 1.

TABLE 1

| Example | RdRp Inhibition $IC_{50}$ (µM) |
|---|---|
| 1 | >25 |
| 2 | >25 |
| 3 | 15 |
| 4 | >25 |
| 5 | 0.45 |
| 6 | >25 |
| 7 | 10 |
| 8 | >25 |
| 9 | 0.27 |
| 10 | >25 |
| 11 | >25 |
| 12 | >25 |
| 13 | 0.38 |
| 14 | >25 |
| 15 | >25 |
| 16 | >25 |

TABLE 1-continued

| Example | RdRp Inhibition IC$_{50}$ (μM) |
|---|---|
| 17 | 1.8 |
| 18 | >25 |
| 19 | 4.9 |
| 20 | >25 |
| 21 | 2.3 |
| 22 | >25 |
| 23 | >25 |
| 24 | 3.1 |
| 25 | >25 |
| 27 | >25 |
| 28 | 1.3 |
| 29 | >25 |
| 30 | >25 |
| 31 | 4.5 |
| 32 | >25 |
| 33 | 2.4 |
| 34 | >25 |
| 35 | >25 |
| 36 | >25 |
| 38 | >25 |
| 39 | 4.0 |
| 40 | >25 |
| 41 | 10 |
| 42 | >25 |
| 43 | 0.31 |
| 44 | >25 |
| 45 | 6.6 |
| 46 | >25 |
| 47 | >25 |
| 48 | 5.3 |
| 49 | >25 |
| 50 | 15 |
| 51 | >25 |
| 52 | 2.5 |
| 53 | >25 |
| 54 | 1.6 |

Pharmaceutical Compositions and Methods of Use

The compounds of this invention inhibit HCV NS5B RNA-dependent RNA polymerase (RdRp). This polymerase is one of a small number of functional enzymes encoded by the viral RNA and is known to be essential for infectivity of chimpanzees. By inhibiting this enzyme, the compounds of this invention are useful for impeding or preventing HCV infection and for treating hepatitis C. At least one other compound which acts on this enzyme is currently undergoing clinical evaluation for hepatitis C (Tan, S.-L.; Pause, A.; Shi, Y.; Sonenberg, N. Nature Reviews/Drug Discovery 2002, 1, 867–881).

The compounds of this invention are generally given as pharmaceutical compositions comprised of a therapeutically effective amount of a compound of Formula I of its pharmaceutically acceptable salt and a pharmaceutically acceptable carrier and may contain conventional exipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. Compositions are normally formulated in dosage units and compositions providing from about 1 to 1000 mg of the active ingredient per dose are preferred.

Methods of treatment involve administering a therapeutically effective amount of a Formula I compound or a pharmaceutically acceptable salt to a patient exhibiting conditions responsive to HCV NS5B RdRp inhibition. The methods include all conventional modes of administration. Typical modes are oral, topical, rectal, nasal, and parenteral. Generally, the daily dosage will be from about 0.001 mg to 100 mg of Formula I compound per kilogram of bodyweight when used for hepatitis C. The specific dosing regimen, however, must be carefully adjusted using sound medical judgement.

The compounds of this invention can be used with other agents that inhibit HCV viral replication including replicase inhibitors, metalloprotease inhibitors, NS3 protease inhibitors, NS3 helicase inhibitors, NS5A inhibitors—including interferons (IFN), PEGylated interferons, and ribavirin—and NS5B polymerase inhibitors.

Additionally, the compounds can be used in conjunction with other hepatitis C compounds including inosine monophosphate dehydrogenase (IMPDH) inhibitors, immune modulators, serine protease inhibitors, immunoglobulin immunosuppressants, antivirals, antifibrotics, caspase inhibitors, and tubulin inhibitors, as well as monoclonal antibodies, ribozymes, and antisense agents.

The table below lists some compositions that can be administered with the compounds of this invention. The compounds of this invention can be administered with these compositions in combination therapy—either jointly or separately—or by combining the compounds with one or more of the compositions into a new composition.

TABLE 2

| Compound Name | Catagory | Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |

TABLE 2-continued

| Compound Name | Catagory | Company |
|---|---|---|
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Abbreviations

Solution ratio express a volume relationship, unless stated otherwise. NMR chemical shifts (δ) are reported in parts per million. Flash chromatography was carried out on silica gel according to Still's method (Still, W. C. et al. *J. Org. Chem.* (1978), 43, 2923). Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "ml" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

As used throughout the specification, the following abbreviations for chemical reagents apply:

Boc is tert-butyl oxycarbonyl,

BuLi is n-butyl lithium

Cbz is carbonylbenzyloxy,
DCE is 1,2-dichloroethane,
DIEA is diethylpropyl amine,
DMAP is dimethylaminopyridine,
DME is dimethylethyleneglycol
DMF is dimethylformamide,
EDCI is 1-(3-dimethylaminopropyl)-3-ethylcarbodiimide hydrochloride,
HOAt is 1-hydroxy-7-azabenzotriazole,
LiHMDS is bis(trimethylsilyl)amide,
NBS is N-bromosuccinamide,
NCS is N-chlorosuccinamide,
TBAI is tetrabutylammonium iodide,
TEA is triethylamine,
TFA is trifluoroacetic acid,
THF is tetrahydrofuran.

Intermediate 1.2

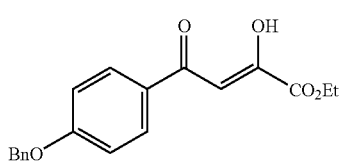

Ethyl (2Z)-2-hydroxy-4-oxo-4-(4-benzyloxyphenyl)-2-butenoate (1.2). To a solution of 4-benzyloxyacetophenone 1.1 (20.0 g, 88.4 mmol) in DMF (100 ml) at rt, was added NaH (60% in oil, 4.26 g, 106 mmol). The mixture was stirred at rt for 45 min, cooled to 0° C., and diethyl oxalate (14.4 ml, 106 mmol) was added dropwise, and the suspension warmed to rt and stirred for 17 h. The reaction mixture was poured over a mixture of ice and 1N HCl and the suspension stirred for 30 min, filtered, and the solid rinsed with water and dried to afford 28.9 g of the butenoate 1.2. MS (ESI) 325.2 (MH$^+$).

EXAMPLE 1

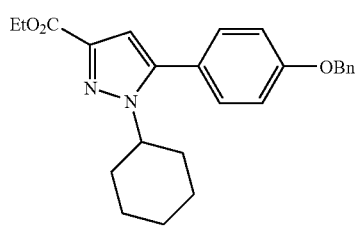

Ethyl 1-cyclohexyl-5-(4-benzyloxyphenyl)-1H-pyrazole-3-carboxylate (1.3). The butenoate 1.2 (5.00 g, 15.3 mmol) and cyclohexylhydrazine hydrochloride (2.77 g, 18.4 mmol) were heated at refluxed in EtOH (60 ml) for 2 h. Concentration in vacuo resulted in formation of a solid which was suspended in EtOAc and filtered through a 1" pad of SiO$_2$, elution with ethyl acetate. The filtrate was concentrated to afford 6.10 g (98%) of the desired pyrazole ester 1.3. MS (ESI) 405.4 (M+H$^+$).

Intermediate 2.1

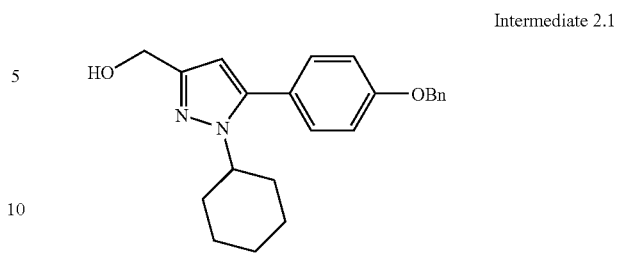

[1-cyclohexyl-5-(4-benzyloxyphenyl)-1H-pyrazol-3-yl] methanol (2.1). To a suspension of LAH (52 mg, 1.36 mmol) in THF (6 ml) at 0° C., was added dropwise a solution of pyrazole ester 1.3 (500 mg, 1.24 mmol) in THF (3 ml). The mixture was stirred at 0° C. for 30 min, quenched with H$_2$O, diluted with 1N HCl, and extracted with EtOAc (3×). The combined organic phase was washed with H$_2$O, brine, and dried (Na$_2$SO$_4$). Filtration through a 1" pad of SiO$_2$, elution with ethyl acetate, and concentration of the filtrate afforded 448 mg (100%) alcohol 2.1. HRMS (ESI) calc'd for C$_{23}$H$_{27}$N$_2$O$_2$ 363.1994; found 363.2083 (MH$^+$).

Intermediate 2.2

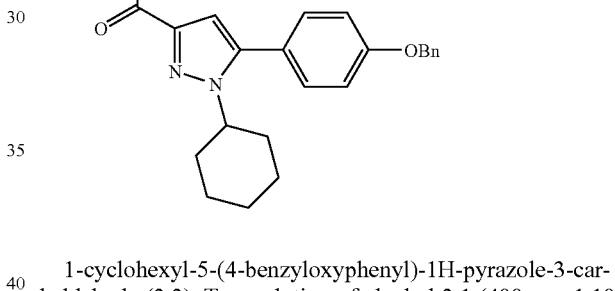

1-cyclohexyl-5-(4-benzyloxyphenyl)-1H-pyrazole-3-carbaldehyde (2.2). To a solution of alcohol 2.1 (400 mg, 1.10 mmol) in DME (10 ml) at reflux, was added MnO$_2$ (880 mg), portion-wise over 4 h. After being cooled to rt, the solution was concentrated and the crude product filtered though a 1" pad of SiO2, elution with ethyl acetate. The filtrate was concentrated to give aldehyde 2.2 260 mg (91%). HRMS (ESI) calc'd for C$_{23}$H$_{25}$N$_2$O$_2$ 361.1838; found 361.1926 (MH$^+$).

EXAMPLE 2

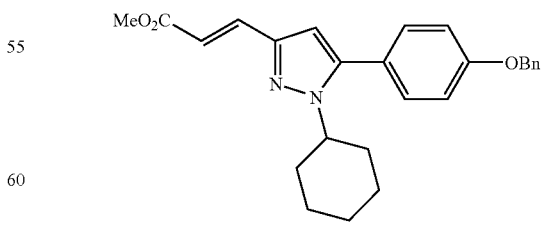

Methyl (2E)-3-{5-[4-(benzyloxy)phenyl]-1-cyclohexyl-1H-pyrazol -3-yl}-2-propenoate (2.3). A mixture of aldehyde 2.2 (311 mg, 0.863 mmol) and methyl (triphenylphosphoranyl-idene)acetate (317 mg, 0.949 mmol) in benzene (5 ml) were heated at reflux for 6 h. Additional methyl (triphenylphosphoranylidene)acetate (100 mg) was added and the mixture and after an addition 18 h at reflux, the reaction mixture was concentrated to give a residue purified by $SiO_2$ chromatography (stepwise gradient, 10 to 15% EtOAc/hexanes) to afford 2.3, 300 mg (83%). MS (ESI) 417.4 (M+H$^+$).

EXAMPLE 3

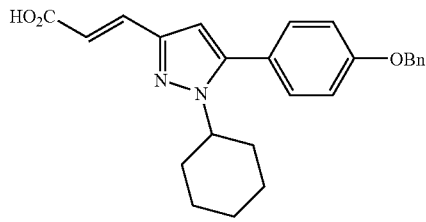

(2E)-3-[1-cyclohexyl-5-(4-benzyloxyphenyl)-1H-pyrazol-3-yl]-2-propenoic acid (2.4). To a solution of ester 2.3 (55 mg, 0.132 mmol) in 4.5 ml of THF/MeOH (8:1) was added 1N LiOH (2 ml), and the mixture was stirred for 24 h at rt. Concentration to remove solvent gave a residue that was taken $Et_2O$ and extracted with 0.1 N NaOH and $H_2O$ (2×). The combined aqueous extracts were acidified with concentrated HCl and extracted with EtOAc (3×). The combined organic extracts were washed with $H_2O$, brine, dried ($Na_2SO_4$). The crude product was triturated with hexanes to afford 45.8 mg (86%) of acid 2.4. HRMS (ESI) calc'd for $C_{25}H_{27}N_2O_3$ 403.1943; found 403.2019 (MH$^+$); $^1$H NMR (300 MHz, CDCl$_3$) δ 7.83 (d, J=16.1, 1H), 7.49–7.34 (m, 5H), 7.28 (d, J=8.8, 2H), 7.07 (d, J=8.8, 2H), 6.46 (s, 1H), 6.38 (d, J=15.7, 1H), 5.13 (s, 2H), 4.14–4.04 (m, 1H), 2.03–1.82 (m, 6H), 1.28–1.24 (m, 4H).

Intermediate 3.1

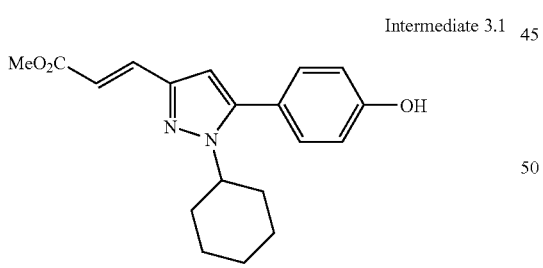

Methyl (2E)-3-[1-cyclohexyl-5-(4-hydroxyphenyl)-1H-pyrazol-3-yl]-2-propenoate (3.1). To a solution of ester 2.3 (50 mg, 0.120 mmol) in $CH_2Cl_2$ (2 ml) at −50° C. was added a 1M solution of $BCl_3$ in $CH_2Cl_2$ (600 µl 0.60 mmol), and the mixture was stirred for 30 min at that temperature before being quenched with MeOH, diluted with EtOAc, washed with $H_2O$, saturated NaHCO$_3$ (2×), brine, and dried ($Na_2SO_4$). After concentration, the residue was combined with another 0.024 mmol batch for purification by $SiO_2$ chromatography (30% EtOAc/hexanes) to afford 48 mg (100%) of phenol 3.1. MS (ESI) 327.3 (MH$^+$), 325.3 (MH$^-$).

EXAMPLE 4

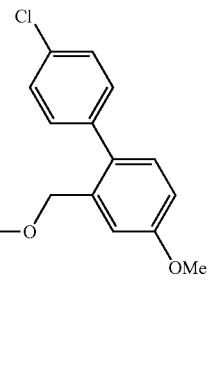

Methyl (2E)-3-(5-{4-[(4'-chloro-4-methoxy-1,1'-biphenyl-2-yl)methoxy]phenyl}-1-cyclohexyl-1H-pyrazol-3-yl)-2-propenoate (3.2). A mixture of phenol 3.1 (34 mg, 0.104 mmol), 4'-chloro-4-methoxy-1,1'-biphenyl-2-yl)methyl bromide (39.0 mg, 0.125 mmol), and powdered $K_2CO_3$ (28.7 mg, 0.208 mmol) were heated at refluxed for 1.5 h in CH$_3$CN (3 ml). The mixture was poured into EtOAc, washed with water, brine, and dried ($Na_2SO_4$). Purification by $SiO_2$ chromatography (stepwise gradient: 15 to 20% EtOAc/hexanes) gave 3.2, 52 mg (93%). MS (ESI) 557.3 (MH$^+$).

EXAMPLE 5

(2E)-3-(5-{4-[(4'-chloro-4-methoxy-1,1'-biphenyl-2-yl)methoxy]phenyl}-1-cyclohexyl-1H-pyrazol-3-yl)-2-propenoic acid (3.3). Methyl ester 3.2 (40 mg) and 1N LiOH (1 ml) in 3 ml MeOH/THF (1:2) was stirred at rt 18 h before being concentrated and partitioned between EtOAc and $H_2O$. The aqueous layer was acidified with 1N HCl and extracted with EtOAc (3×). The organic extracts were washed with $H_2O$, brine, and dried ($Na_2SO_4$). Concentration gave 3.3, 39 mg (100%). HRMS (ESI) calc'd for $C_{32}H_{32}ClN_2O_4$ 542.1972; found 543.2050 (MH$^+$); $^1$H NMR (300 MHz, CDCl$_3$) δ 7.83 (d, J=15.8, 1H), 7.39–7.23 (m, 7H), 7.18 (d, J=2.6, 1H), 6.99–6.94 (m, 3H), 6.45 (s, 1H), 6.38 (d, J=6.1, 1H), 4.94 (s, 2H), 4.13–4.01 (m, 1H), 3.88 (s, 3H), 2.04–1.83 (m, 6H), 1.32–1.21 (m, 4H).

EXAMPLE 6

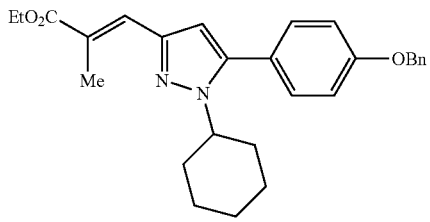

Ethyl (2E)-3-{5-[4-(benzyloxy)phenyl]-1-cyclohexyl-1H-pyrazol-3-yl}-2-methyl-2-propenoate (4.1). BuLi (1.6 M in hexanes, 956 μL, 1.53 mmol) was added dropwise to (1-ethoxycarbonyl-thyl)triphenylphosphonium bromide (738 mg, 1.66 mmol) in THF (7 ml) at 0° C., follow by addition of aldehyde 2.2 (500 mg, 1.39 mmol as solution in 3 ml of THF). The mixture was stirred at 0° C. for 30 min and warmed to rt, and after 1.5 h, $H_2O$ was added. The mixture was diluted with EtOAc, and the organic phase was washed with $H_2O$, brine, dried ($Na_2SO_4$). After being concentrated, the resultant residue was purified by $SiO_2$ chromatography (gradient elution: 10 to 15% EtOAc/hexanes) to provide 530 mg (86%) of 4.1. MS (ESI) 445.4 (MH+).

EXAMPLE 7

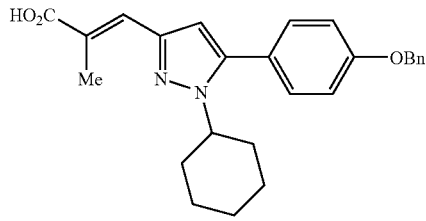

(2E)-3-{5-[4-(benzyloxy)phenyl]-1-cyclohexyl-1H-pyrazol-3-yl}-2-methyl-2-propenoic acid (4.2). A mixture of methyl ester 4.1 (50 mg, 0.112 mmol) and 1N LiOH (2 ml) in 3 ml of MeOH/THF (1:2) was stirred at rt for 18 h, concentrated, and partitioned between $Et_2O$ and $H_2O$. The organic phase was extracted with 0.1 N NaOH (2×), and the combined aqueous extracts were acidified with conc. HCl, and extracted with EtOAc (3×). The combined organic extracts were washed with $H_2O$, brine, and dried ($Na_2SO_4$) before being concentrated to afford 47 mg (100%) of 4.2. HRMS (ESI) calc'd for $C_{26}H_{29}N_2O_3$ 417.2178, found 417.2174 (MH+); $^1$H NMR (300 MHz, $CDCl_3$) δ 7.81 (d, J=1.1, 1H), 7.49–7.36 (m, 5H), 7.30 (d, J=8.7, 2H), 7.07 (d, J=8.7, 2H), 6.45 (s, 1H), 5.14 (s, 2H), 4.14–4.07 (m, 1H), 2.26 (d, J=1.5, 3H), 2.07–2.00 (m, 2H), 1.95–1.84 (m, 4H), 1.36–1.22 (m, 4H).

Intermediate 4.3

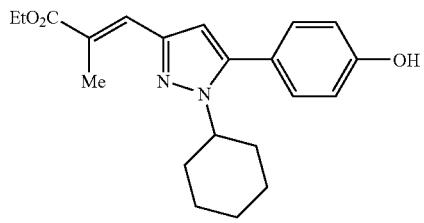

Ethyl (2E)-3-[1-cyclohexyl-5-(4-hydroxyphenyl)-1H-pyrazol-3-yl]-2-methyl-2-propenoate (4.3). To a solution 4.1 (83 mg, 0.187 mmol) in $CH_2Cl_2$ (2 ml) at −50° C. was added a 1M solution of $BCl_3$ in $CH_2Cl_2$ (933 μL, 0.933 mmol) followed by stirring at −50° C. for 15 min, and quenched with MeOH. The mixture was diluted with EtOAc, washed with $H_2O$, sat. $NaHCO_3$, brine, and dried ($Na_2SO_4$). Filtration through a 1" pad of $SiO_2$ and concentration to provided 4.3, 67 mg (100%). MS (ESI) 355.3 (MH+), 353.3 (MH−).

EXAMPLE 8

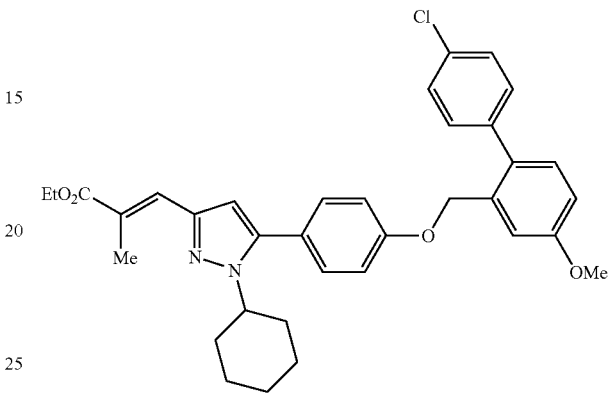

Ethyl (2E)-3-(5-{4-[(4'-chloro-4-methoxy-1,1'-biphenyl-2-yl)methoxy]phenyl}-1-cyclohexyl-1H-pyrazol-3-yl)-2-methyl-2-propenoate (4.4). A mixture of ethyl ester 4.3 (40.8 mg, 0.114 mmol), 4'-chloro-4-methoxy-1,1'-biphenyl-2-yl) methyl bromide (42.7 mg, 0.137 mmol), and powdered $K_2CO_3$ (31.5 mg, 0.228 mmol) were taken up in $CH_3CN$ (2 ml) and heated at reflux for 2 h prior to being poured into EtOAc, washed with water, brine, and dried ($Na_2SO_4$). Concentration and purification by $SiO_2$ chromatography (stepwise gradient: 5 to 7.5 to 10 to 12.5% EtOAc/hexanes) to gave 67 mg (100%) of 4.4. MS (ESI) 585.4 (MH+).

EXAMPLE 9

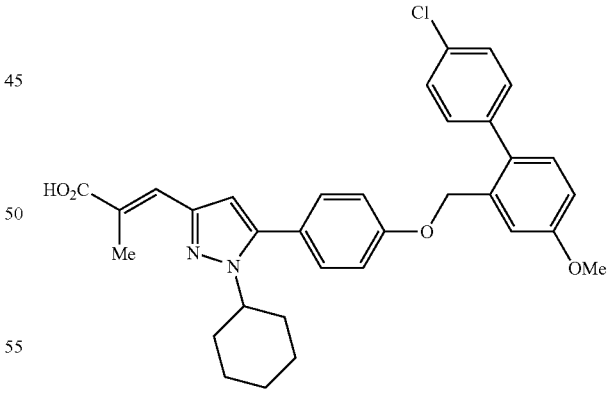

(2E)-3-(5-{4-[(4'-chloro-4-methoxy-1,1'-biphenyl-2-yl) methoxy]phenyl}-1-cyclohexyl-1H-pyrazol-3-yl)-2-methyl-2-propenoic acid (4.5). Ethyl ester 4.4 (55 mg, 0.094 mmol) was stirred with 1N LiOH (1 ml) in 4 ml of MeOH/THF (1:3) at rt for 24 h, concentrated, and partitioned between $Et_2O$ and $H_2O$. The organic phase was extracted with 0.1 N NaOH (2×), and the combined aqueous extracts were acidified with conc. HCl and extracted with EtOAc (3×). The combined organic extracts were washed with $H_2O$, brine, and dried ($Na_2SO_4$). Concentration gave a crude product which was purified by semi-preparative HPLC (gradient elution: 70 to 100% CH$_3$CN/H$_2$O+0.1% TFA) to give 4.5,47 mg (90%). HRMS (ESI) calc'd for C$_{33}$H$_{34}$ClN$_2$O$_4$ 577.2207, found 557.2218 (MH$^+$); $^1$H NMR (300 MHz, CDCl$_3$) δ 7.83 (d, J=1.1, 1H), 7.39–7.25 (m, 7H), 7.19 (d, J=2.5, 1H), 7.00–6.95 (m, 3H), 6.47 (s, 1H), 4.95 (s, 2H), 4.14–4.05 (m, 1H), 3.88 (s, 3H), 2.24 (s, 3H), 2.10–1.98 (m, 2H), 1.94–1.87 (m, 4H), 1.27–1.22 (m, 4H).

EXAMPLE 10

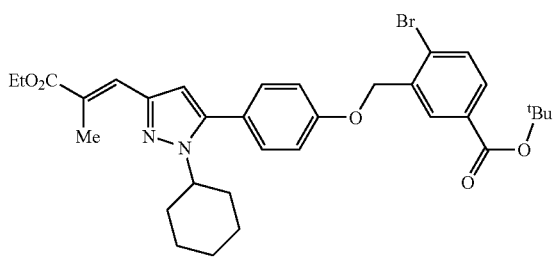

Ethyl (2E)-3-(5-{4-[(t-butyl-2-bromo-5-phenylcarboxylate)methoxy]phenyl}-1-cyclohexyl-1H-pyrazol-3-yl)-2-methyl-2-propenoate (5.1). Phenol 4.3 (116 mg, 0.33 mmol) was dissolved in of DMF (3.2 ml), cesium carbonate (341 mg, 1.05 mmol), and bromide (120 mg, 0.34 mmol) were added, and the reaction was stirred for 18 h at rt under N$_2$. Solvent was removed in vacuo, and the residue partitioned between ethyl acetate and water. The organic layer was washed with brine, dried (MgSO$_4$), and concentrated. Purification by silica gel chromatography (stepwise gradient; 7% to 25% EtOAc/Hexanes) gave a colorless amorphous solid 124 mg (60%) of 5.1. MS (ESI) 625.3 (MH$^+$).

EXAMPLE 11

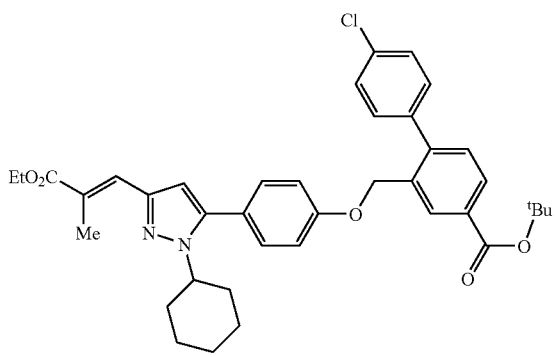

Ethyl (2E)-3-(5-{4-[(4'-chloro-4-t-butoxycarbonyl-1,1'-biphenyl-2-yl)methoxy]phenyl}-1-cyclohexyl-1H-pyrazol-3-yl)-2-methyl-2-propenoate (5.2). Bromide 5.1 (120 mg, 0.19 mmol) and 4-chlorophenylboronic acid (33 mg, 0.21 mmol) were admixed in a 2 dram vial containing anhydrous THF (1.9 ml) and saturated NaHCO$_3$ solution (1.1 ml) and the solution sparged with N$_2$ prior to addition of tetrakis (triphenylphosphine) palladium 0 (24 mg, 0.02 mmol). The reaction was heated to 80° C. for 18 h, cooled, partitioned between EtOAc and water, and the organic layer washed with brine, and dried (MgSO$_4$). Purificaion by silica gel chromatography (stepwise gradient: 5% to 25% EtOAc/ Hexanes) yielded 103 mg (82%) of 5.2. MS (ESI) 655.3 (MH+).

EXAMPLE 12

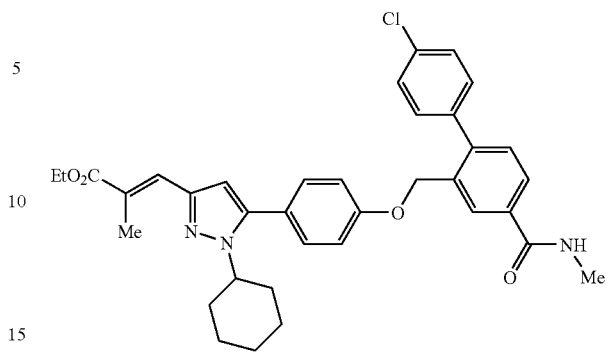

Ethyl (2E)-3-(5-{4-[(4'-Chloro-4-N-methylcarbamoyl-1, 1'-biphenyl-2-yl)methoxy]phenyl}-1-cyclohexyl-1H-pyrazol-3-yl)-2-methyl-2-propenoate (5.3). Ester 5.2 (103 mg, 0.157 mmol) was dissolved in dicholormethane (5 ml) and after trifluoroacetic acid (5 ml) was added under N$_2$ the reaction was capped and stirred for 2 h. Volatiles were removed in vacuo (co-evaporate with toluene) and the residue was placed on high vacuum 1 h to remove trace moisture [MS (ESI) 599.2 (MH+)], and the dried was dissolved in DMF (2.5 ml). Diisopropylethylamine (0.186 ml), O-benzotriazol-1-yl-N,N,N',N'-tetramethyluronium tetrafluoroborate (TBTU) (85 mg, 0.26 mmol) were added and the solution stirred for 10 min. An aliquot (0.675 ml, 0.043 mmol) of the solution was partitioned into 2 dram vial and N-methylamine (0.3 mmol, 7 eq, gas) amine added. The reaction was stirred under N$_2$ for 16 h, solvent removed in vacuo and residue purified by chromatography (ISCO Optix 10 system equipped with 4.2 g silica gel redi-sep cartridges) to give 17.4 mg (66%) of 5.3. MS (ESI) 626.2 (MH+).

EXAMPLE 13

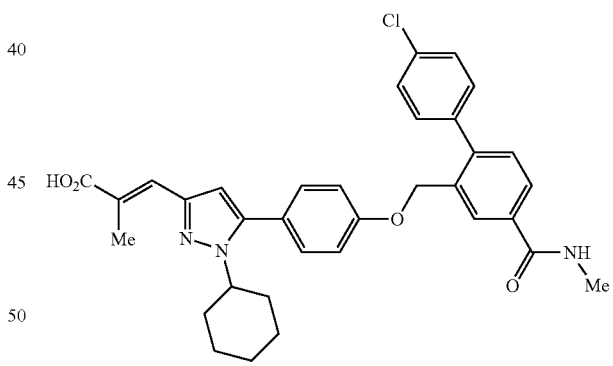

(2E)-3-(5-{4-[(4'-Chloro-4-N-methylcarbamoyl-1,1'-biphenyl-2-yl)methoxy]phenyl}-1-cyclohexyl-1H-pyrazol-3-yl)-2-methyl-2-propenoic acid (5.4). Ester 5.3 (12.1 mg, 0.02 mmol) was dissolved in THF (0.25 ml), 1N sodium hydroxide (0.04 ml, 0.04 mmol) added, and the reaction mixture heated at 60° C. for 5.5 h. The solvent was removed in vacuo and the residue partitioned between EtOAc and 1N HCl. The organic layer was washed with brine and dried (MgSO4), and concentrated to give 11 mg (95%) of 5.4. HRMS (ESI) calc'd for C$_{34}$H$_{35}$ClN$_3$O$_4$ 584.2316, found 584.2303 (MH+); 1H NMR (300 MHz, CDCl$_3$) δ 8.05 (d, J=2.5, 1H), 7.80 (dd, J=3.0, 9.1, 1H), 7.78 (s, 1H), 7.42–7.28 (m, 7H), 6.95 (d, J=9.0, 2H), 6.43 (s, 1H), 4.97 (s, 2H), 3.05 (d, J=6.0, 3H), 2.25 (s, 3H), 2.10–1.65 (m, 6H), 1.29–1.21 (m, 5H).

EXAMPLE 14

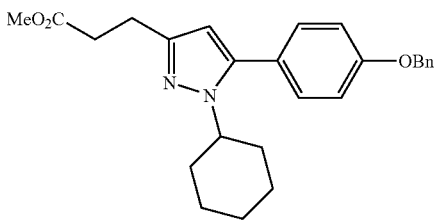

Methyl 3-{5-[4-(benzyloxy)phenyl]-1-cyclohexyl-1H-pyrazol-3-yl}propanoate (6.1). To a solution of methyl ester 2.3 (52 mg, 0.125 mmol) in benzene (5 ml) was added 10 mg of 10% Pd-C. The atmosphere was evacuated and flushed with $H_2$ gas (3×), and the solution stirred for 1.5 h. The mixture was filtered and concentrated to give 52 mg (100%) of 6.1. MS (ESI) 419.4 (M+H$^+$).

EXAMPLE 15

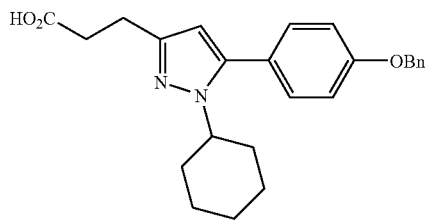

3-{5-[4-(benzyloxy)phenyl]-1-cyclohexyl-1H-pyrazol-3-yl}propanoic acid (6.2). Methyl ester 6.1 (53 mg) was stirred with 1N LiOH (2 ml) in 5 ml of MeOH/THF (4:1) over 18 h, concentrated, and partitioned between $Et_2O$ and $H_2O$. The organic phase was extracted with 0.1 N NaOH (2×), and the combined aqueous extracts were acidified with conc. HCl and extracted with EtOAc (3×). The organic extracts were washed with $H_2O$, brine, and dried ($Na_2SO_4$). The residue after concentration was triturated with hexanes/$Et_2O$ (10:1) to afford acid 6.2, 39 mg (100%). HRMS (ESI) calc'd for $C_{25}H_{29}N_2O_3$ 405.2100, found 405.2198 (MH$^+$); MS (ESI); $^1$H NMR (300 MHz, CDCl$_3$) δ 7.48–7.34 (m, 5H), 7.27 (d, J=7.0, 2H), 7.06 (d, J=8.7, 2H), 6.01 (s, 1H), 5.13 (s, 2H), 4.06–3.98 (m, 1H), 3.02–2.97 (m, 2H), 2.85–2.81 (m, 2H), 1.91–1.83 (m, 6H), 1.26 (br s, 4H).

Intermediate 6.3

Methyl 3-[1-cyclohexyl-5-(4-hydroxyphenyl)-1H-pyrazol-3-yl]propanoate (6.3). To a solution of methyl ester 6.1 (71.5 mg, 0.172 mmol) in MeOH (4 ml) was added 20 mg 10% Pd-C prior to atmosphere evacuation and flushed with $H_2$ (3×). The reaction mixture was stirred under $H_2$ for 2 h, filtered, and concentrated to give 54 mg (96%) of 6.3. MS (ESI) 329.3 (MH$^+$), 327.3 (MH$^-$).

EXAMPLE 16

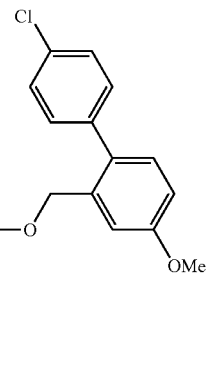

Methyl 3-(5-{4-[(4'-chloro-4-methoxy-1,1'-biphenyl-2-yl)methoxy]phenyl}-1-cyclohexyl-1H-pyrazol-3-yl)propanoate (6.4). A mixture 6.3 (39 mg, 0.119 mmol), 4'-chloro-4-methoxy-1,1'-biphenyl-2-yl)methyl bromide (44.4 mg, 0.143 mmol), and powdered $K_2CO_3$ (32.9 mg, 0.238 mmol) in $CH_3CN$ (2 ml) was heated at reflux for 1.5 h. The reaction mixture was filtered, poured into EtOAc, washed with water, brine, and dried ($Na_2SO_4$). Conentration purification by $SiO_2$ chromatography (stepwise gradient: 20 to 25% EtOAc/hexanes) to afforded 6.4, 66 mg (100%). MS (ESI) 559.5 (MH$^+$).

EXAMPLE 17

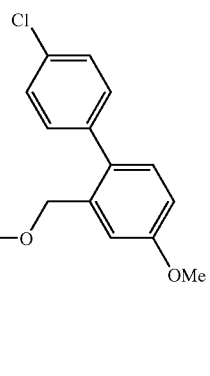

3-(5-{4-[(4'-chloro-4-methoxy-1,1'-biphenyl-2-yl)methoxy]phenyl}-1-cyclohexyl-1H-pyrazol-3-yl)propanoic acid (6.5). Methyl ester 6.4 (50 mg, 0.092) was stirred with 1N LiOH (2 ml) in 3 ml of MeOH/THF (2:1) at rt for 15 h, concentrated, and partitioned between $Et_2O$ and $H_2O$. The organic phase was extracted with 0.1 N NaOH (2×), and the combined aqueous extracts were acidified with conc. HCl and extracted with EtOAc (3×). The combined organic extracts were washed with $H_2O$, brine, dried ($Na_2SO_4$). The residue from concentration was purified by $SiO_2$ chromatography (stepwise gradient: 50 to 60 to 70% EtOAc/ hexanes) to yield 6.5, 31.6 mg (65%). HRMS (ESI) calc'd for $C_{32}H_{34}ClN_2O_4$ 545.2129, found 545.2204 (MH$^+$); $^1$H NMR (300 MHz, CDCl$_3$) δ 7.38–7.17 (m, 8H), 6.99–6.93 (m, 3H), 6.00 (2, 1H), 4.94 (s, 2H), 4.05–3.97 (m, 1H), 3.88 (s, 3H), 3.01–2.97 (m, 2H), 2.85–2.80 (m, 2H), 1.90–1.83 (m, 6H), 1.25 (br s, 4H).

Intermediate 7.1

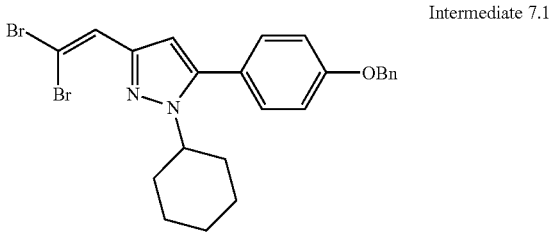

5-[4-(Benzyloxy)phenyl]-1-cyclohexyl-3-(2,2-dibromovinyl)-1H-pyrazole (7.1). To a solution of CBr$_4$ (916 mg, 2.76 mmol) in 7 ml of CH$_2$Cl$_2$ at 0° C., was added PPh$_3$ (1.45 g, 5.52 mmol), and the mixture was stirred at 0° C. for 10 min before addition of aldehyde 2.2 (500 mg, 1.38 mmol as a solution in 2 ml of CH$_2$Cl$_2$). The mixture was stirred at 0° C. for 30 min, diluted with hexanes, filtered through a 1″ pad of SiO$_2$ eluting with 10% EtOAc/hexanes. The filtrate was concentrated and the resultant residue purified by SiO$_2$ chromatography (5% EtOAc/hexanes) to afford 7.1, 648 mg (91%). MS (ESI) 515.1 (MH$^+$).

Intermediate 7.2

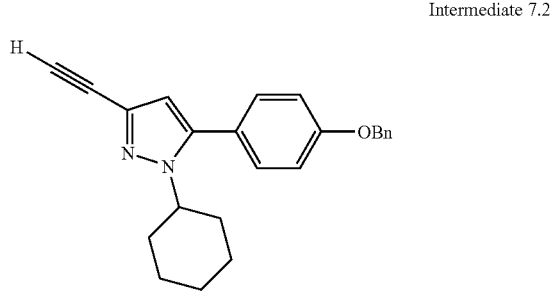

5-[4-(benzyloxy)phenyl]-1-cyclohexyl-3-ethynyl-1H-pyrazole (7.2). n-Butyllithium (1.6 M BuLi in hexanes, 1.65 ml, 2.64 mmol) was added dropwise to a solution of 7.1 (620 mg, 1.20 mmol) in THF (6 ml) at −50°. The mixture was stirred at −50° C. for 30 min, quenched with H$_2$O, diluted with EtOAc, washed with 1N HCl, H$_2$O, brine, and dried (Na$_2$SO$_4$). The crude product was purified by SiO$_2$ chromatography to afford 261 mg (61%) of 7.2. MS (ESI) 357.3 (MH$^+$).

EXAMPLE 18

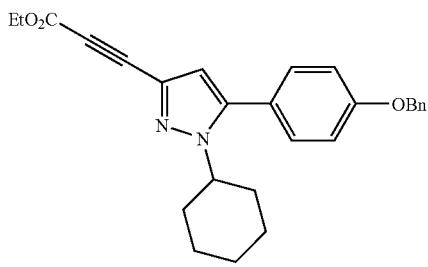

Ethyl 3-{5-[4-(benzyloxy)phenyl]-1-cyclohexyl-1H-pyrazol-3-yl}-2-propynoate (7.3). To a solution 7.2 (181 mg, 0.508 mmol) in 4 ml of THF at −78° C. was added BuLi (1.6 M in hexanes, 349 µL, 0.559 mmol), and the solution was stirred at −78° C. for 15 min, followed by additon of ethyl chloroformate (73 µL, 0.762 mmol). The mixture was allowed to warm to 0° C. over 30 min, quenched with H$_2$O, diluted with EtOAc, washed with H$_2$O, brine, and dried (Na$_2$SO$_4$). The mixture was combined with another 0.141 mmol batch for purification by SiO$_2$ chromatography (stepwise gradient: 5 to 7.5 to 10 to 12.5% EtOAc/hexanes) to give 7.3, 214 mg (77%). MS (ESI) 429.4 (MH$^+$).

EXAMPLE 19

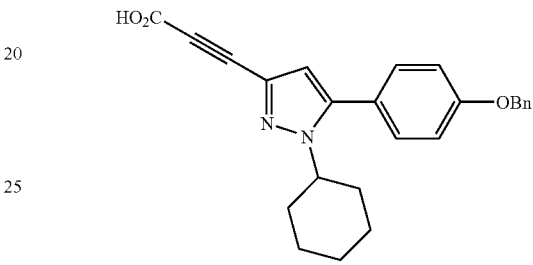

3-{5-[4-(benzyloxy)phenyl]-1-cyclohexyl-1H-pyrazol-3-yl}-2-propynoic acid (7.4). A mixture of ester 7.3 (68 mg, 0.157 mmol) and 1N LiOH (2 ml) in 6 ml MeOH/THF (1:2) was stirred at rt for 24 h, concentrated, and partitioned between Et$_2$O and H$_2$O. The organic phase was extracted with 0.1 N NaOH (2×), and the combined aqueous extracts were acidified with conc. HCl, and extracted with EtOAc (3×). The combined organic extracts were washed with H$_2$O, brine, and dried (Na$_2$SO$_4$) to afford 64 mg (100%) of acid 7.4. HRMS (ESI) calc'd for $C_{25}H_{25}N_2O_3$ 401.1865, found 401.1855 (M+H$^+$); $^1$H NMR (300 MHz, CDCl$_3$) δ 7.48–7.37 (m, 5H), 7.26 (d, J=8.8, 2H), 7.08 (d, J=8.8, 2H), 6.51 (s, 1H), 5.13 (s, 2H), 4.15–4.06 (m, 1H), 2.05–1.97 (m, 2H), 1.90–1.87 (m, 4H), 1.28–1.23 (m, 4H).

Intermediate 7.5

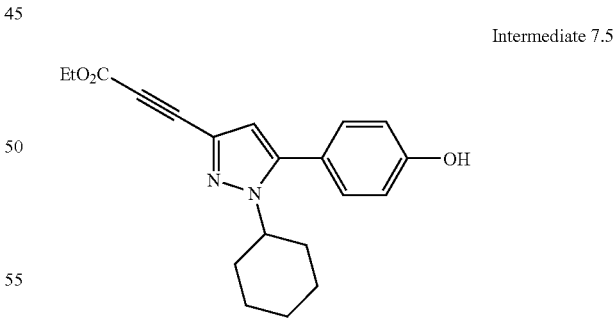

Ethyl 3-[1-cyclohexyl-5-(4-hydroxyphenyl)-1H-pyrazol-3-yl]-2-propynoate (7.5). A 1M solution of BCl$_3$ in CH$_2$Cl$_2$ (1 ml, 1.00 mmol) was added to a solution of intermediate 7.3 (86 mg, 0.207 mmol) in 2 ml of CH$_2$Cl$_2$ at −50° C., and after being stirred at −50° C. for 15 min, the solution was quenched with MeOH, diluted with EtOAc, washed with H$_2$O, sat. NaHCO$_3$, brine, and dried (Na$_2$SO$_4$). Filtration through a 1″ pad of SiO$_2$ and concentration provided 69 mg (100%) of 7.5. MS (ESI) 339.3 (MH$^+$), 337.3 (MH$^−$).

EXAMPLE 20

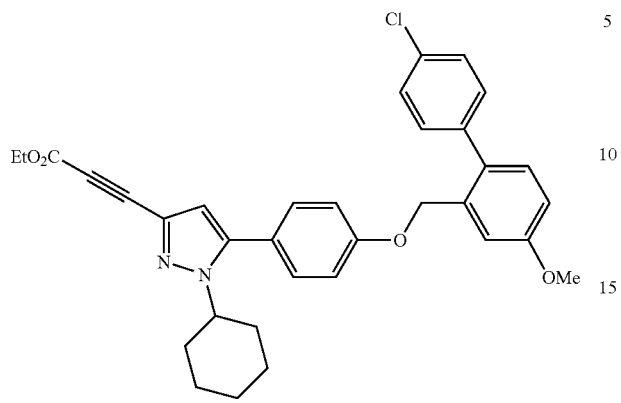

Ethyl 3-(5-{4-[(4'-chloro-4-methoxy-1,1'-biphenyl-2-yl)methoxy]phenyl}-1-cyclohexyl-1H-pyrazol-3-yl)-2-propynoate (7.6). A mixture of 7.5 (40.9 mg, 0.120 mmol), 4'-chloro-4-methoxy-1,1'-biphenyl-2-yl)methyl bromide (44.8 mg, 0.144 mmol), and powdered $K_2CO_3$ (33.2 mg, 0.240 mmol) in 2 ml of $CH_3CN$ was heated reflux for 2 h, poured into EtOAc, washed with water, brine, and dried ($Na_2SO_4$). The product was purified by $SiO_2$ chromatography (stepwise gradient: 5 to 7.5 to 10 to 12.5% EtOAc/hexanes) to afford 67 mg (98%) of 7.6. MS (ESI) 569.3 ($MH^+$).

EXAMPLE 21

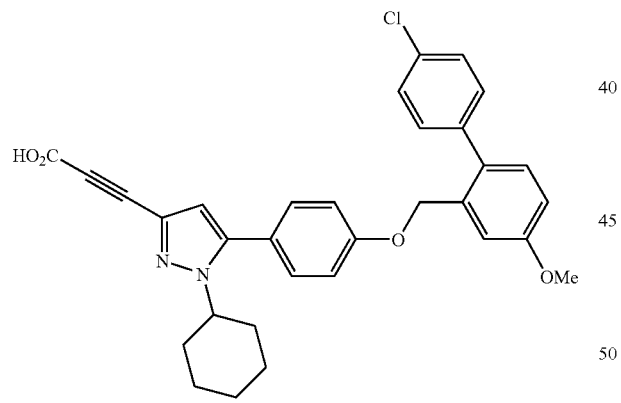

3-(5-{4-[(4'-chloro-4-methoxy-1,1'-biphenyl-2-yl)methoxy]phenyl}-1-cyclohexyl-1H-pyrazol-3-yl)-2-propynoic acid (7.7). Ester 7.6 (55 mg, 0.097 mmol) was stirred with 1N LiOH (1 ml) in 4 ml of MeOH/THF (1:3) at rt for 24 h, concentrated, and partitioned between $Et_2O$ and $H_2O$. The organic phase was extracted with 0.1 N NaOH (2×), and the combined aqueous extracts were acidified with conc. HCl, and extracted with EtOAc (3×). The combined organic extracts were washed with $H_2O$, brine, and dried ($Na_2SO_4$). The crude mixture was purified by semi-preparative HPLC (gradient elution: 70 to 100% $CH_3CN/H_2O$+0.1% TFA) to give 7.7, 52 mg (100%). HRMS (ESI) calc'd for $C_{32}H_{30}ClN_2O_4$ 514.1894, found 541.1913 ($MH^+$); $^1H$ NMR (300 MHz, $CDCl_3$) δ 7.39–7.17 (m, 8H), 7.00–6.94 (m, 3H), 6.51 (s, 1H), 4.95 (s, 2H), 4.14–4.05 (m, 1H), 3.88 (s, 3H), 2.08–1.96 (m, 2H), 1.90–1.86 (m, 4H), 1.26 (br s, 4H).

EXAMPLE 22

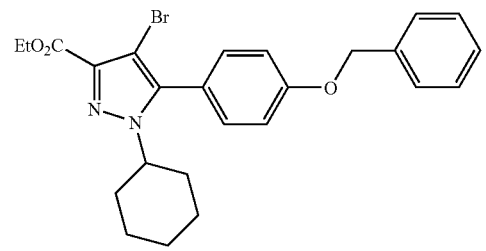

Ethyl 5-[4-(benzyloxy)phenyl]-4-bromo-1-cyclohexyl-1H-pyrazole-3-carboxylate (8.1). Bromine (82 μL, 1.61 mmol) was added to pyrazole 1.3 (500 mg, 1.24 mmol) in AcOH (5 ml) at 0° C. and the reaction mixture was stirred at rt for 17 h. Upon concentration, the crude product was purified by $SiO_2$ chromatography (stepwise gradient: 20 to 25% EtOAc/hexanes) to afford 368 mg (62%) of bromide 8.1. MS (ESI) 483.4 ($MH^+$).

Intermediate 8.2

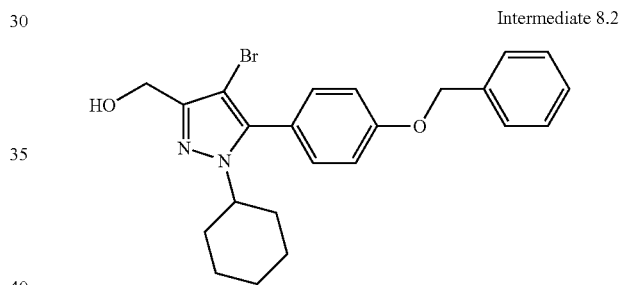

{5-[4-(benzyloxy)phenyl]-4-bromo-1-cyclohexyl-1H-pyrazol-3-yl}methanol (8.2). Alcohol 8.2 was prepared from 8.1 according to the procedure described above for the preparation of alcohol 2.1. The LAH reduction 8.2 in 310 mg (98%). MS (ESI) 441.4 ($MH^+$).

Intermediate 8.3

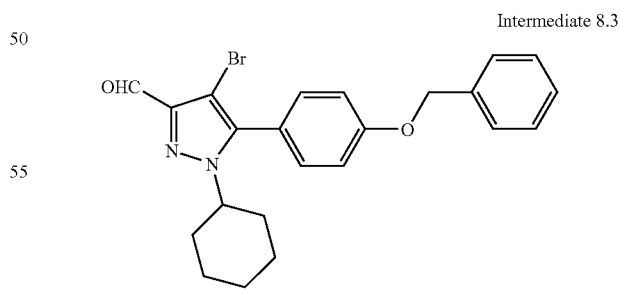

5-[4-(benzyloxy)phenyl]-4-bromo-1-cyclohexyl-1H-pyrazole-3-carbaldehyde (8.3). Aldehyde 8.3 was prepared from 8.2 according to the procedure described above for the preparation aldehyde 2.2. In this example, 8.2 (295 mg, 0.668 mmol) was oxidized to yield 242 mg (82%) of 8.3. MS (ESI) 439.3 ($MH^+$).

EXAMPLE 23

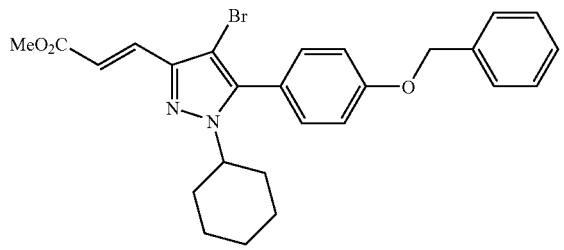

Methyl (2E)-3-{5-[4-(benzyloxy)phenyl]-4-bromo-1-cyclohexyl-1H-pyrazol-3-yl}-2-propenoate (8.4). Methyl ester 8.4 was prepared from 8.3 according to the procedure described above for the preparation ester 2.3. Thus, 8.3 (227 mg, 0.517 mmol) yielded 244 mg (95%) of ester 8.4. MS (ESI) 495.4 (MH$^+$).

EXAMPLE 24

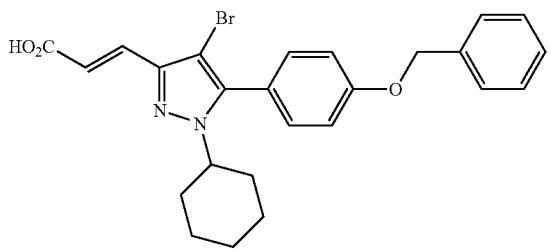

(2E)-3-{5-[4-(benzyloxy)phenyl]-4-bromo-1-cyclohexyl-1H-pyrazol-3-yl}-2-propenoic acid (8.5). Acid 8.5 was prepared from 8.4 according to the procedure described above for the preparation acid 2.4. Thus, 8.4 (47 mg, 0.095 mmol) was saponified to yield 45 mg (99%) of 8.5. HRMS (ESI) calc'd for $C_{25}H_{26}BrN_2O_3$ 481.1127, found 481.1105 (MH$^+$); $^1$H NMR (300 MHz, CDCl$_3$) δ 7.78 (d, J=16.1,1H), 7.49–7.34 (m, 5H), 7.27 (d, J=8.8, 2H), 7.12 (d, J=8.8, 2H), 6.88 (d, J=16.1, 1H), 5.14 (s, 2H), 4.04–3.96 (m, 1H), 2.00–1.83 (m, 6H), 1.26–1.24 (m, 4H).

EXAMPLE 25

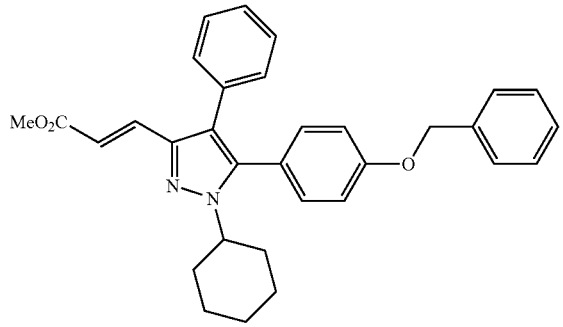

Methyl (2E)-3-{5-[4-(benzyloxy)phenyl]-1-cyclohexyl-4-phenyl-1H-pyrazol-3-yl}-2-propenate (8.6). To a degassed mixture of bromide 8.4 (150 mg, 0.303 mmol), phenyl boronic (44 mg, 0.36 mmol), and tri-o-tolylphosphine (9.3 mg, 0.03 mmol), and NaHCO$_3$ (105 mg, 1.25 mmol) in DME/H$_2$O (3:1) was added Pd(OAc)$_2$ (cat.). The mixture was stirred at 90° C. for 45 min, diluted with EtOAc, washed with water, brine, and dried (Na$_2$SO$_4$). Purification by silica gel chromatography (stepwise gradient: 10 to 15% EtOAc/hex) gave 115 mg (77%) of 8.6. MS (ESI) 493.5 (MH$^+$).

EXAMPLE 26

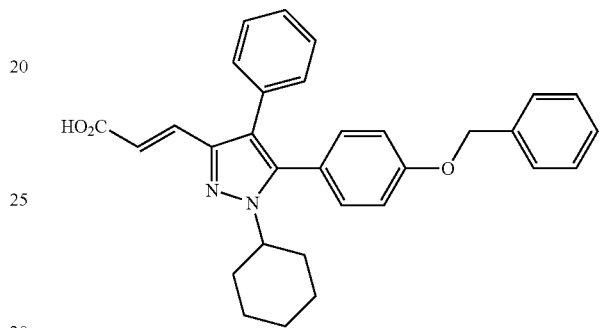

(2E)-3-{5-[4-(benzyloxy)phenyl]-1-cyclohexyl-4-phenyl-1H-pyrazol-3-yl}-2-propenoic acid (8.7). Acid 8.7 was prepared from ester 8.6 according to the procedure described above for the preparation acid 2.4. Thus, 8.6 (50 mg, 0.11 mmol) was saponified to yield 46 mg (95%) of 8.7. HRMS (ESI) calc'd for $C_{31}H_{31}N_2O_3$, 479.2335, found 479.2343 (MH$^+$); $^1$H NMR (300 MHz, CDCl$_3$) δ 7.72 (d, J=15.7, 1H), 7.46–7.21 (m, 8H), 7.12–7.08 (m, 4H), 6.97 (d, J=8.7, 2H), 6.60 (d, J=15.7, 1H), 5.06 (s, 2H), 4.04–3.97 (m, 1H), 2.10–1.85 (m, 5H), 1.65 (br s, 1H), 1.33–1.22 (m, 4H).

Intermediate 8.8

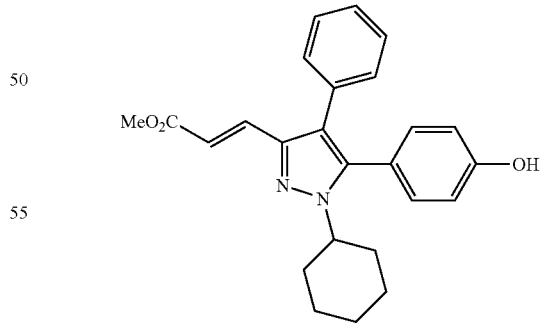

Methyl (2E)-3-[1-cyclohexyl-4-phenyl-5-(4-hydroxyphenyl)-1H-pyrazol-3-yl]-2-propenoate (8.8). Phenol 8.8 was prepared from 8.6 according to the procedure described above for the preparation phenol 3.1. Thus, 8.6 (60 mg, 0.12 mmol) was debenzylated to yield 49 mg (100%) of 8.8. MS (ESI) 403.3 (MH$^+$), 401.3 (MH$^-$).

EXAMPLE 27

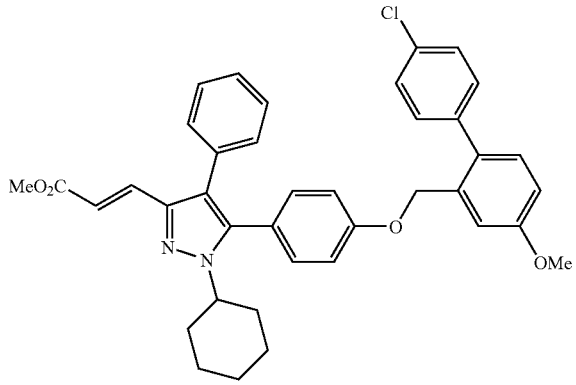

Methyl (2E)-3-(5-{4-[4'-chloro-4-methoxy-1,1-biphenyl) methoxy]phenyl}-1-cyclohexyl-4-phenyl-5-1H-pyrazol-3-yl]-2-propenoate (8.9). Ester 8.9 was prepared from 8.8 according to the procedure described above for the preparation 3.2. Thus, 8.8 (49 mg, 0.12 mmol) was alkylated with (4'-chloro-4-methoxy-1,1'-biphenyl-2-yl)methyl bromide to afford 69.5 mg (90%) of 8.9. MS (ESI) 633.4 (MH$^+$).

EXAMPLE 28

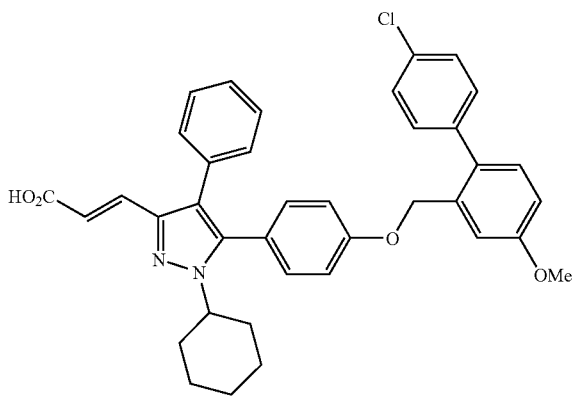

(2E)-3-(5-{4-[4'-chloro-4-methoxy-1,1-biphenyl)methoxy]phenyl}-1-cyclohexyl-4-phenyl-5-1H-pyrazol-3-yl]-2-propenoic acid (8.10). Ester 8.9 was saponified to 8.10 according to the procedure described above for the preparation acid 3.3. Thus, 8.9 (64 mg, 0.10 mmol) was hydrolyzed to afford 53 mg (85%) of 8.10. HRMS (ESI) calc'd for $C_{38}H_{36}ClN_2O_4$, 619.2364, found 619.2390 (MH$^+$); $^1$H NMR (300 MHz, CDCl$_3$) δ 7.72 (d, J=15.7, 1H), 7.37–7.22 (m, 8H), 7.16 (d, J=2.9, 1H), 7.07 (d, J=8.4, 1H), 6.96 (dd, J=8.5, 2.5, 1H), 6.85 (d, J=8.8, 2H), 6.60 (d, J=15.7, 1H), 4.88 (s, 2H), 4.03–3.94 (m, 1H), 3.87 (s, 3H), 2.09–1.85 (m, 5H), 1.66 (br s, 1H), 1.29–1.20 (m, 4H).

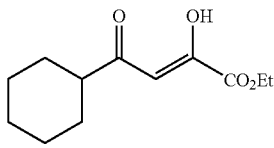

Intermediate 9.1

Ethyl (2Z)-4-cyclohexyl-2-hydroxy-4-oxo-2-butenoate (9.1). To a solution of cyclohexyl methyl ketone (10.4 g, 82.4 mmol) in DMF (90 ml) at rt, was added 60% NaH (3.96 g, 98.9 mmol). The mixture was stirred 45 min, cooled to 0° C., diethyl oxalate (13.4 ml, 98.9 mmol) was added and the temperature allowed to warm and stay at rt for 3 h. The reaction mixture was poured into Et$_2$O, extracted with H$_2$O (3×), and the aqueous phase was acidified with conc. HCl and extracted with EtOAc (3×). The organic extracts were washed with brine, dried (Na$_2$SO$_4$), and concentrated to afford 17.45 g (94%) of 9.1. MS (ESI) 225.2 (MH$^+$).

EXAMPLE 29

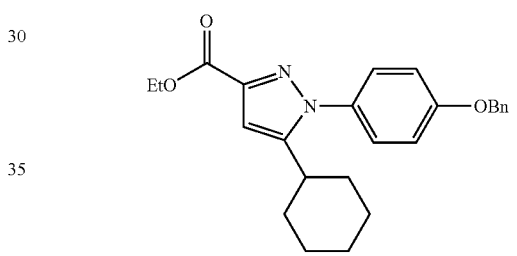

Ethyl 1-[4-(benzyloxy)phenyl]-5-cyclohexyl-1H-pyrazole-3-carboxylate (9.2). According to the procedure for preparation of 1.3, butenoate 9.1 (1 g, 4.42 mmol) and 4-benzyloxyhydrazine hydrochloride (1.33 g, 5.30 mmol) were combined and heated at reflux in EtOH (13 ml) for 1 h. The mixture was filtered, concentrated, and the resultant residue purified by SiO$_2$ chromatography (stepwise gradient, 10 to 35% EtOAc/hexanes) to afford 845 mg (47%) of 9.2. MS (ESI) 405.4 (MH$^+$).

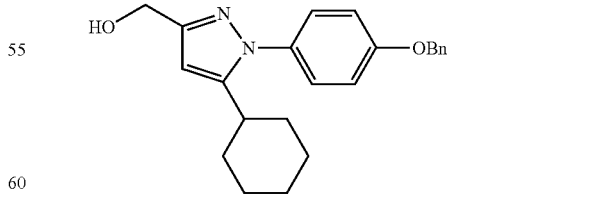

Intermediate 9.3

(2E)-3-{1-[4-(benzyloxy)phenyl]-5-cyclohexyl-1H-pyrazol-3-yl}-2-propenoic acid (9.3). Reduction of 9.2 (1 g, 2.47 mmol) was performed according to preparation of 2.1. Thus, 785 mg (83%) of 9.3 was obtained. MS (ESI) 363.4 (MH$^+$).

Intermediate 9.4

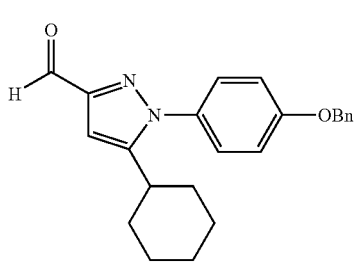

1-[4-(benzyloxy)phenyl]-5-cyclohexyl-1H-pyrazole-3-carbaldehyde (9.4). According to the procedure for preparation of 2.2, alcohol 9.3 (717 mg, 1.98 mmol) was oxidized to yield 675 mg (95%) of 9.4. HRMS (ESI) calc'd for $C_{23}H_{25}N_2O_2$ 361.1916, found 361.1914 (MH+).

EXAMPLE 30

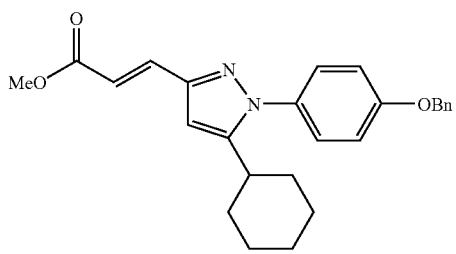

Methyl (2E)-3-{1-[4-(benzyloxy)phenyl]-5-cyclohexyl-1H-pyrazol-3-yl}-2-propenoate (9.5). According to the procedure for preparation of 2.3, aldehyde 9.4 (623 mg, 1.73 mmol) was reacted with methyl (triphenylphosphoranylidene)acetate (867 mg, 2.59 mmol) to yield 536 mg (74%) of 9.5. MS (ESI) 855.8 (2M+Na+).

EXAMPLE 31

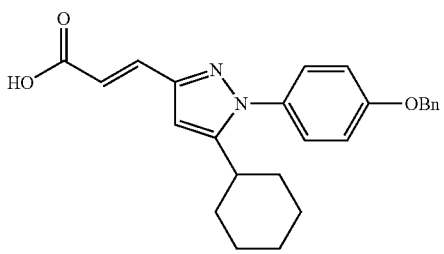

According to the procedure for preparation of 2.4, ester 9.5 (50 mg, 0.120 mmol) was saponified to yield 42 mg (88%) of 9.6. HRMS (ESI) calc'd for $C_{25}H_{27}N_2O_3$ 403.2022, found 403.2026 (MH+); $^1$H NMR (300 MHz, CDCl$_3$) δ 7.77 (d, J=16.1, 1H), 7.47–7.31 (m, 7H), 7.07 (d, J=8.8, 2H), 6.45 (s, 1H), 6.43 (d, J=16.1, 1H), 5.13 (s, 2H), 2.61–2.53 (m, 1H), 1.86–1.68 (m, 5H), 1.39–1.19 (m, 5H).

Intermediate 9.7

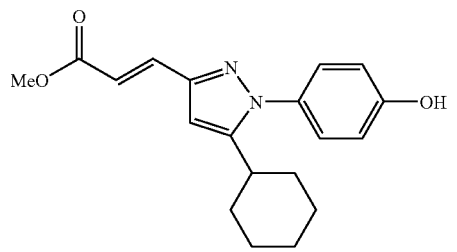

Methyl (2E)-3-[5-cyclohexyl-1-(4-hydroxyphenyl)-1H-pyrazol-3-yl]-2-propenoate (9.7). According to the procedure for preparation of 3.1, debenzylation of 9.5 (100 mg, 0.240 mmol) with BCl$_3$ (1.20 mmol) to yielded 70 mg (90%) of 9.7. MS (ESI) 653.7 (2MH+); (2M+Na+).

EXAMPLE 32

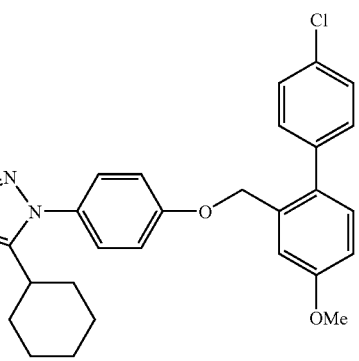

Methyl (2E)-3-(1-{4-[(4'-chloro-4-methoxy-1,1'-biphenyl-2-yl)methoxy]phenyl}-5-cyclohexyl-1H-pyrazol-3-yl)-2-propenoate (9.8). According to the procedure for preparation of 3.2, phenol 9.7 (55 mg, 0.169 mmol) was alkylated with 4'-chloro-4-methoxy-1,1'-biphenyl-2-yl)methyl bromide (63.0 mg, 0.202 mmol) to yield 87 mg (93%) of 9.8. MS (ESI) 557.5 (MH+).

EXAMPLE 33

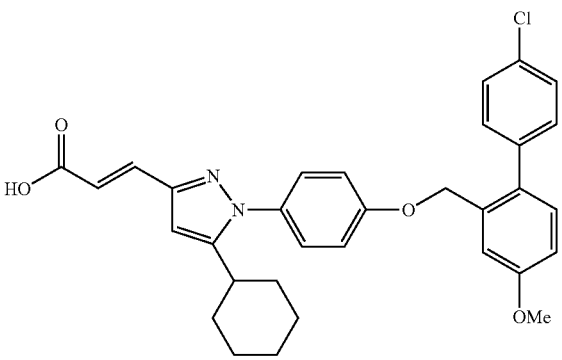

(2E)-3-(1-{4-[(4'-chloro-4-methoxy-1,1'-biphenyl-2-yl)methoxy]phenyl}-5-cyclohexyl-1H-pyrazol-3-yl)-2-propenoic acid (9.9). According to the procedure for the preparation of 3.3, ester 9.8 (72 mg, 0.129 mmol) was saponified to yield 50 mg (71%) of 9.9. HRMS (ESI) calc'd for $C_{32}H_{32}ClN_2O_4$ 543.2051, found 543.2021 (MH$^+$); $^1$H NMR (300 MHz, CDCl$_3$) δ 7.76 (d, J=16.1, 1H), 7.38–7.24 (m, 7H), 7.17 (d, J=2.5, 1H), 6.99–6.93 (m, 3H), 6.44 (s, 1H), 6.43 (d, J=15.7, 1H), 4.95 (s, 2H), 3.87 (s, 3H), 2.55–2.51 (m, 1H), 1.81–1.68 (m, 5H), 1.38–1.21 (m, 5H).

EXAMPLE 34

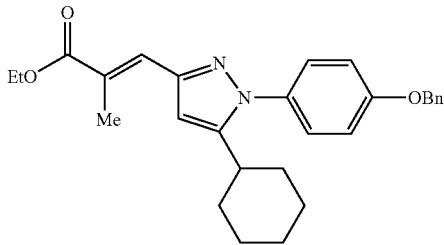

Ethyl (2E)-3-{1-[4-(benzyloxy)phenyl]-5-cyclohexyl-1H-pyrazol-3-yl}-2-methyl-2-propenoate (10.1). According to the procedure for preparation of 4.1, aldehyde 9.4 (500 mg, 1.39 mmol) was treated with (1-ethyoxycorbonylethyl)triphenylphosphonium bromide (739.6 mg, 1.67 mmol) to give 537 mg (87%) of 10.1. MS (ESI) 445.2 (MH$^+$).

EXAMPLE 35

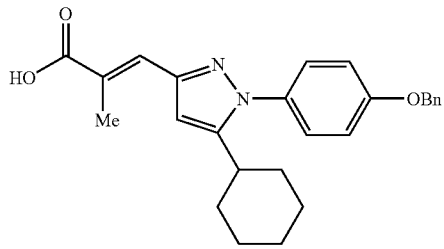

(2E)-3-{1-[4-(benzyloxy)phenyl]-5-cyclohexyl-1H-pyrazol-3-yl}-2-methyl-2-propenoic acid (10.2). Ethyl ester 10.1 was subject to saponification according to the procedure for preparation of 4.2 to give 41.9 mg (90%) of 10.2. HRMS (ESI) calc'd for $C_{26}H_{29}N_2O_3$ 417.2178, found 417.2167 (MH$^+$); $^1$H NMR (300 MHz, CDCl$_3$) δ 7.70 (s, 1H), 7.48–7.31 (m, 7H), 7.07 (d, J=29.1, 2H), 6.42 (s, 1H), 5.13 (s, 2H), 2.65–2.57 (m, 1H), 2.27 (s, 3H), 1.88–1.67 (m, 5H), 1.41–1.22 (m, 5H).

Intermediate 10.3

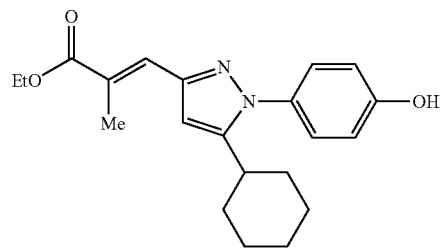

Ethyl (2E)-3-[5-cyclohexyl-1-(4-hydroxyphenyl)-1H-pyrazol-3-yl]-2-methyl-2-propenoate (10.3). According to the procedure for preparation of 4.3, debenzylation of 10.1 (440 mg, 0.99 mmol) with 1M BCl$_3$ in dichloromethane (4.95 ml, 4.95 mmol) yielded 353 mg (100%) of 10.3. MS (ESI) 355.4 (MH$^+$).

EXAMPLE 36

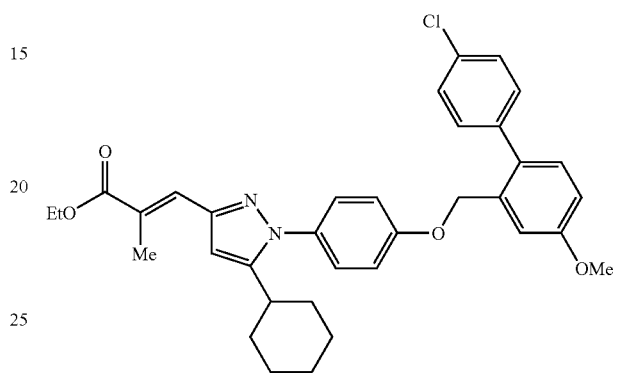

Ethyl (2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoate (10.4). According to the procedure for preparation of 4.4, phenol 10.3 (50 mg, 0.14 mmol) was alkylated with 4'-chloro-4-methoxy-1,1'-biphenyl-2-yl)methyl bromide (51 mg, 0.17 mmol) to yield 78.8 mg (96%) of 10.4. MS (ESI) 585.4 (MH$^+$).

EXAMPLE 37

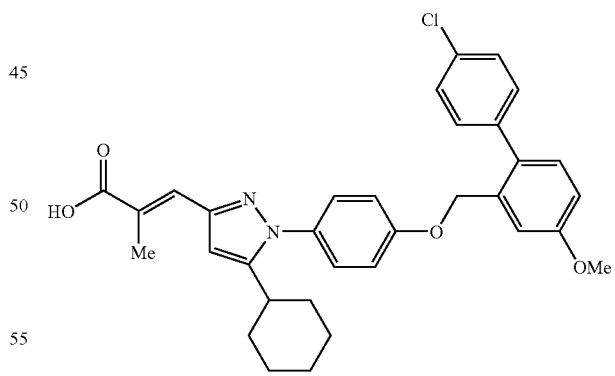

(2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoic acid (10.5). According to the procedure for the preparation of 4.5, ester 10.4 (53 mg, 0.091 mmol) was saponified to yield 20 mg (39%) of 10.5. MS (ESI) 557.4 (MH$^+$); $^1$H NMR (300 MHz, CDCl$_3$) δ 7.76 (s, 1H), 7.39–7.24 (m, 6H), 7.18 (d, J=2.5, 1H), 7.00–6.96 (m, 4H), 6.51 (s, 1H), 4.95 (s, 2H), 3.88 (s, 3H), 2.61–2.49 (m, 1H), 2.23 (s, 3H), 1.87–1.71 (m, 5H), 1.43–1.22 (m, 5H).

EXAMPLE 38

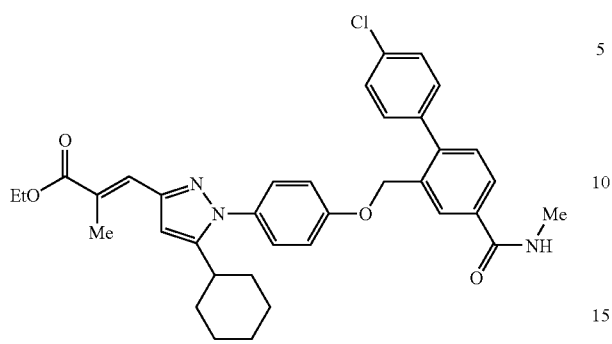

Ethyl (2E)-1-[4-(4'-Chloro-4-methylcarbamoyl-biphenyl-2-ylmethoxy)-phenyl]-5-cyclohexyl-1H-pyrazol-3-yl]-2-methyl-2-propenoate (10.6). Phenol 10.3 (44.3 mg, 0.125 mmol) was alkylated with 2-(bromomethyl)-4'chloro-N-methyl-1,1'-biphenyl-4-carboxamide (50 mg, 0.15 mmol; see reagent preparation below) according the preparation of 4.4 to provide 51 mg (59%) of amide 10.6. MS (ESI) 612.4 (MH$^+$).

EXAMPLE 39

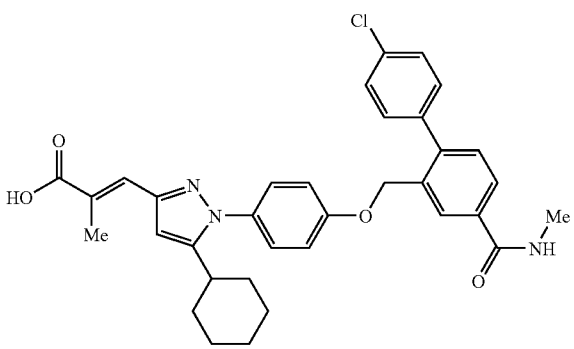

(2E)-1-[4-(4'-Chloro-4-methylcarbamoyl-biphenyl-2-ylmethoxy)-phenyl]-5-cyclohexyl-1H-pyrazol-3-yl]-2-methyl-2-propenoic acid (10.7). According to the procedure for preparation of 4.5, ester 10.6 (40 mg, 0.065 mmol) was saponified to give 30.5 mg (80%) of 10.7. HRMS (ESI) calc'd for $C_{34}H_{35}ClN_3O_4$ 584.2316, found 584.2324 (MH$^+$); $^1$H NMR (300 MHz, CDCl$_3$) δ 8.02 (d, J=2.5, 1H), 7.82 (dd, J=2.0, 7.9, 1H), 7.76 (d, J=1.1, 1H), 7.43–7.28 (m, 7H), 6.95 (d, J=8.8, 2H), 6.42 (s, 1H), 4.99 (s, 2H), 3.07 (d, J=3.7, 3H), 2.62–2.50 (m, 1H), 2.24 (d. J=1.1, 3H), 1.87–1.69 (m, 5H), 1.41–1.22 (m, 5H).

Preparation of 2-(bromomethyl)-4'chloro-N-methyl-1,1'-biphenyl-4-carboxamide

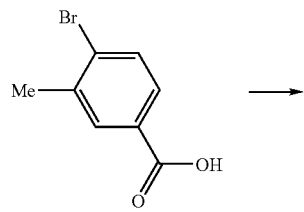

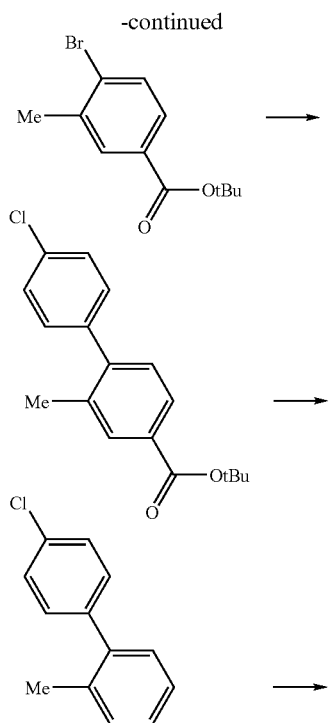

2-(bromomethyl)-4'chloro-N-methyl-1,1'-biphenyl-4-carboxamide. A suspension of 4-bromo-3-methylbenzoic acid (10 g, 46.5 mmol) was heated to 80° C. and N,N-dimethylformamide di-tert-butyl acetal (44.6 ml, 186 mmol) was added dropwise over 30 min under N$_2$ atmosphere. After being stirred 1.5 h, the reaction mixture was allowed to cool, washed with water, saturated NaHCO$_3$, brine, and dried (Na$_2$SO$_4$). Concentration afforded an off-white oil 8.8 g (70%) of tert-butyl 4-bromo-3-methylbenzoate. To a solution of this material (3.3 g, 12.2 mmol) in 3:1 dimethoxyethane/water (55 ml) was added 4-chlorophenyl boronic acid (2.3 g, 14.6 mmol), tri-o-tolylphosphine (371 mg, 1.22 mmol), NaHCO$_3$ (4 g, 48.8 mmol). After being degassed for 20 min by a bubbling stream of N$_2$, palladium acetate (137 mg, 0.6 mmol) was added, and the reaction heated at 90° C. for 2.5 h under N$_2$. The reaction mixture was cooled, and the organic layer washed with water, brine, and dried MgSO$_4$. Concentration gave a residue which was suspended in hexane and filtered to remove a precipitate which was washed well with 9:1 hexane/ethyl acetate mixture, and the combined filtrates concentrated. The residue from filtrate concentrataion was subject to Silica gel chromatography (stepwise gradient 0–10% EtOAc/hexane) to afford tertbutyl-4'-chloro-2-methyl-1,1'-biphenyl-4-carboxylate as a white solid 3.7 g (99%). MS (ESI) 303.1 (MH+). To a solution of this material (3.7 g, 12.2 mmol) in dichloromethane (92 ml) at 0° C. was added trifluoroacetate (92 ml) dropwise over 10 min. The solution was warmed to rt and stirred 1 h prior to concentration (co-evaporation with toluene, 2×50 ml) to give 4'-chloro-2-methyl-1,1'-biphenyl-4-carboxylate as a white solid 3 g (100%). MS (ESI) 247.1 (MH+). To a solution of this material (1.5 g, 6.0 mmol), 2M methyl amine in tetrahydrofuran (6 ml, 12. Mmol), and diisopropylamine (3.2 ml, 18 mmol) in dimethylformamide (30 ml) was added benzotriazol-1-yloxyltris(dimethylamino)-phosphonium hexafluorophosphate (3.22 g, 7.3 mmol) under a $N_2$ atmosphere. The reaction mixture was stirred at rt for 1 h, diluted with dichloromethane (100 ml), washed with water (2×30 ml), saturated $NaHCO_3$ (2×25 ml), brine, and dried ($Na_2SO_4$). Concentration and silica gel chromatography (stepwise gradient 50–100% $CH_2Cl_2$/hexane) to obtain 4'-chloro-N-methyl-1,1'-biphenyl-4-carboxamide. A sample of this material was dissolved in dichloromethane (30 ml) and N-bromosuccinamide (2.14 g, 12 mmol) was added and the reaction irradiated with ultraviolet light for 4 h under reflux and $N_2$ atmosphere. Concentration and purification by reverse phase HPLC (C18 column; water/acetonitrile/0.05% TFA; gradient) afforded 2-(bromomethyl)-4' chloro-N-methyl-1,1'-biphenyl-4-carboxamide.

EXAMPLE 40

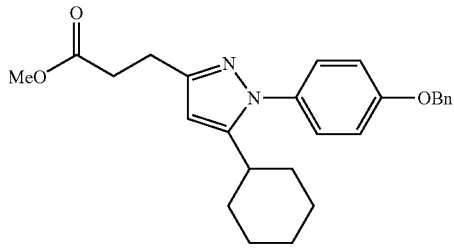

Methyl 3-{1-[4-(benzyloxy)phenyl]-5-cyclohexyl-1H-pyrazol-3-yl}propanoate (11.1). According to the procedure for preparation 6.1, propenoate 9.5 (149 mg, 0.358 mmol) was hydrogentaed to yield 144 mg (96%) of 11.1. MS(ESI) 419.4 (MH+).

EXAMPLE 41

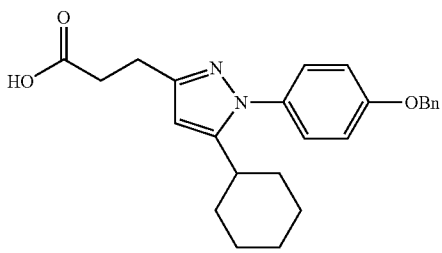

3-{1-[4-(benzyloxy)phenyl]-5-cyclohexyl-1H-pyrazol-3-yl}propenoic acid (11.2). According to the procedure for preparation of 6.2, ester 11.1 (44 mg, 0.105 mmol) was saponified to yield 39 mg (92%) of 11.2. HRMS (ESI) calc'd for $C_{25}H_{29}N_2O_3$ 405.2178, found 405.2192 (MH+); ¹H NMR (300 MHz, $CDCl_3$) δ 7.48–7.33 (m, 5H), 7.28 (d, J=8.1, 2H), 7.04 (d, J=8.8, 2H), 6.00 (s, 1H), 5.12 (s, 2H), 3.01–2.96 (m, 2H), 2.82–2.78 (m, 2H), 2.59–2.51 (m, 1H), 1.84–1.67 (m, 5H), 1.36–1.20 (m, 5H).

Intermediate 11.3

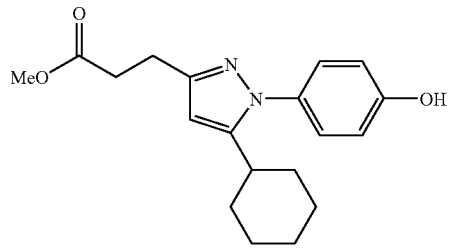

Methyl 3-[5-cyclohexyl-1-(4-hydroxyphenyl)-1H-pyrazol-3-yl]propanoate (11.3). According to the procedure for the preparation of 6.3, benzylether 11.2 (124 mg, 0.296 mmol) was cleaved by catalytic hydrogenation to yield 95 mg (98%) of 11.3. MS (ESI) 657.7 (2MH+).

EXAMPLE 42

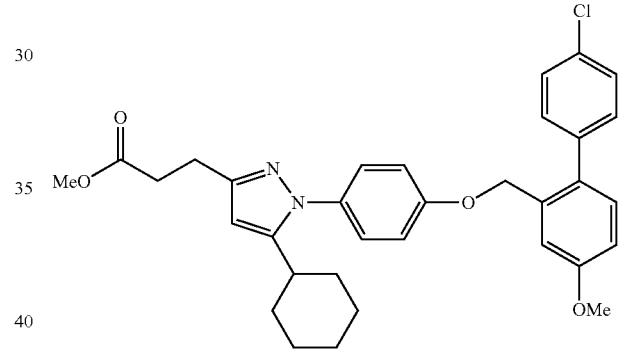

Methyl 3-(1-{4-[(4'-chloro-4-methoxy-1,1'-biphenyl-2-yl)methoxy]phenyl}-5-cyclohexyl-1H-pyrazol-3-yl)propanoate (11.4). According to the procedure for preparation of 6.4, phenol 11.3 (83 mg, 0.253 mmol) was alkylated with 4'-chloro-4-methoxy-1,1'-biphenyl-2-yl)methyl bromide (95 mg, 0.303 mmol) to yield 133 mg (94%) of 11.4. MS (ESI) 581.5 (M+Na+).

EXAMPLE 43

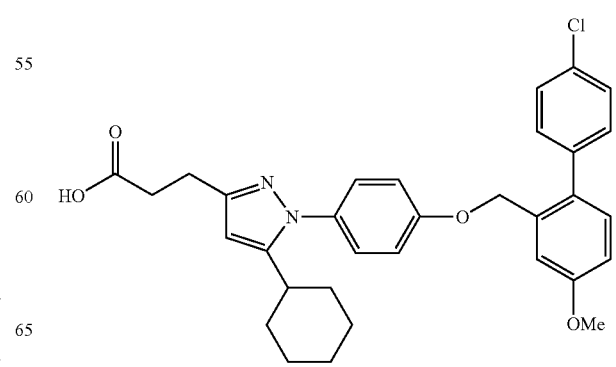

3-(1-{4-[(4'-chloro-4-methoxy-1,1'-biphenyl-2-yl)methoxy]phenyl}-5-cyclohexyl-1H-pyrazol-3-yl)propanoic acid (11.5). According to the procedure for preparation of 6.5, ester 11.4 (108 mg, 0.193 mmol) was saponified to yield 96 mg (91%) of 11.5. HRMS (ESI) calc'd for $C_{32}H_{34}ClN_2O_4$ 545.2207, found 545.2226 (MH+); 1H NMR (300 MHz, CDCl$_3$) δ 7.38–7.17 (m, 8H), 6.99–6.91 (m, 3H), 6.00 (s, 1H), 4.94 (s, 2H), 3.88 (s, 3H), 3.01–2.96 (m, 2H), 2.82–2.78 (m, 2H), 2.60–2.50 (m, 1H), 1.83–1.67 (m, 5H), 1.35–1.20 (m, 5H).

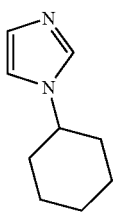

Intermediate 12.1

1-Cyclohexyl-1H-imidazole (12.1). Compound 12.1 was prepared in 44% yield by the procedure of Gridnev, A. A.; Mihaltseva, M. I. Synthesis of 1-Alkylimidazoles. *Syn. Comm.* 1994, 24, 1547–1555.

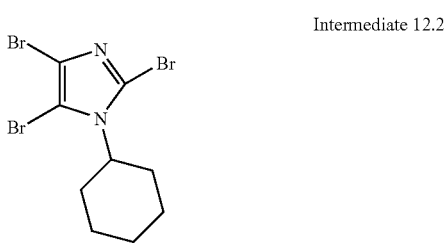

Intermediate 12.2

2,4,5-tribromo-1-cyclohexyl-1H-imidazole (12.2.). N-bromosuccinamide (1.78 g, 9.99 mmol) dissolved in CHCl$_3$ (4 ml) at 0° C. was added to a 4 ml solution of 12.1 (500 mg, 3.33 mmol) in CHCl$_3$. The mixture was stirred at rt for 17 h, filtered, concentrated, and the crude residue stirred in ether for 30 min. Filtration and concentration gave a crude product which was purified by SiO$_2$ chromatography (10% EtOAc/hexanes) to afford 267 mg (21%) 12.2. MS (ESI) 385.0 (MH+).

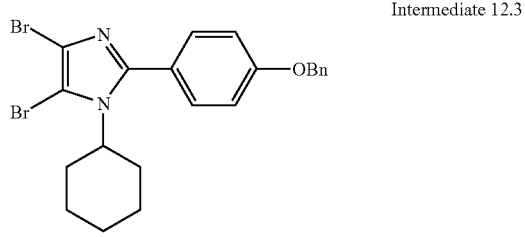

Intermediate 12.3

2-[4-(benzyloxy)phenyl]-4,5-dibromo-1-cyclohexyl-1H-imidazole (12.3). To a solution of 12.2 (1.99 g, 5.14 mmol) in 5:1 benzene/MeOH (24 ml) was added Na$_2$CO$_3$ (2M in water, 5.14 ml, 10.3 mmol) and 4-benzyloxyphenylboronic acid (1.23 g, 5.40 mmol). The mixture was degassed over 10 min with N$_2$ and tetrakis(triphenyl-phosphine)palladium (416 mg, 0.360 mmol) added, and the reaction mixture stirred at 65° C. for 12 h before being partitioned between EtOAc and H$_2$O. The organic phase was washed with brine, dried (Na$_2$SO$_4$), concentrated, and the crude product purified by SiO$_2$ chromatography (10% EtOAc/hexanes) to afford 1.96 g (78%) of 12.3. MS (ESI) 489.2 (MH+).

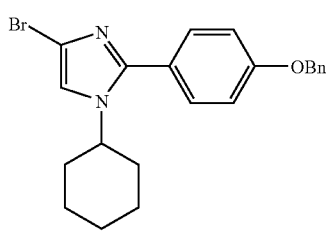

Intermediate 12.4

2-[4-(benzyloxy)phenyl]-4-bromo-1-cyclohexyl-1H-imidazole (12.4). To a solution of 12.3 (1 g, 2.04 mmol) in THF (11 ml) at −78° C. was added 1.6 M BuLi in hexanes (1.59 ml, 2.55 mmol). The mixture was stirred at −78° C. for 0.5 h, quenched with H$_2$O, warmed to rt, and partitioned between EtOAc and H$_2$O. The organic phase was washed with brine, dried (Na$_2$SO$_4$), concentrated, and the crude product purified by SiO$_2$ chromatography (stepwise gradient: 10 to 15 to 25% EtOAc/hexanes) to afford 723 mg (86%) of 12.4. MS (ESI) 411.3 (MH+).

EXAMPLE 44

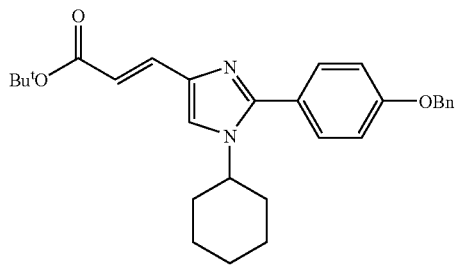

tert-butyl (2E)-3-{2-[4-(benzyloxy)phenyl]-1-cyclohexyl-1H-imidazol-4-yl}-2-propenoate (12.5). To a solution of 12.4 (100 mg, 0.243 mmol) in DMF (1.5 ml) was added tert-butyl acrylate (0.045 ml, 0.304 mmol) and tri-o-tolylphosphine (3.7 mg, 0.0122 mmol). After the 5 min degass with N$_2$, triethylamine (0.068 ml, 0.486 mmol) and Pd(OAc)$_2$ (2.7 mg, 0.0122 mmol) were added, and the reaction mixture stirred at 80° C. for 17 h. Additional reagents (same molar equivalents except triethylamine (0.034 ml, 0.243 mmol) and the mixture was stirred at 100° C. for an additional 3 h. Reagent addition was repeated and the mixture again stirred at 100° C. for 17 h. The solution was partitioned between EtOAc and H$_2$O and the organic phase washed with brine, dried (Na$_2$SO$_4$), concentrated, and the crude product purified by SiO$_2$ chromatography (stepwise gradient: 30 to 50% Et$_2$O/hexanes) to afford 67 mg (60%) of 12.5. MS (ESI) 459.4 (MH+).

EXAMPLE 45

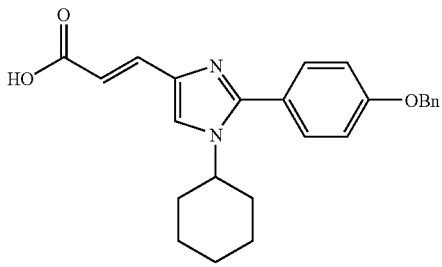

(2E)-3-{2-[4-(benzyloxy)phenyl]-1-cyclohexyl-1H-imidazol-4-yl}-2-propenoic acid (12.6). To a solution of 12.5 (53 mg, 0.116 mmol) in $CH_2Cl_2$ (2 ml) was added trifluoroacetic acid (3 ml) and the mixture was stirred for 17 h and concentrated. The crude product was purified by semi-preparative HPLC (gradient elution: 50 to 100% $CH_3CN$/ $H_2O$+0.1% TFA) to afford 43 mg (72%) of 12.6. HRMS (ESI) calc'd for $C_{25}H_{27}N_2O_3$ 403.2022, found 403.2026 (M+H$^+$); $^1$H NMR (300 MHz, CDCl$_3$) δ 7.59–7.56 (m, 3H), 7.46–7.34 (m, 6H), 7.13 (d, J=8.4, 2H), 6.74 (d, J=15.7, 1H), 5.12 (s, 2H), 4.20–4.11 (m, 1H), 2.07–2.03 (m, 2H), 1.95–1.89 (m, 2H), 1.75–1.71 (m, 3H), 1.28–1.25 (m, 3H).

Intermediate 12.7

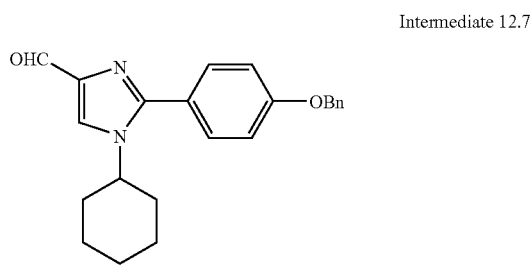

2-[4-(benzyloxy)phenyl]-4-carboxaldehyde-1-cyclohexyl-1H-imidazole (12.7). To a solution of 12.4 (683 mg, 1.66 mmol), in THF (7 ml) at −78° C., was added tert-BuLi (1.7 M in pentane, 2.25 ml, 3.82 mmol). The mixture was stirred at −78° C. for 0.5 h, quenched with DMF (0.64 ml, 8.30 mmol), and allowed to warm to rt. Saturated NH$_4$Cl solution (1 ml) was added, and the resulting mixture partitioned between EtOAc and H2O. The organic phase was washed with brine, dried (Na2SO4), concentrated, and the crude product purified by silica gel chromatography (35% EtOAc/hexanes) to afford 387 mg (65%) of 12.7. MS (ESI) 361.3 (MH$^+$).

EXAMPLE 46

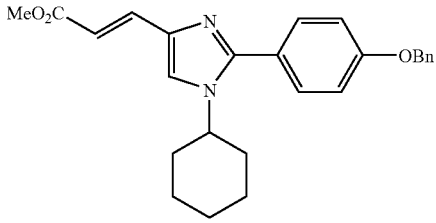

Methyl (2E)-3-{2-[4-(benzyloxy)phenyl]-1-cyclohexyl-1H-imidazol-4-yl}-2-propenoate (12.8). According to the procedure for preparation of 4.1, aldehyde 12.7 (150 mg, 0.416 mmol) was reacted with methyl (triphenylphosphoranylidene)acetate (209 mg, 0.624 mmol) to yield 128 mg (74%) of 12.8. MS (ESI) 417.3 (MH$^+$).

Intermediate 12.9

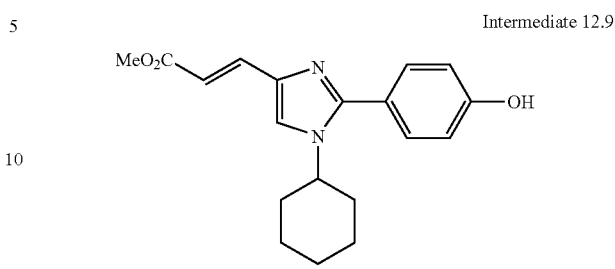

Methyl (2E)-3-{2-[4-(hydroxy)phenyl]-1-cyclohexyl-1H-imidazol-4-yl}-2-methyl-2-propenoate (12.9). According to the procedure for preparation of 4.3, ester 12.8 (117 mg, 0.281 mmol) was reacted with BC13 (1.40 mmol) to yield 69 mg (75%) of 12.9. MS (ESI) 327.3 (MH$^+$).

EXAMPLE 47

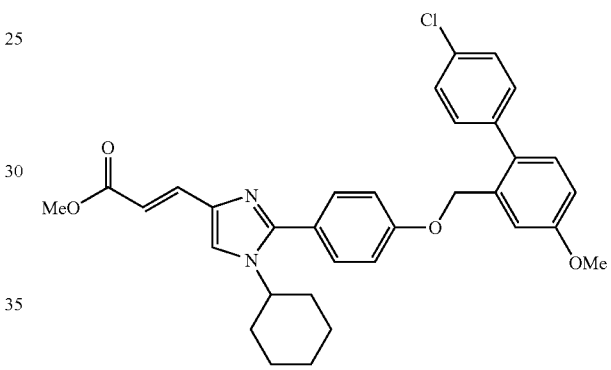

Methyl (2E)-3-(2-{4-[(4'-chloro-4-methoxy-1,1'-biphenyl-2-yl)methoxy]phenyl}-1-cyclohexyl-1H-imidazol-4-yl)-2-propenoate (12.10). According to the procedure for preparation of 4.4, phenol 12.9 (60 mg, 0.184 mmol) was alkylated with (4'-chloro-4-methoxy-1,1'-biphenyl-2-yl)methyl bromide (63 mg, 0.202 mmol), to yield 75 mg (73%) of 12.10. MS (ESI) 557.4 (MH$^+$).

EXAMPLE 48

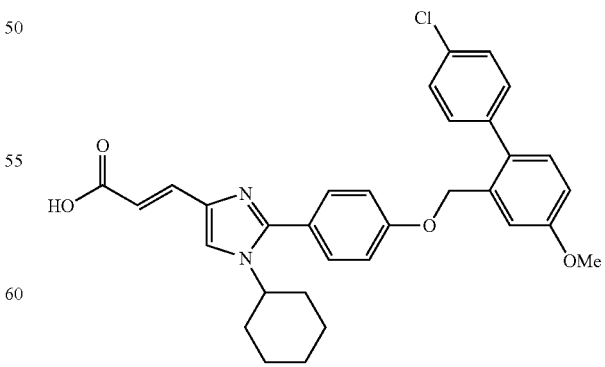

(2E)-3-(2-{4-[(4'-chloro-4-methoxy-1,1'-biphenyl-2-yl)methoxy]phenyl}-1-cyclohexyl-1H-imidazol-4-yl)-2-propenoic acid (12.11). According to the procedure for preparation of 4.5, ester 12.10 (60 mg, 0.108 mmol) was saponified to yield 56 mg (79%) of 12.11. HRMS (ESI) calc'd for $C_{32}H_{32}ClN_2O_4$ 543.2051, found 543.2005 (M+H+); 1H NMR (300 MHz, CDCl$_3$) δ 7.56–7.53 (m, 3H), 7.43–7.24 (m, 6H), 7.14 (d, J=3.0, 1H), 7.03–6.95 (m, 3H), 6.74 (d, J=16.1, 1H), 4.95 (s, 2H), 4.21–4.11 (m, 1H), 3.86 (s, 3H), 2.07–2.03 (m, 2H), 1.89–1.86 (m, 2H), 1.80–1.65 (m, 3H), 1.29–1.23 (m, 3H).

EXAMPLE 49

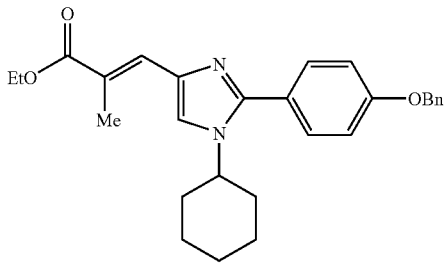

Ethyl (2E)-3-{2-[4-(benzyloxy)phenyl]-1-cyclohexyl-1H-imidazol-4-yl}-2-methyl-2-propenoate (13.1). According to the procedure for preparation of 4.1, aldehyde 12.7 (225 mg, 0.624 mmol) was reacted with (1-ethoxycarbonylethyl)triphenylphosponium bromide (346 mg, 0.780 mmol) to yield 234 mg (85%) of 13.1. MS (ESI) 445.5 (MH$^+$).

EXAMPLE 50

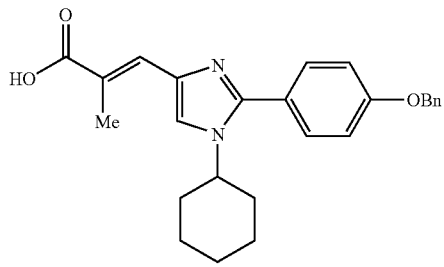

(2E)-3-{2-[4-(benzyloxy)phenyl]-1-cyclohexyl-1H-imidazol-4-yl}-2-methyl-2-propenoic acid (13.2.). According to the procedure for preparation of 4.2, ester 13.1 (50 mg, 0.112 mmol) was saponified to yield 38 mg (64%) of 13.2. HRMS (ESI) calc'd for $C_{26}H_{29}N_2O_3$ 417.2178, found 417.2180 (MH$^+$); 1H NMR (300 MHz, CDCl$_3$) δ 7.60–7.57 (m, 3H), 7.46–7.35 (m, 6H), 7.14 (d, J=8.4, 2H), 5.12 (s, 2H), 4.20–4.16 (m, 1H), 2.10–2.05 (m, 5H), 1.91–1.74 (m, 5H), 1.31–1.29 (m, 3H).

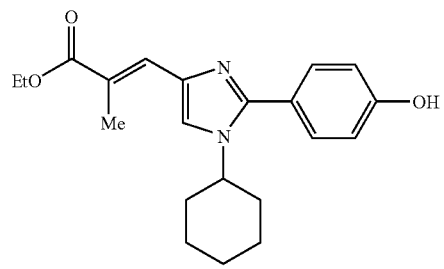

Ethyl (2E)-3-{2-[4-(hydroxy)phenyl]-1-cyclohexyl-1H-imidazol-4-yl}-2-methyl-2-propenoate (13.3). According to the procedure for preparation of 4.3, ester 13.1 (167 mg, 0.376 mmol) was treated with BCl$_3$ (1.88 mmol) to yield 80 mg (60%) of 13.3. MS (ESI) 355.3 (MH$^+$).

EXAMPLE 51

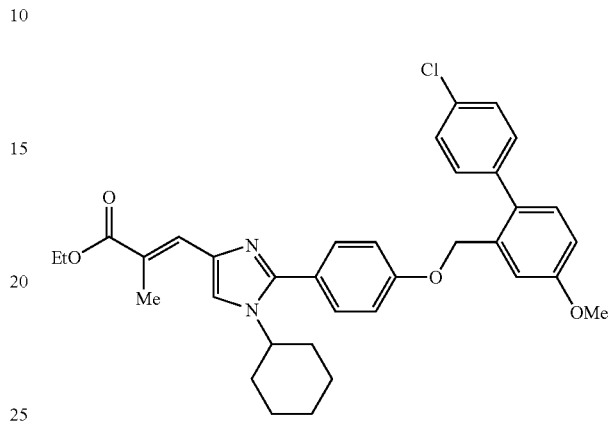

Ethyl (2E)-3-(2-{4-[(4'-chloro-4-methoxy-1,1'-biphenyl-2-yl)methoxy]phenyl}-1-cyclohexyl-1H-imidazol-4-yl)-2-methyl-2-propenoate (13.4). According to the procedure for preparation of 4.4, phenol 13.3 (73 mg, 0.206 mmol) was alkylated with (4'-chloro-4-methoxy-1,1'-biphenyl-2-yl)methyl bromide (71 mg, 0.227 mmol), to yield 59 mg (49%) of 13.4. MS (ESI) 585.4 (MH$^+$).

EXAMPLE 52

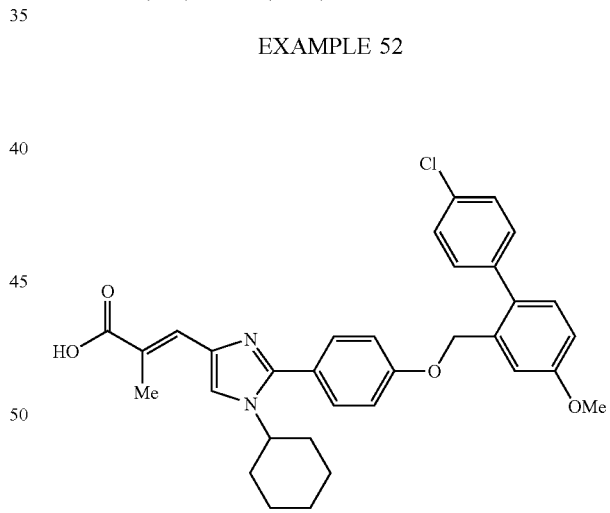

(2E)-3-(2-{4-[(4'-chloro-4-methoxy-1,1'-biphenyl-2-yl)methoxy]phenyl}-1-cyclohexyl-1H-imidazol-4-yl)-2-methyl-2-propenoic acid (13.5). According to the procedure for preparation of 4.5, ester 13.4 (55 mg, 0.0940 mmol) was saponified to yield 42 mg (67%) of 13.5. HRMS (ESI) calc'd for $C_{33}H_{34}ClN_2O_4$ 557.2207, found 557.2216 (MH$^+$); $^1$H NMR (300 MHz, CDCl$_3$) δ 7.57–7.54 (m, 3H), 7.42–7.24 (m, 6H), 7.15 (d, J=2.5, 1H), 7.03 (d, J=8.8, 2H), 6.97 (d,d J=8.5, 2.6, 1H), 4.95 (s, 2H), 4.23–4.11 (m, 1H), 3.87 (s, 3H), 2.11–2.03 (m, 5H), 1.95–1.93 (m, 2H), 1.80–1.76 (m, 3H), 1.40–1.21 (m, 3H).

Intermediate 13.6

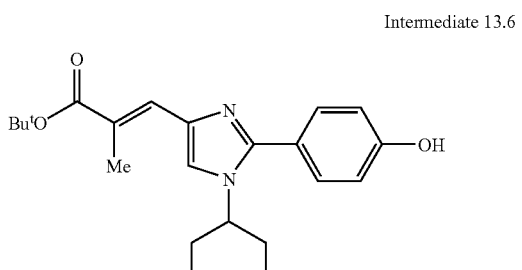

t-Butyl (2E)-3-{2-[4-(hydroxy)phenyl]-1-cyclohexyl-1H-imidazol-4-yl}-2-methyl-2-propenoate (13.6). According to the procedure for preparation of 4.1, aldehyde 12.7 (300 mg, 0.83 mmol) was reacted with (1-t-butoxycarbonylethyl)-triphenylphosponium bromide (350 mg, 0.88 mmol), and the resulting product was dissolved in ethanol (2 ml) and 10% Pd/C (400 mg) added followed by addition of 1,4-cyclhexadiene (excess 0.8 g). The reaction mixture was stirred at 45° C. for 10 h, filtered, and concentrated to yield 190 mg (60%) of 13.6. MS (ESI) 383.27 (MH$^+$).

EXAMPLE 53

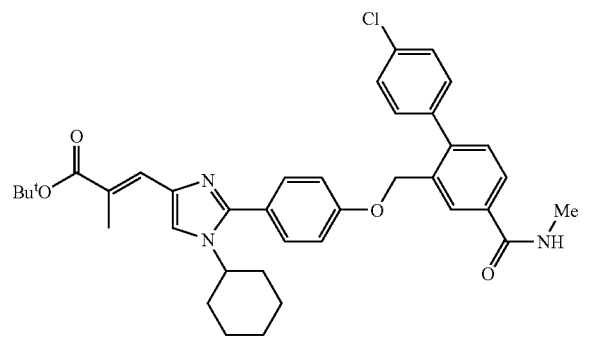

Butoxy$^t$ (2E)-3-(2-{4-[(4'-chloro-4-N-methylcarbamoyl-1,1'-biphenyl-2-yl)methoxy]phenyl}-1-cyclohexyl-1H-imidazol-4-yl)-2-methyl-2-propenoate. Ester 13.6 (20 mg, 0.052 mmol), 2-(hydroxylmethyl)-4'chloro-N-methyl-1,1'-biphenyl-4-caroxamide (14.4 mg, 0.52 mmol), and triphenylphosphene (16.5 mg, 0.063 mmol) were taken up in THF (0.25 ml) and cooled to 0° C. under N$_2$ and diisopropylazo-dicarboxylate (12 mg, 0.06 mmol), dissolved in an equal volume of the same solvent, was added dropwise. The reaction was allowed to stand at rt for 18 h and an addition equivalent of each reagent was added to the reaction mixture. Water (3 drops) was added, concentrate to remove volatiles, and subject to reverse phase HPLC as above to yield 26 mg (66%) of 13.7. MS (ESI) 640.19 (MH$^+$).

EXAMPLE 54

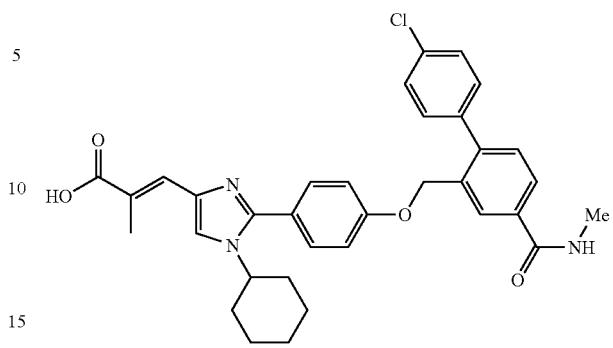

(2E)-3-(2-{4-[(4'-chloro-4-N-methylcarbamoyl-1,1'-biphenyl-2-yl)methoxy]phenyl}-1-cyclohexyl-1H-imidazol-4-yl)-2-methyl-2-propenoic acid. According to the procedure for preparation of 12.6, ester 13.7 (20 mg, 0.031 mmol) was cleaved to acid to give 22.5 mg (100%) of 13.8 as TFA salt. HRMS (ESI) calc'd for $C_{34}H_{34}ClN_3O_4$ 584.2316, found 584.2319 (MH$^+$); $^1$H NMR (300 MHz, CD$_3$OD) δ 8.05–8.10 (m, 2H), 7.87–7.90 (m, 1H), 7.60 (d, J=8.8, 2H), 7.42–7.46 (m, 6H), 7.17 (d, J=8.8, 2H), 5.12 (s, 2H), 4.24–4.28 (m, 1H), 3.30 (s, 3H), 2.94 (s, 3H), 1.91–2.06 (m, 6H), 1.27–1.37 (m, 4H).

We claim:

1. A compound of Formula (I)

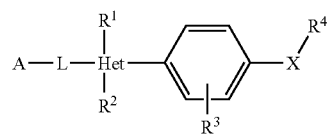

where:

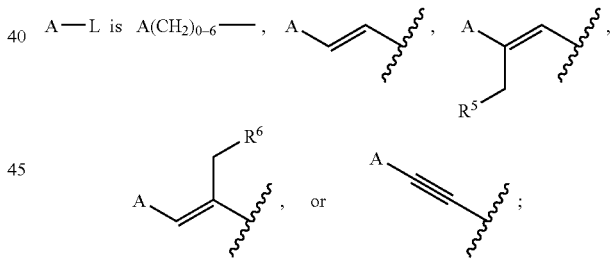

A is CO$_2$; R$^5$, CONSO$_2$R$^5$, or SO$_2$NCOR$^5$,
Het is pyrazole,
X is O;
R$^1$ in hydrogen, halogen, C$_{1-6}$alkyl, trifluoromethyl, or phenyl;
R$^2$ is a saturated C$_{3-7}$cycloalkyl or a saturated C$_{5-12}$ bridged bicycloalkyl;
R$^3$ is hydrogen, halogen, C$_{1-6}$alkyl, or C$_{1-6}$alkoxy;

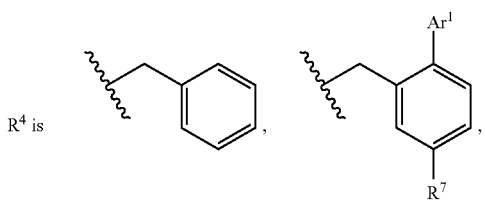

-continued

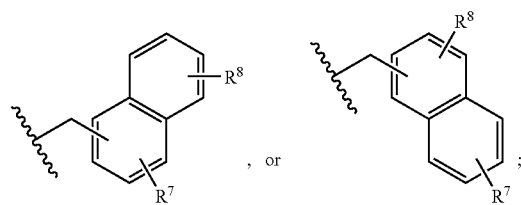

$R^5$ is hydrogen or $C_{1-6}$alkyl;

$R^6$ is hydrogen, methyl, or $OR^5$;

$R^7$ is $C_{1-6}$alkoxy, cyano, trifluoromethyl, —$CO_2R^5$, —$CONR^9R^{10}$, $SO_2R^5$, or $SO_2NR^9R^{10}$;

$R^8$ is hydrogen, halogen, $C_{1-6}$alkyl, $C_{1-6}$alkoxy, cyano, trifluoromethyl, aceto, $CO_2R^5$, or $CONR^9R^{10}$;

$R^9$ and $R^{10}$ are independently hydrogen, $C_{1-6}$alkyl, —$CH_2CH_2OH$; or $NR^9R^{10}$ taken together form pyrrolidine, piperidine, 4-hydroxypiperidine, piperazine, 4-methylpiperazine, morpholine, or thiomorpholine; and $Ar^1$ is thiophene or phenyl substituted with 0–3 substituents selected from halogen, $C_{1-6}$alkyl, $C_{1-6}$alkoxy, cyano, trifhoromethyl, aceto, $CO_2R^5$, and $CONR^9R^{10}$;

or a pharmaceutically acceptable salt or solvate of these compounds.

2. A compound of claim 1 where A-L is $R^5O_2CCH_2CH_2CH_2$,

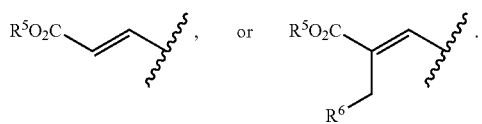

3. A compound of claim 1 where Formula (I) is Formula (Ia)

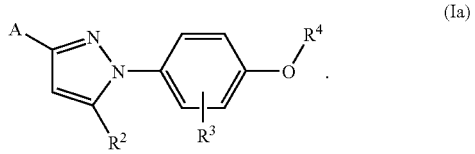

4. A compound of claim 1 where Formula (I) is Formula (Ib)

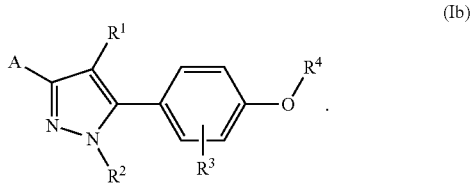

5. A compound of claim 1 where $R^2$ is cyclohexyl.

6. A compound of claim 1 where $R^4$ is

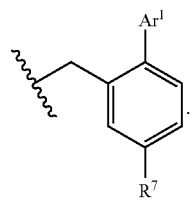

7. A compound of claim 1 selected from the group consisting of
(1) ethyl 1-cyclohexyl-5-(4-benzyloxyphenyl)-1H-pyrazole-3-carboxylate;
(2) methyl (2E)-3-{5-[4-(benzyloxy)phenyl]-1-cyclohexyl-1H-pyrazol-3-yl}-2-propenoate;
(3) (2E)-3-[1-cyclohexyl-5-(4-benzyloxyphenyl)-1H-pyrazol-3-yl]-2-propenoic acid;
(4) methyl (2E)-3-(5-{4-[(4'-chloro-4-methoxy-1,1'-biphenyl-2-yl)methoxy]phenyl}-1-cyclohexyl-1H-pyrazol-3-yl)-2-propenoate;
(5) (2E)-3-(5-{4-[(4'-chloro-4-methoxy-1,1'-biphenyl-2-yl)methoxy]phenyl}-1-cyclohexyl-1H-pyrazol-3-yl)-2-propenoic acid;
(6) ethyl (2E)-3-{5-[4-(benzyloxy)phenyl]-1-cyclohexyl-1H-pyrazol-3-yl}-2-methyl-2-propenoate;
(7) (2E)-3-{5-[4-(benzyloxy)phenyl]-1-cyclohexyl-1H-pyrazol-3-yl}-2-methyl-2-propenoic acid;
(8) ethyl (2E)-3-(5-{4-[(4'-chloro-4-methoxy-1,1'-biphenyl-2-yl)methoxy]phenyl}-1-cyclohexyl-1H-pyrazol-3-yl)-2-methyl-2-propenoate;
(9) (2E)-3-(5-{4-[(4'-chloro-4-methoxy-1,1'-biphenyl-2-yl)methoxy]phenyl}-1-cyclohexyl-1H-pyrazol-3-yl)-2-methyl-2-propenoic acid;
(10) ethyl (2E)-3-(5-{4-[(t-butyl-2-bromo-5-phenylcarboxylate)methoxy]phenyl}-1-cyclohexyl-1H-pyrazol-3-yl)-2-methyl-2-propenoate;
(11) ethyl (2E)-3-(5-{4-[(4'-chloro-4-t-butoxycarbonyl-1,1'-biphenyl-2-yl)methoxy]phenyl}-1-cyclohexyl-1H-pyrazol-3-yl)-2-methyl-2-propenoate;
(12) ethyl (2E)-3-(5-{4-[(4'-Chloro-4-N-methylcarbamoyl-1,1'-biphenyl-2-yl)methoxy]phenyl}-1-cyclohexyl-1H-pyrazol-3-yl)-2-methyl-2-propenoate;
(13) (2E)-3-(5-{4-[(4'-Chloro-4-N-methylcarbamoyl-1,1'-biphenyl-2-yl)methoxy]phenyl}-1-cyclohexyl-1H-pyrazol-3-yl)-2-methyl-2-propenoic acid;
(14) methyl 3-{5-[4-(benzyloxy)phenyl]-1-cyclohexyl-1H-pyrazol-3-yl}propanoate;
(15) 3-{5-[4-(benzyloxy)phenyl]-1-cyclohexyl-1H-pyrazol-3-yl}propanoic acid;
(16) methyl 3-(5-{4-[(4'-chloro-4-methoxy-1,1'-biphenyl-2-yl)methoxy]phenyl}-1-cyclohexyl-1H-pyrazol-3-yl)propanoate;
(17) 3-(5-{4-[(4'-chloro-4-methoxy-1,1'-biphenyl-2-yl)methoxy]phenyl}-1-cyclohexyl-1H-pyrazol-3-yl)propanoic acid;
(18) ethyl 3-{5-[4-(benzyloxy)phenyl]-1-cyclohexyl-1H-pyrazol-3-yl}-2-propynoate;
(19) 3-{5-[4-(benzyloxy)phenyl]-1-cyclohexyl-1H-pyrazol-3-yl}-2-propynoic acid;
(20) ethyl 3-(5-{4-[(4'-chloro-4-methoxy-1,1'-biphenyl-2-yl)methoxy]phenyl}-1-cyclohexyl-1H-pyrazol-3-yl)-2-propynoate;

(21) 3-(5-{4-[(4'-chloro-4-methoxy-1,1'-biphenyl-2-yl)methoxy]phenyl}-1-cyclohexyl-1H-pyrazol-3-yl)-2-propynoic acid;

(22) ethyl 5-[4-(benzyloxy)phenyl]-4-bromo-1-cyclohexyl-1H-pyrazole-3-carboxylate;

(23) methyl (2E)-3-{5-[4-(benzyloxy)phenyl]-4-bromo-1-cyclohexyl-1H-pyrazol-3-yl}-2-propenoate;

(24) (2E)-3-{5-[4-(benzyloxy)phenyl]-4-bromo-1-cyclohexyl-1H-pyrazol-3-yl}-2-propenoic acid;

(25) methyl (2E)-3-{5-[4-(benzyloxy)phenyl]-1-cyclohexyl-4-phenyl-1H-pyrazol-3-yl}-2-propenate;

(26) (2E)-3-{5-[4-(benzyloxy)phenyl]-1-cyclohexyl-4-phenyl-1H-pyrazol-3-yl}-2-propenoic acid;

(27) methyl (2E)-3-(5-{4-[4'-chloro-4-methoxy-1,1-biphenyl)methoxy]phenyl}-1-cyclohexyl-4-phenyl-5-1H-pyrazol-3-yl]-2-propenoate;

(28) (2E)-3-(5-{4-[4'-chloro-4-methoxy-1,1-biphenyl)methoxy]phenyl}-1-cyclohexyl-4-phenyl-5-1H-pyrazol-3-yl]-2-propenoic acid;

(29) ethyl 1-[4-(benzyloxy)phenyl]-5-cyclohexyl-1H-pyrazole-3-carboxylate;

(30) methyl (2E)-3-{1-[4-(benzyloxy)phenyl]-5-cyclohexyl-1H-pyrazol-3-yl}-2-propenoate;

(31) (2E)-3-{1-[4-(benzyloxy)phenyl]-5-cyclohexyl-1H-pyrazol-3-yl}-2-propenoic acid;

(32) methyl (2E)-3-(1-{4-[(4'-chloro-4-methoxy-1,1'-biphenyl-2-yl)methoxy]phenyl}-5-cyclohexyl-1H-pyrazol-3-yl)-2-propenoate;

(33) (2E)-3-(1-{4-[(4'-chloro-4-methoxy-1,1'-biphenyl-2-yl)methoxy]phenyl}-5-cyclohexyl-1H-pyrazol-3-yl)-2-propenoic acid;

(34) ethyl (2E)-3-{1-[4-(benzyloxy)phenyl]-5-cyclohexyl-1H-pyrazol-3-yl}-2-methyl-2-propenoate;

(35) (2E)-3-{1-[4-(benzyloxy)phenyl]-5-cyclohexyl-1H-pyrazol-3-yl}-2-methyl-2-propenoic acid;

(36) ethyl (2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoate;

(37) (2E)-3-(1-{4-[(4'-chloro-4-methoxy-1,1'-biphenyl-2-yl)methoxy]phenyl}-5-cyclohexyl-1H-pyrazol-3-yl)-2-methyl-2-propenoic acid;

(38) ethyl (2E)-1-[4-(4'-Chloro-4-methylcarbamoyl-biphenyl-2-ylmethoxy)-phenyl]-5-cyclohexyl-1H-pyrazol-3-yl]-2-methyl-2-propenoate;

(39) (2E)-1-[4-(4'-chloro-4-methylcarbamoyl-biphenyl-2-ylmethoxy)-phenyl]-5-cyclohexyl-1H-pyrazol-3-yl]-2-methyl-2-propenoic acid;

(40) methyl 3-{1-[4-(benzyloxy)phenyl]-5-cyclohexyl-1H-pyrazol-3-yl}propanoate;

(41) 3-{1-[4-(benzyloxy)phenyl]-5-cyclohexyl-1H-pyrazol-3-yl}propenoic acid;

(42) methyl 3-(1-{4-[(4'-chloro-4-methoxy-1,1'-biphenyl-2-yl)methoxy]phenyl}-5-cyclohexyl-1H-pyrazol-3-yl)propanoate;

(43) 3-(1-{4-[(4'-chloro-4-methoxy-1,1'-biphenyl-2-yl)methoxy]phenyl}-5-cyclohexyl-1H-pyrazol-3-yl)propanoic acid.

8. A pharmaceutical composition comprising a therapeutic amount of a compound of claim 1, or its pharmaceutically acceptable salt or solvate, and a pharmaceutically acceptable carrier.

9. A method for inhibiting hepatitis C NS5B RNA-dependent RNA polymerase in a patient in need of such treatment comprising administering a therapeutic amount of a compound of claim 1 to a patient in need of such treatment.

10. A method for treating a hepatitis C viral infection in a patient in need of such treatment comprising administering a therapeutic amount of a compound of claim 1 to a patient in need of such treatment.

11. A method for treating hepatitis C in a patient in need of such treatment comprising administering a therapeutic amount of a compound of claim 1 to a patient in need of such treatment.

* * * * *